(12) United States Patent
Cowart et al.

(10) Patent No.: US 7,470,691 B2
(45) Date of Patent: Dec. 30, 2008

(54) FUSED BICYCLIC AROMATIC COMPOUNDS THAT ARE USEFUL IN TREATING SEXUAL DYSFUNCTION

(75) Inventors: Marlon D. Cowart, Round Lake Beach, IL (US); Steven P. Latshaw, Round Lake Beach, IL (US); Sherry L. Nelson, Chicago, IL (US); Andrew O. Stewart, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/747,955

(22) Filed: May 14, 2007

(65) Prior Publication Data

US 2007/0265249 A1 Nov. 15, 2007

Related U.S. Application Data

(62) Division of application No. 10/443,814, filed on May 23, 2003, now Pat. No. 7,057,042.

(60) Provisional application No. 60/384,291, filed on May 29, 2002.

(51) Int. Cl.
*A61K 31/496* (2006.01)
*A61K 31/506* (2006.01)

(52) U.S. Cl. .............................. 514/252.18; 514/253.04

(58) Field of Classification Search ...................... None
See application file for complete search history.

(56) References Cited

U.S. PATENT DOCUMENTS

| | | | |
|---|---|---|---|
| 5,182,280 A | 1/1993 | Cuberes-Altisent et al. | |
| 5,576,319 A * | 11/1996 | Baker et al. | 514/252.11 |
| 5,700,802 A * | 12/1997 | Curtis et al. | 514/253.04 |
| 5,792,768 A | 8/1998 | Kulagowski et al. | |
| 5,976,497 A * | 11/1999 | Pollak et al. | 424/1.85 |
| 6,656,935 B2 | 12/2003 | Yamada et al. | |
| 2004/0002488 A1 | 1/2004 | Cowart | |

FOREIGN PATENT DOCUMENTS

WO 01/19802 3/2001
WO 03/101994 * 12/2003

OTHER PUBLICATIONS

Curtis et al. Bioorganic & Medicinal Chemistry Letters, vol. 9, pp. 585-588 (1999).*
"Male and female sexual dysfunction: Blockbuster indication for multiple pharmacological targets" by LeadDiscovery, Available at:www.leaddiscovery.co.uk/dossiers/MDI002/Sexual%20dysfunction.htm (2002).*
Bendele et al., "Anti-inflammatory activity of pergolide, a dopamine receptor agonist," Journal of Pharmacology and Experimental Therapeutics 259:169-175 (1991).
Chen et al., "Effects of dopamine, apomorphine, γ-hydroxybutyric acid, haloperidol and pimozide on reflex bradycardia in rats[1]," Journal of Pharmacology and Experimental Therapeutics 214:427-432 (1980).
Coward et al., "Chimeric G proteins allow a high-throughput signaling assay of $G_i$-coupled receptors," Analytical Biochemistry 270:242-248 (1999).
Hahn et al, "Primate cardiovascular responses mediated by dopamine receptors: effects of N,N-di-n-propyldopamine and LY171555," Journal of Pharmacology and Experimental Therapeutics 229:132-138 (1984).
Hrib, "the dopamine $D_4$ receptor: a controversial therapeutic target," Drugs of the Future 25(6):587-611 (2000).
IUPAC Recommendations for Section E, Fundamental Stereochemistry, Pure Appl. Chem. 45:13-30 (1976).
Lissoni et al., "Efficacy of bromocriptine in the treatment of metastatic breast cancer- and prostate cancer-related hyperprolactinemia," Neuroendocrinology Letters 21:405-408 (2000).
Melis et al., "Dopamine and sexual behavior," Neuroscience and Biobehavioral Reviews 19(1):19-38 (1995).
Missale et al., "Dopamine receptors: from structure to function," Physiological Reviews 78:189-225 (1998).
Prescott, Methods in Cell Biology, vol. XIV, Academic Press, New York, NY p. 33 et seq. (1976).

* cited by examiner

*Primary Examiner*—Emily Bernhardt
(74) *Attorney, Agent, or Firm*—B. Gregory Donner

(57) ABSTRACT

The present invention relates to the use of compounds of formula (I)

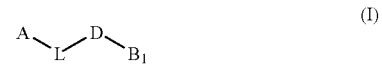

for the treatment of sexual dysfunction and to compositions containing compounds of formula (I) for the treatment of sexual dysfunction, wherein A, L, D and $B_1$ are as described in the specification.

7 Claims, No Drawings

FUSED BICYCLIC AROMATIC COMPOUNDS THAT ARE USEFUL IN TREATING SEXUAL DYSFUNCTION

This application is a divisional of U.S. patent application Ser. No. 10/443,814 filed May 23, 2003, now U.S. Pat. No. 7,057,042, which claims benefit to U.S. Provisional Application Ser. No. 60/384,291, filed May 29, 2002, incorporated herein by reference.

TECHNICAL FIELD

The present invention relates to the use of fused bicyclic aromatic compounds and compositions containing these compounds for the treatment of sexual dysfunction.

BACKGROUND OF THE INVENTION

Preclinical evidence indicates that dopamine (DA) plays a role in penile erection in mammals. Sexual stimulation can be initiated by sensory (erotic) information reaching the cerebral cortex in mammals. The cerebral cortex has extensive neuronal connections with limbic structures like the amygdala, as well as midbrain structures like the periaqueductal gray (PAG) and the hypothalamus. Two important nuclei in the hypothalamus are the medial preoptic area (MPOA) and the paraventricular nucleus (PVN). The MPOA and PVN nuclei play a critical role in sexual behavior as bilateral lesions of these areas completely eliminate male sexual behavior. The incerto-hypothalamic dopaminergic pathway that innervates the PVN and the MPOA nuclei has been associated with the pro-erectile effect of DA agents. Systemic administration of DA receptor agonists like apomorphine ((6aR) 5,6,6a,7-tetrahydro-6-methyl-4H-dibenzo[de,g]quinoline-10,11-diol), quinpirole and (-) 3-(3-hydroxyphenyl)-N-propylpiperidine (3-PPP) facilitate penile erection in rats, an effect blocked by haloperidol, a central DA antagonist. As the erectogenic effect can not be blocked by domperidone, a peripheral DA antagonist, it is believed that the pro-erectile effect of DA agonists is centrally mediated.

Clinical data also indicates that DA systems in the CNS play a role on the regulation of male sexual behavior as indicated by the sexual stimulatory effect of L-dopa in Parkinson's patients and by the pro-erectile effect of apomorphine in humans.

DA receptors belong to a superfamily of protein receptors that signal across the cell membrane by coupling to intracellular GTP-binding proteins. Several G proteins have been identified (including Gs, Gq and Gi) that lead to specific intracellular events.

There are five known DA receptors which are classified into two groups, $D_1$-like and $D_2$-like. The $D_1$-like receptors include $D_1$ and $D_5$. The $D_2$-like receptors include $D_2$, $D_3$ and $D_4$. The $D_1$-like family receptor subtypes are $G_s$-coupled and can activate adenylate cyclase. The $D_2$-like family receptor subtypes are $G_i$-coupled and they increase intracellular calcium level and inhibit adenylate cyclase.

The $D_1$-like family members are $G_s$-coupled receptors that can activate adenylate cyclase. The $D_1$ receptor is the most abundant and widespread DA receptor in the CNS both by mRNA expression and by immunohistochemical studies. It is found in the striatum, nucleus accumbens and olfactory tubercle as well as the limbic system, hypothalamus and thalamus. The $D_1$ receptor expression has been reported in the heart and kidney, and despite that the function of these peripheral $D_1$ receptors remains to be clarified, its role on the control of hemodynamic variables has been confirmed. The $D_5$ receptor, while having a higher affinity for DA than the $D_1$ receptor, is sparsely distributed in the CNS with no evidence of expression outside the CNS.

The $D_2$-like family members are $G_i$ coupled receptors that inhibit adenylate cyclase and increase intracellular calcium levels. The $D_2$ receptor is the most abundant of the $D_2$-like receptors and is located in brain areas such as the striatum and substantia nigra, and in peripheral areas such as the heart, pituitary gland and kidney. The $D_3$ receptor is found abundantly in the islands of Calleja with distinct cluster populations in the ventral striatum/nucleus accumbens regions, olfactory tubercle, dendate gyrus and striatal cortex.

Expression of the $D_4$ receptor has been documented by in situ RNA hybridization and immunohistochemical studies. Recently, studies revealed that $D_4$ expression is highest in the entorhinal cortex, lateral septal nucleus, hippocampus and the medial preoptic area of the hypothalamus. Localization of $D_4$ is distinct from the distribution of $D_2$ in the brain, as $D_2$ receptors are most abundant in striatal areas. The expression of $D_4$ receptors in the MPOA of the hypothalamus is of importance to the facilitation of penile erection in view of the role of the hypothalamus as an area of integration between the cortex and the spinal pathways. The participation of $D_4$ receptors in other CNS regions, thalamic, subthalamic and spinal can not be excluded.

The present invention identifies a therapeutic use for the compounds of formula (I) in the treatment of sexual dysfunction in mammals. More specifically, these compounds are useful in the treatment of sexual dysfunction including, but not limited to, male erectile dysfunction (MED).

SUMMARY OF THE INVENTION

The present invention relates to a method of treating sexual dysfunction in a mammal, in particular humans, comprising administering to the mammal a therapeutically effective amount of a compound of formula (I)

or a pharmaceutically acceptable salt, ester, amide, N-oxide, or prodrug thereof, wherein
A is selected from the group consisting

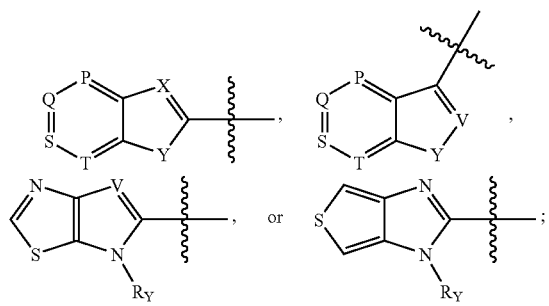

X is selected from $CR_X$ or N;
Y is selected from $NR_Y$, O, or S;
V is selected from $CR_V$ or N;
P is selected from $CR_P$ or N;
Q is selected from $CR_Q$ or N;
S is selected from $CR_S$ or N;

T is selected from $CR_T$ or N;

provided that 0, 1, or 2 of P, Q, S, or T are N;

provided that when P is $CR_P$, Q is $CR_Q$, S is $CR_S$, T is $CR_T$, and Y is N, then X is $CR_X$;

$R_P$, $R_Q$, $R_S$, $R_T$, $R_V$, and $R_X$ are independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, or ($NZ_3Z_4$)sulfonyl;

$R_Y$ is selected from hydrogen, alkenyl, alkoxycarbonyl, alkyl, arylalkyl, of ($NZ_3Z_4$)carbonyl;

$Z_1$ and $Z_2$ are each independently selected from hydrogen, alkyl, alkylcarbonyl, alkylsulfonyl, aryl, arylalkyl, arylalkylsulfonyl, arylsulfonyl, or formyl;

$Z_3$ and $Z_4$ are each independently selected from hydrogen, alkyl, aryl, or arylalkyl;

L is alkylene;

D is selected from

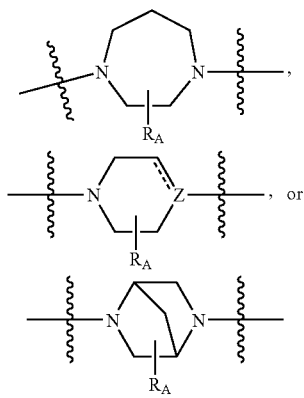

wherein the left end is attached to L and the right end is attached to $B_1$;

$R_A$ is selected from hydrogen or alkyl;

Z is selected from N, C or CH;

--- is a bond when Z is C and --- is absent when Z is N or CH;

$B_1$ is selected from

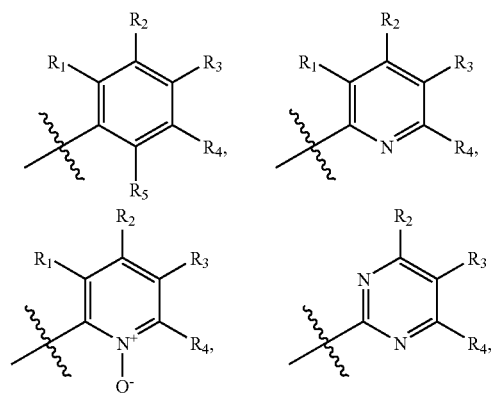

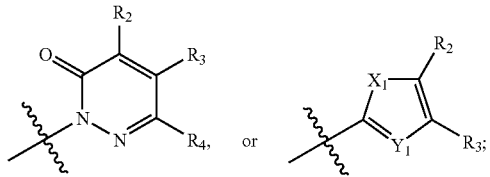

$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, or ($NZ_3Z_4$)sulfonyl;

$X_1$ is selected from N($R_6$), O or S;

$Y_1$ is selected from C($R_7$) or N;

$R_6$ is selected from hydrogen or alkyl;

$R_7$ is selected from hydrogen or alkyl; and provided that the compound of formula (I) is other than 5-fluoro-2-{[4-(2-pyridinyl)-1-piperazinyl]methyl}-1H-indole.

DETAILED DESCRIPTION OF THE INVENTION

All patents, patent applications, and literature references cited in the specification are herein incorporated by reference in their entirety.

In its principle embodiment, the present invention relates to a method of treating sexual dysfunction in a mammal, in particular humans, comprising administering to the mammal a therapeutically effective amount of a compound of formula (I)

In its principle embodiment, the present invention relates to a method of treating sexual dysfunction in a mammal, in particular humans, comprising administering to the mammal a therapeutically effective amount of a compound of formula (I)

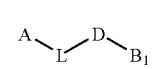 (I)

or a pharmaceutically acceptable salt, ester, amide, N-oxide, or prodrug thereof, wherein A is selected from the group consisting

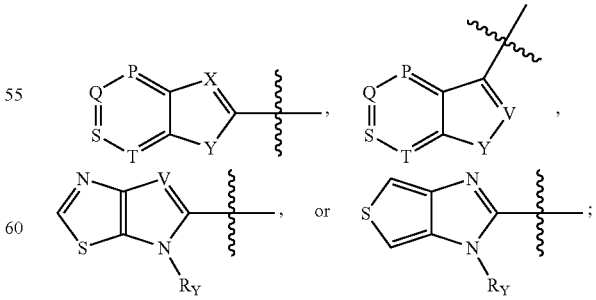

X is selected from $CR_X$ or N;

Y is selected from $NR_Y$, O or S;

V is selected from $CR_V$ or N;

P is selected from $CR_P$ or N;
Q is selected from $CR_Q$ or N;
S is selected from $CR_S$ or N;
T is selected from $CR_T$ or N;
provided that 0, 1, or 2 of P, Q, S, or T are N;
provided that when P is $CR_P$, Q is $CR_Q$, S is $CR_S$, T is $CR_T$, and Y is N, then X is $CR_X$;

$R_P$, $R_Q$, $R_S$, $R_T$, $R_Y$, and $R_X$ are independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, or ($NZ_3Z_4$)sulfonyl;

$R_Y$ is selected from hydrogen, alkenyl, alkoxycarbonyl, alkyl, arylalkyl, of ($NZ_3Z_4$)carbonyl;

$Z_1$ and $Z_2$ are each independently selected from hydrogen, alkyl, alkylcarbonyl, alkylsulfonyl, aryl, arylalkyl, arylalkylsulfonyl, arylsulfonyl, or formyl;

$Z_3$ and $Z_4$ are each independently selected from hydrogen, alkyl, aryl, or arylalkyl;

L is alkylene;
D is selected from

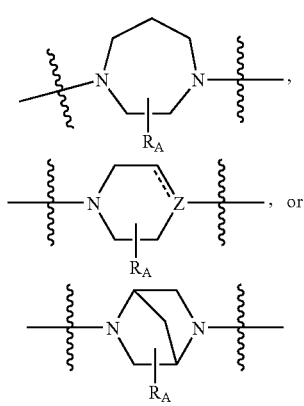

wherein the left end is attached to L and the right end is attached to $B_1$;

$R_A$ is selected from hydrogen or alkyl;
Z is selected from N, C or CH;
is a bond when Z is C and --- is absent when Z is N or CH;
$B_1$ is selected from

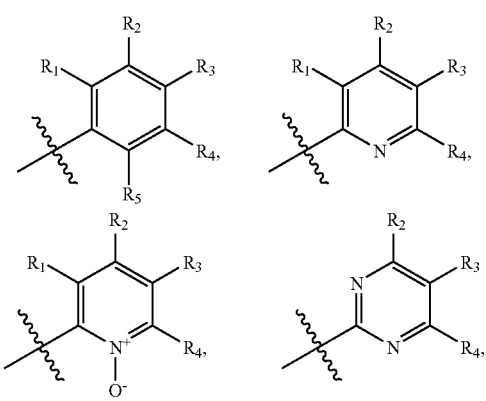

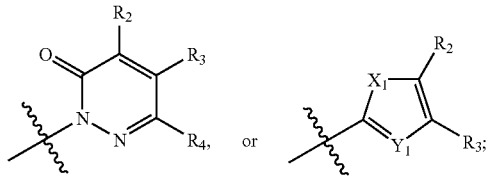

$R_1$, $R_2$, $R_3$, $R_4$ and $R_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, ($NZ_3Z_4$)carbonyl, or ($N7Z_3Z_4$)sulfonyl;

$X_1$ is selected from N($R_6$), O or S;
$Y_1$ is selected from C($R_7$) or N;
$R_6$ is selected from hydrogen or alkyl;
$R_7$ is selected from hydrogen or alkyl and provided that the compound of formula (I) is other than 5-fluoro-2-{[4-(2-pyridinyl)-1-piperazinyl]methyl}-1H-indole.

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

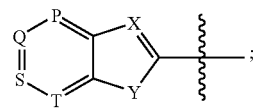

D is

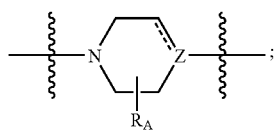

$B_1$ is

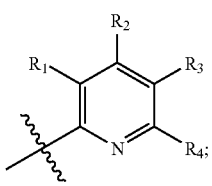

and P, Q, S, T, X, Y, Z, $R_1$, $R_2$, $R_3$, $R_4$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

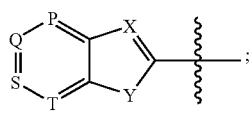

D is

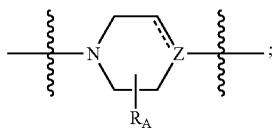

$B_1$ is

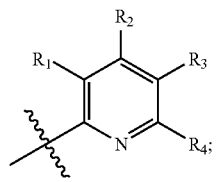

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, Z, $R_1$, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I), or a pharmaceutically acceptable salt, ester, amide, N-oxide, or prodrug thereof, wherein A is

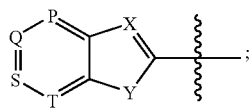

D is

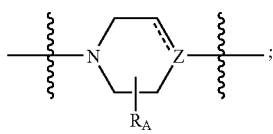

$B_1$ is

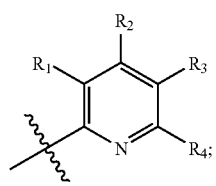

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

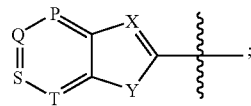

D is

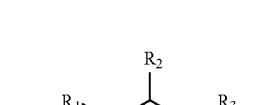

$B_1$ is

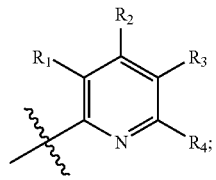

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

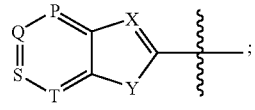

D is

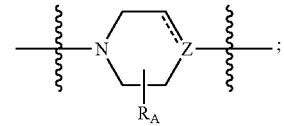

$B_1$ is

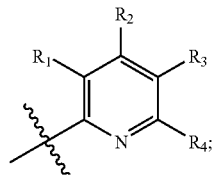

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; and $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

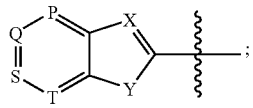

D is

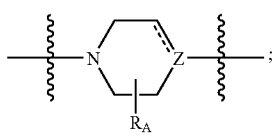

$B_1$ is

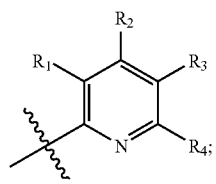

P is $CR_P$; Q is $CR_Q$; S is $CR_S$; T is N; X is $CR_X$; Y is selected from $NR_Y$, O, or S; and $R_P$, $R_Q$, $R_S$, $R_X$, Z, $R_1$, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

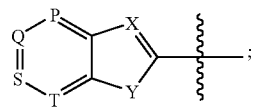

D is

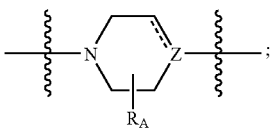

$B_1$ is

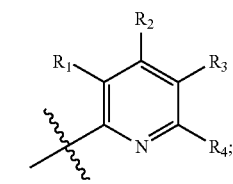

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

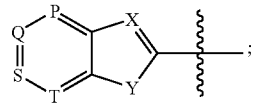

D is

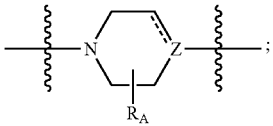

$B_1$ is

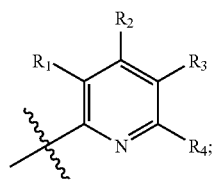

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

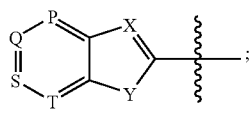

D is

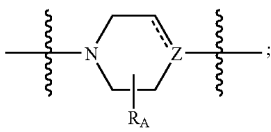

$B_1$ is

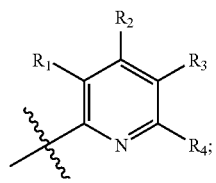

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

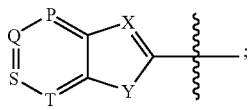

D is

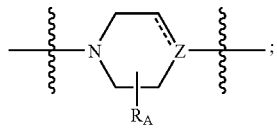

$B_1$ is

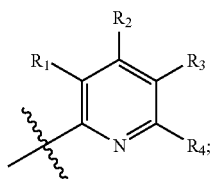

P is N; Q is $CR_Q$; S is $CR_S$; T is $CR_T$; X is $CR_X$; Y is selected from $NR_Y$, O, or S; and $R_Q$, $R_S$, $R_T$, $R_X$, Z, $R_1$, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

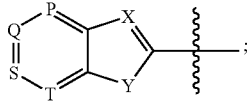

D is

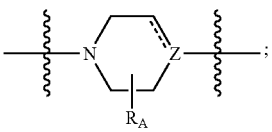

$B_1$ is

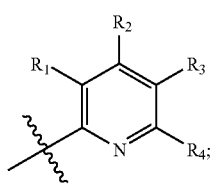

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

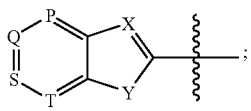

D is

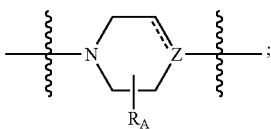

$B_1$ is

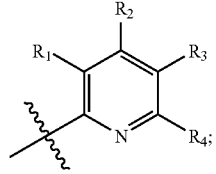

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

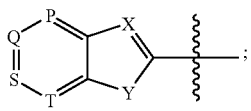

D is

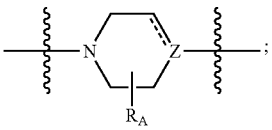

$B_1$ is

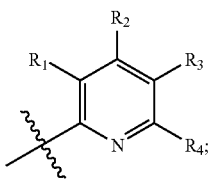

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is D is $B_1$ is p is N; Q is $CR_Q$; S is $CR_S$; T is $CR_T$; X is N; Y is selected from $NR_Y$, O, or S; and $R_Q$, $R_S$, $R_T$, Z, $R_1$, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

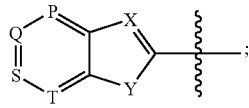

D is

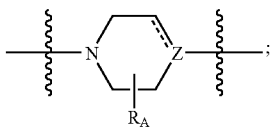

$B_1$ is

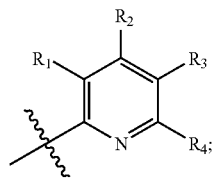

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

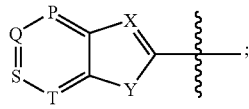

D is

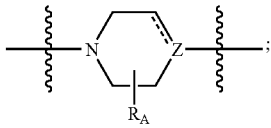

$B_1$ is

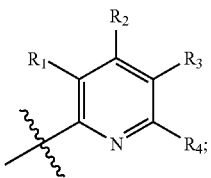

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

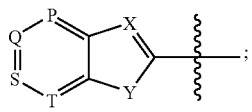

D is

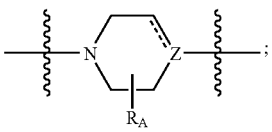

$B_1$ is

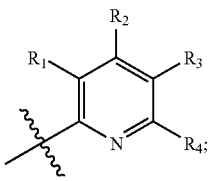

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

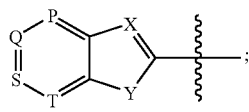

D is

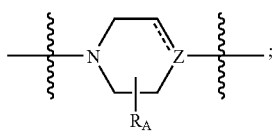

$B_1$ is

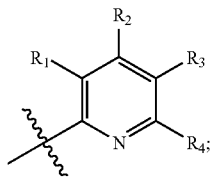

P is $CR_P$; Q is $CR_Q$; S is $CR_S$; T is N; X is N; Y is selected from $NR_Y$, O, or S; and $R_P$, $R_Q$, $R_S$, Z, $R_1$, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

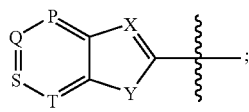

D is

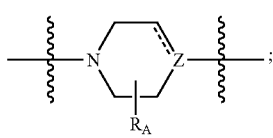

$B_1$ is

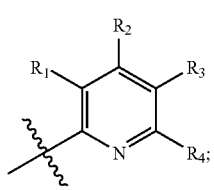

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

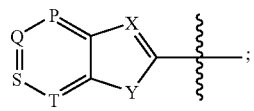

D is

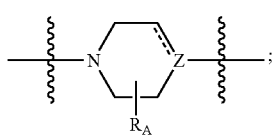

$B_1$ is

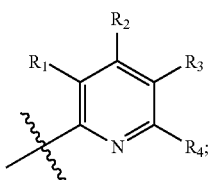

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

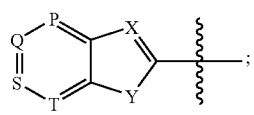

D is

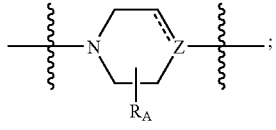

$B_1$ is

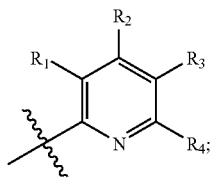

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

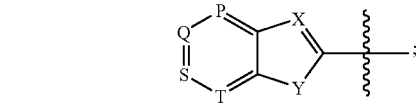

D is

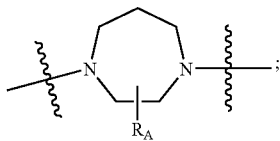

$B_1$ is

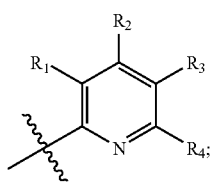

and P, Q, S, T, X, Y, $R_1$, $R_2$, $R_3$, $R_4$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

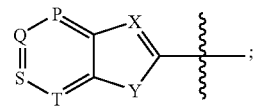

D is

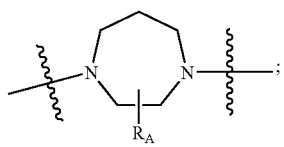

$B_1$ is

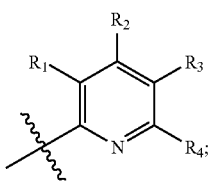

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

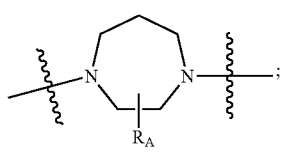

D is

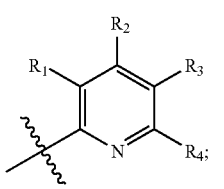

$B_1$ is

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

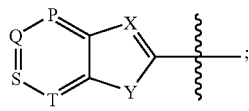

D is

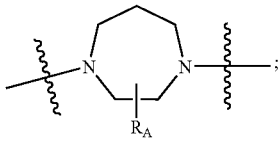

$B_1$ is

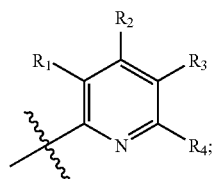

P is $CR_P$; Q is $CR_Q$; S is $CR_S$; T is N; X is $CR_X$; Y is selected from $NR_Y$, O, or S; and $R_P$, $R_Q$, $R_S$, $R_X$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

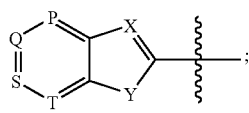

D is

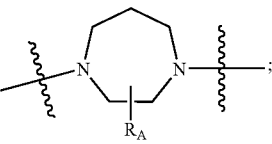

$B_1$ is

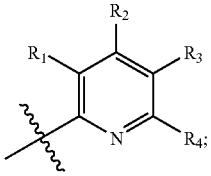

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, and $R_4$ are independently selected from hydrogen, alkoxy, alkyl, alkylthio, cyano, or halogen; and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

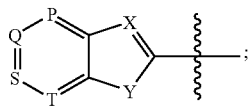

D is

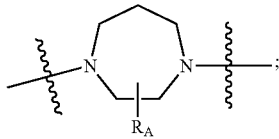

$B_1$ is

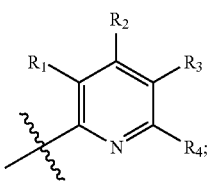

P is N; Q is $CR_Q$; S is $CR_S$; T is $CR_T$; X is $CR_X$; Y is selected from $NR_Y$, O, or S; and $R_Q$, $R_S$, $R_T$, $R_X$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

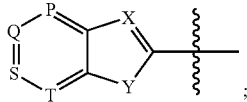

D is

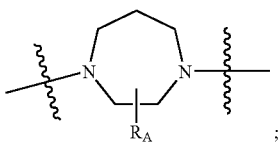

$B_1$ is

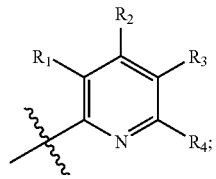

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

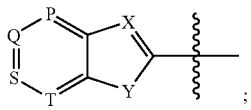

D is

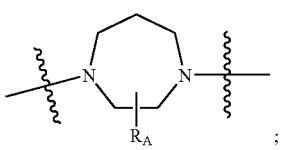

$B_1$ is

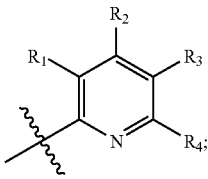

P is N; Q is $CR_Q$; S is $CR_S$; T is $CR_T$; X is N; Y is selected from $NR_Y$, O, or S; and $R_Q$, $R_S$, $R_T$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

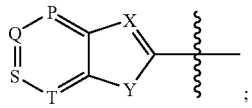

D is

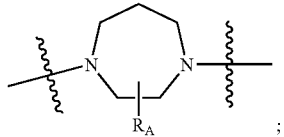

$B_1$ is

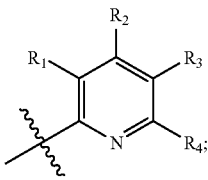

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

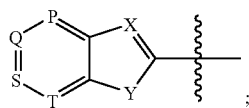

D is

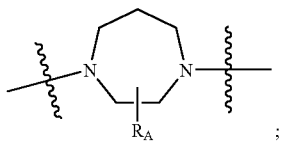

$B_1$ is

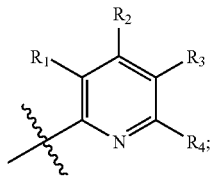

P is $CR_P$; Q is $CR_Q$; S is $CR_S$; T is N; X is N; Y is selected from $NR_Y$, O, or S; and $R_P$, $R_Q$, $R_S$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

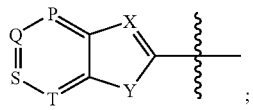

D is

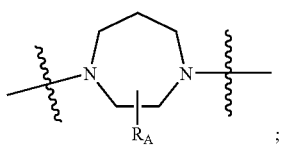

$B_1$ is

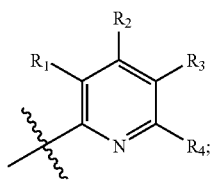

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

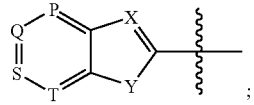

D is

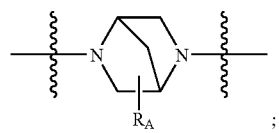

$B_1$ is

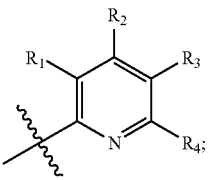

and P, Q, S, T, X, Y, $R_1$, $R_2$, $R_3$, $R_4$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

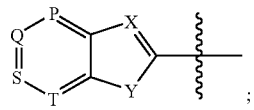

D is

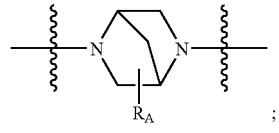

B₁ is

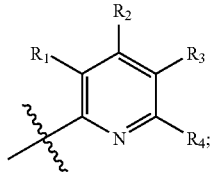

P is CR$_P$; Q is CR$_Q$; S is CR$_S$; T is CR$_T$; X is CR$_X$; Y is selected from NR$_Y$, O, or S; and R$_P$, R$_Q$, R$_S$, R$_T$, R$_X$, R$_1$, R$_2$, R$_3$, R$_4$, R$_Y$, and R$_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

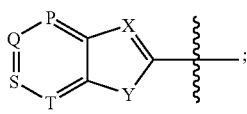

D is

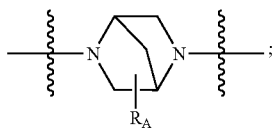

B₁ is

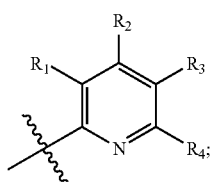

P is CR$_P$; Q is CR$_Q$; S is CR$_S$; T is CR$_T$; X is CR$_X$; R$_P$, R$_Q$, R$_S$, R$_T$, and R$_X$ are independently selected from hydrogen, alkoxy, alkyl, haloalkyl, or halogen; Y is selected from NR$_Y$, O, or S; R$_Y$ is selected from hydrogen or alkyl; R$_1$, R$_2$, R$_3$, and R$_4$ are independently selected from hydrogen, alkoxy, alkyl, alkylthio, cyano, or halogen; and R$_A$ is as defined in formula (I).

In another embodiment, the present invention relates to a method of treating sexual dysfunction in a mammal comprising administering to the manual a therapeutically effective amount of a compound of formula (I) or a pharmaceutically acceptable salt, ester, amide, N-oxide, or prodrug thereof, wherein A is

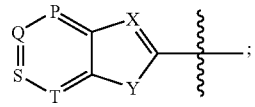

D is

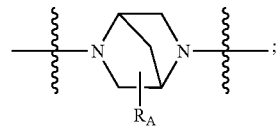

B₁ is

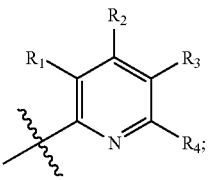

P is CR$_P$; Q is CR$_Q$; S is CR$_S$; T is N; X is CR$_X$; Y is selected from NR$_Y$, O, or S; and R$_P$, R$_Q$, R$_S$, R$_X$, R$_1$, R$_2$, R$_3$, R$_4$, R$_Y$, and R$_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

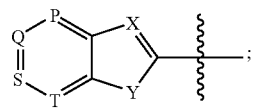

D is

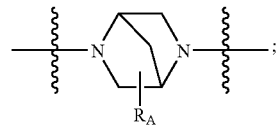

B₁ is

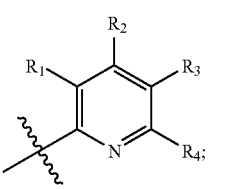

P is CR$_P$; Q is CR$_Q$; S is CR$_S$; T is N; X is CR$_X$; R$_P$, R$_Q$, R$_D$, and R$_X$ are independently selected from hydrogen, alkoxy, alkyl, haloalkyl, or halogen; Y is selected from NR$_Y$, O, or S; R$_Y$ is selected from hydrogen or alkyl; R$_1$, R$_2$, R$_3$, and R$_4$ are independently selected from hydrogen, alkoxy, alkyl, alkylthio, cyano, or halogen; and RA is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

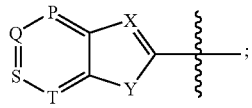

D is

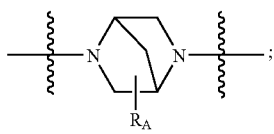

$B_1$ is

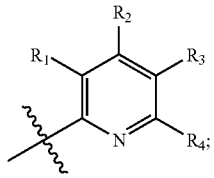

P is N; Q is $CR_Q$; S is $CR_S$; T is $CR_T$; X is $CR_X$; Y is selected from $NR_Y$, O, or S; and $R_Q$, $R_S$, $R_T$, $R_X$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

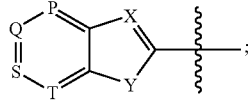

D is

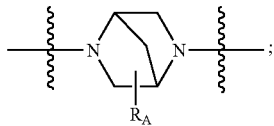

$B_1$ is

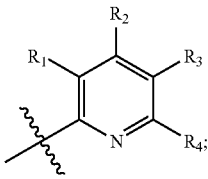

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, and $R_4$ are independently selected from hydrogen, alkoxy, alkyl, alkylthio, cyano, or halogen; and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is D is $B_1$ is P is N; Q is $CR_Q$; S is $CR_S$; T is $CR_T$; X is N; Y is selected from $NR_Y$, O, or S; and $R_Q$, $R_S$, $R_T$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

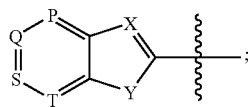

D is

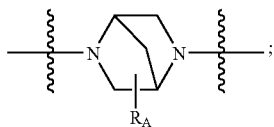

$B_1$ is

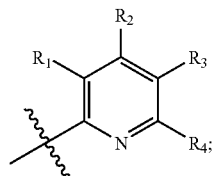

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; $R_1$, $R_2$, $R_3$, and $R_4$ are independently selected from hydrogen, alkoxy, alkyl, alkylthio, cyano, or halogen; and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

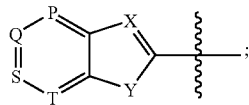

D is

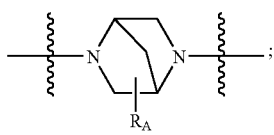

$B_1$ is

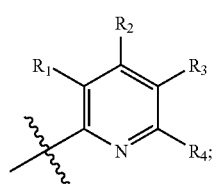

P is $CR_P$; Q is $CR_Q$; S is $CR_S$; T is N; X is N; Y is selected from $NR_Y$, O, or S; and $R_P$, $R_Q$, $R_S$, $R_1$, $R_2$, $R_3$, $R_4$, $R_Y$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

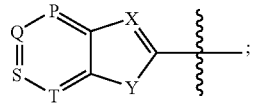

D is

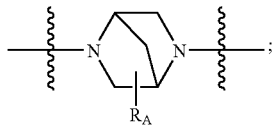

$B_1$ is

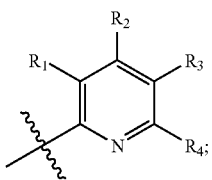

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; $R_1$, $R_2$, $R_3$, and $R_4$ are independently selected from hydrogen, alkoxy, alkyl, alkylthio, cyano, or halogen; and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

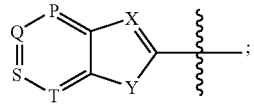

D is

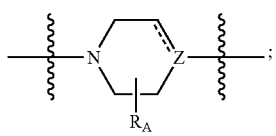

$B_1$ is

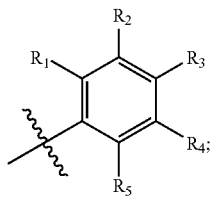

and P, Q, S, T, X, Y, Z, $R_1$, $R_2$, $R_3$, $R_4$, $R_5$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

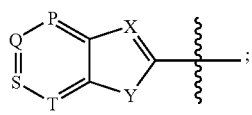

D is

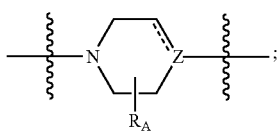

$B_1$ is

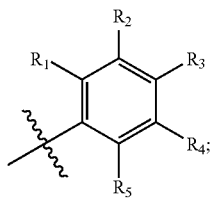

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, Z, $R_1$, $R_2$, $R_3$, $R_4$, $R_5$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

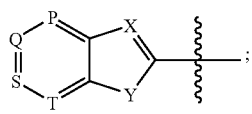

D is

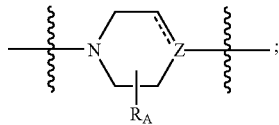

$B_1$ is

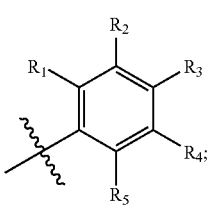

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

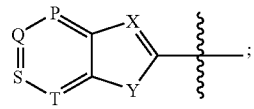

D is

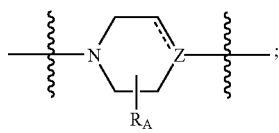

$B_1$ is

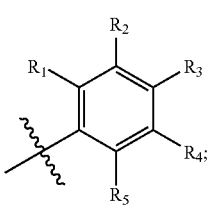

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from NR$_Y$, O, or S; R$_Y$ is selected from hydrogen or alkyl; Z is CH; --- is absent; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

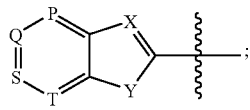

D is

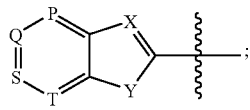

B$_1$ is

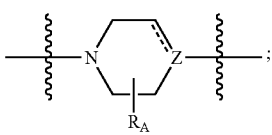

P is CR$_P$; Q is CR$_Q$; S is CR$_S$; T is CR$_T$; X is CR$_X$; R$_P$, R$_Q$, R$_S$, R$_T$, and R$_X$ are independently selected from hydrogen, alkoxy, alkyl, haloalkyl, or halogen; Y is selected from NR$_Y$, O, or S; R$_Y$ is selected from hydrogen or alkyl; Z is C; --- is a bond; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

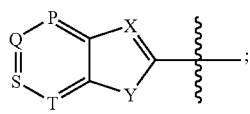

D is

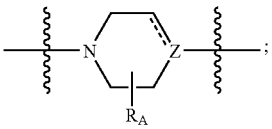

B$_1$ is

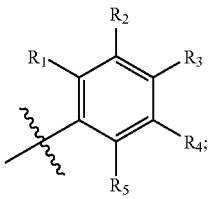

P is CR$_P$; Q is CR$_Q$; S is CR$_S$; T is N; X is CR$_X$; Y is selected from NR$_Y$, O, or S; and R$_P$, R$_Q$, R$_S$, R$_X$, Z, R$_1$, R$_2$, R$_3$, R$_4$, R$_5$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

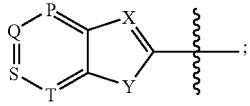

D is

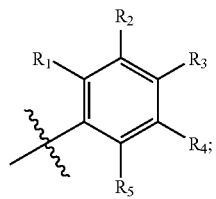

B$_1$ is

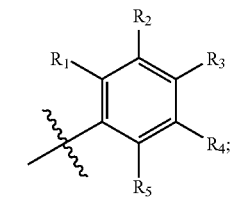

P is CR$_P$; Q is CR$_Q$; S is CR$_S$; T is N; X is CR$_X$; R$_P$, R$_Q$, R$_S$, and R$_X$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

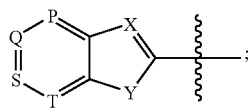

D is

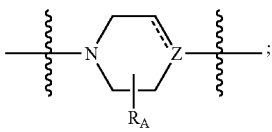

$B_1$ is

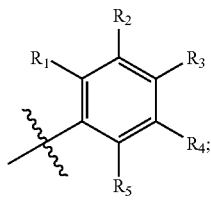

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

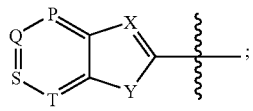

D is

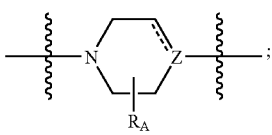

$B_1$ is

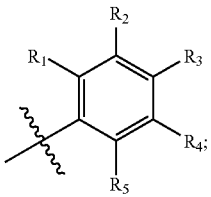

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

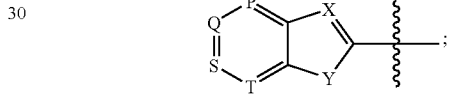

D is

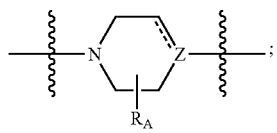

$B_1$ is

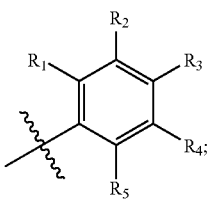

P is N; Q is $CR_Q$; S is $CR_S$; T is $CR_T$; X is $CR_X$; Y is selected from $NR_Y$, O, or S; and $R_Q$, $R_S$, $R_T$, $R_X$, Z, $R_1$, $R_2$, $R_3$, $R_4$, $R_5$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is D is

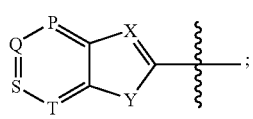

B₁ is

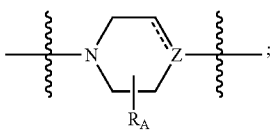

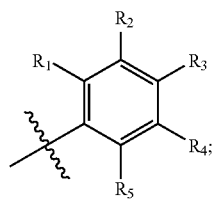

P is N; Q is CR_Q; S is CR_S; T is CR_T; X is CR_X; R_Q, R_S, R_T, and R_X are independently selected from hydrogen, alkoxy, alkyl, haloalkyl, or halogen; Y is selected from NR_Y, O, or S; R_Y is selected from hydrogen or alkyl; Z is N; --- is absent; and R_1, R_2, R_3, R_4, and R_5 are independently selected from hydrogen, alkoxy, alkyl, alkylthio, cyano, halogen, or hydroxy; and R_A is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

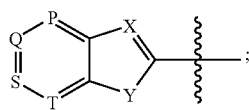

D is

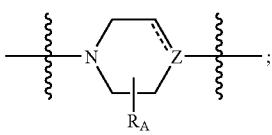

B₁ is

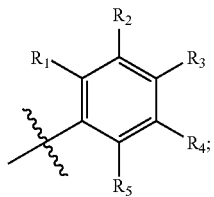

P is N; Q is CR_Q; S is CR_S; T is CR_T; X is CR_X; R_Q, R_S, R_T, and R_X are independently selected from hydrogen, alkoxy, alkyl, haloalkyl, or halogen; Y is selected from NR_Y, O, or S; R_Y is selected from hydrogen or alkyl; Z is CH; --- is absent; R_1, R_2, R_3, R_4, and R_5 are independently selected from hydrogen, alkoxy, alkyl, alkylthio, cyano, halogen, or hydroxy; and R_A is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

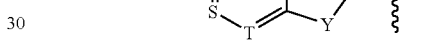

D is

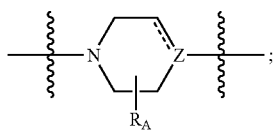

B₁ is

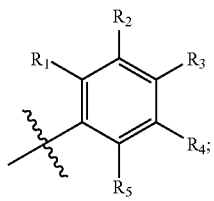

P is N; Q is CR_Q; S is CR_S; T is CR_T; X is CR_X; R_Q, R_S, R_T, and R_X are independently selected from hydrogen, alkoxy, alkyl, haloalkyl, or halogen; Y is selected from NR_Y, O, or S; R_Y is selected from hydrogen or alkyl; Z is C; --- is a bond; R_1, R_2, R_3, R_4, and R_5 are independently selected from hydrogen, alkoxy, alkyl, alkylthio, cyano, halogen, or hydroxy; and R_A is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

41

D is

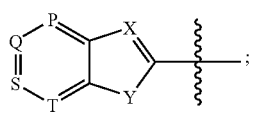

B₁ is

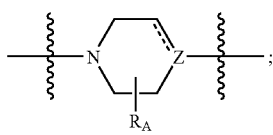

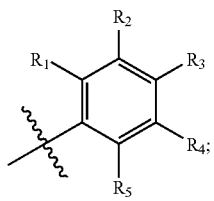

P is N; Q is CR$_Q$; S is CR$_S$; T is CR$_T$; X is N; Y is selected from NR$_Y$, O, or S; and R$_Q$, R$_S$, R$_T$, Z, R$_1$, R$_2$, R$_3$, R$_4$, R$_5$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

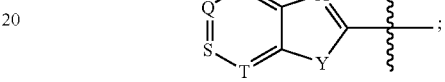

D is

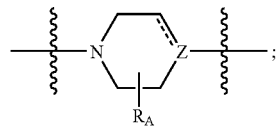

B₁ is

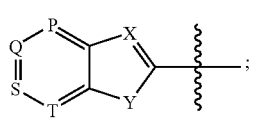

42

P is N; Q is CR$_Q$; S is CR$_S$; T is CR$_T$; X is N; R$_Q$, R$_S$, and R$_T$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

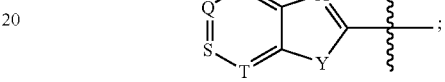

D is

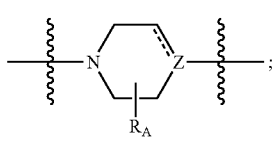

B₁ is

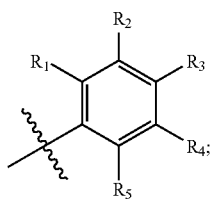

P is N; Q is CR$_Q$; S is CR$_S$; T is CR$_T$; X is N; R$_Q$, R$_S$, and R$_T$ are independently selected from hydrogen, alkoxy, alkyl, haloalkyl, or halogen; Y is selected from NR$_Y$, O, or S; R$_Y$ is selected from hydrogen or alkyl; Z is CH; --- is absent; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is D is

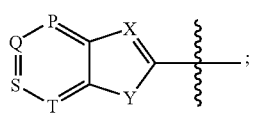

B₁ is

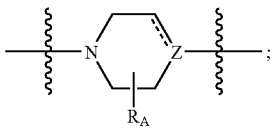

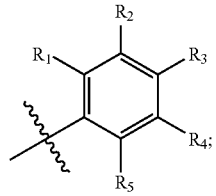

P is N; Q is CR$_Q$; S is CR$_S$; T is CR$_T$; X is N; R$_Q$, R$_S$, and R$_T$ are independently selected from hydrogen, alkoxy, alkyl, haloalkyl, or halogen; Y is selected from NR$_Y$, O, or S; R$_Y$ is selected from hydrogen or alkyl; Z is C; --- is a bond; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

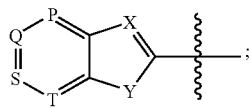

D is

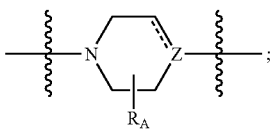

B₁ is

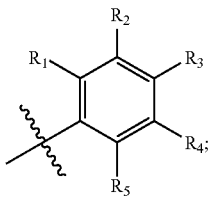

P is CR$_P$; Q is CR$_Q$; S is CR$_S$; T is N; X is N; Y is selected from NR$_Y$, O, or S; and R$_P$, R$_Q$, R$_S$, Z, R$_1$, R$_2$, R$_3$, R$_4$, R$_5$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

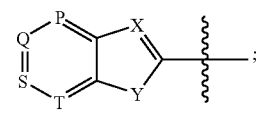

D is

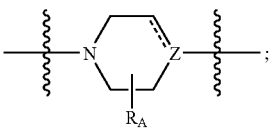

B₁ is

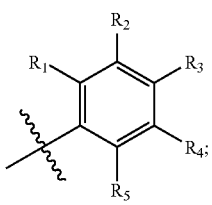

P is CR$_P$; Q is CR$_Q$; S is CR$_S$; T is N; X is N; Y is selected from NR$_Y$, O, or S; R$_Y$ is selected from hydrogen or alkyl; R$_P$, R$_Q$, and R$_S$ are independently selected from hydrogen, alkoxy, alkyl, haloalkyl, or halogen; Z is N; --- is absent; R$_1$, R$_2$, R$_3$, R$_4$, and R$_5$ are independently selected from hydrogen, alkoxy, alkyl, alkylthio, cyano, halogen, or hydroxy; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

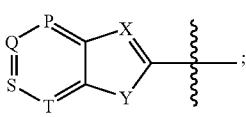

D is

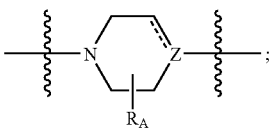

B₁ is

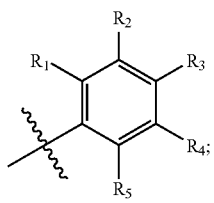

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is CH; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

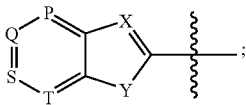

D is

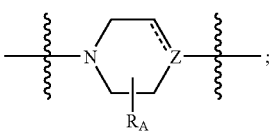

B₁ is

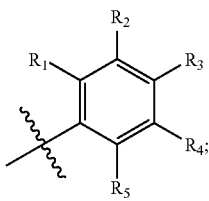

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is C; --- is a bond; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

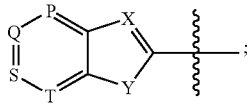

D is

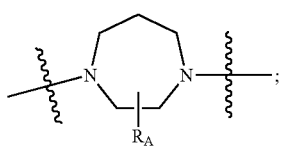

B₁ is

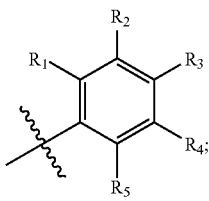

and P, Q, S, T, X, Y, $R_1$, $R_2$, $R_3$, $R_4$, $R_5$, and $R_A$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

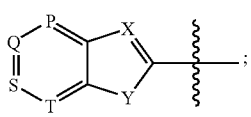

D is

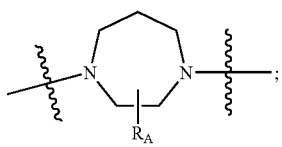

$B_1$ is

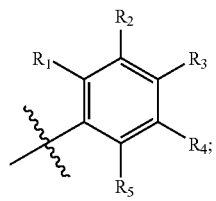

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, $R_1$, $R_2$, $R_3$, $R_4$, $R_5$, $R_A$, and $R_Y$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

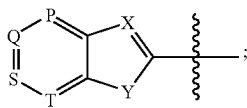

D is

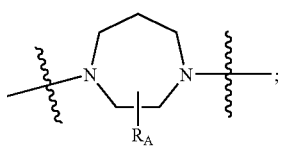

$B_1$ is

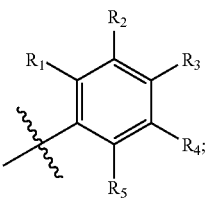

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

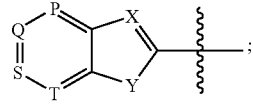

D is

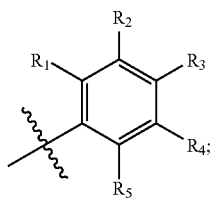

$B_1$ is

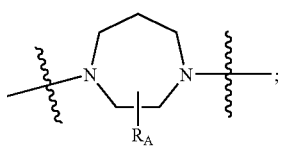

P is $CR_P$; Q is $CR_Q$; S is $CR_S$; T is N; X is $CR_X$; Y is selected from $NR_Y$, O, or S; and $R_P$, $R_Q$, $R_S$, $R_X$, $R_1$, $R_2$, $R_3$, $R_4$, $R_5$, $R_A$, and $R_Y$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

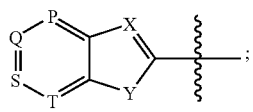

D is

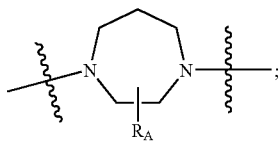

$B_1$ is

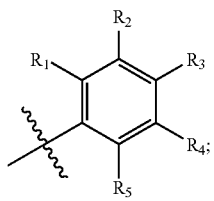

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

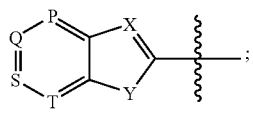

D is

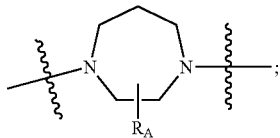

$B_1$ is

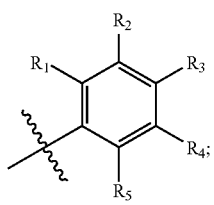

P is N; Q is $CR_Q$; S is $CR_S$; T is $CR_T$; X is $CR_X$; Y is selected from $NR_Y$, O, or S; and $R_Q$, $R_S$, $R_T$, $R_X$, $R_1$, $R_2$, $R_3$, $R_4$, $R_5$, $R_A$, and $R_Y$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

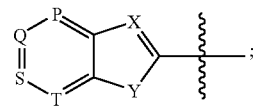

D is

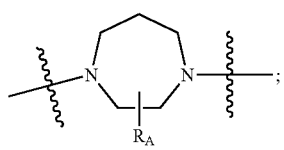

$B_1$ is

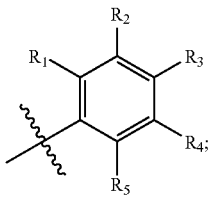

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

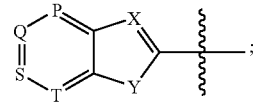

D is

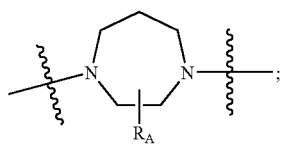

$B_1$ is

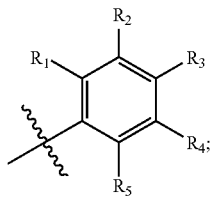

P is N; Q is $CR_Q$; S is $CR_S$; T is $CR_T$; X is N; Y is selected from $NR_Y$, O, or S; and $R_Q$, $R_S$, $R_T$, $R_1$, $R_2$, $R_3$, $R_4$, $R_5$, $R_A$, and $R_Y$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

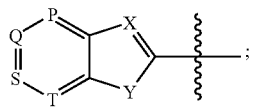

D is

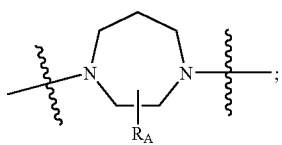

$B_1$ is

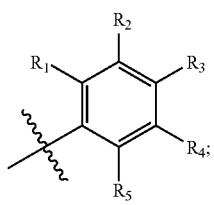

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

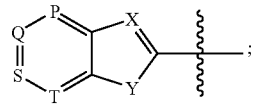

D is

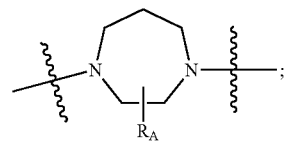

$B_1$ is

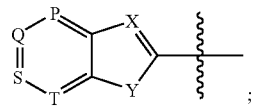

P is $CR_P$; Q is $CR_Q$; S is $CR_S$; T is N; X is N; Y is selected from $NR_Y$, O, or S; and $R_P$, $R_Q$, $R_S$, $R_1$, $R_2$, $R_3$, $R_4$, $R_5$, $R_A$, and $R_Y$ are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

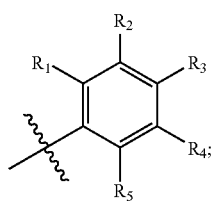

D is

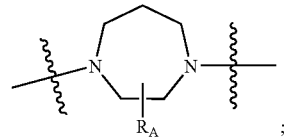

$B_1$ is

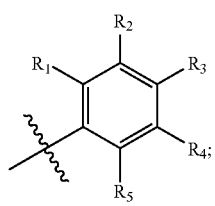

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

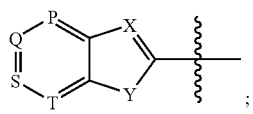

D is

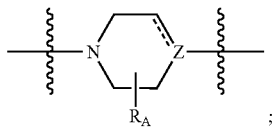

$B_1$ is

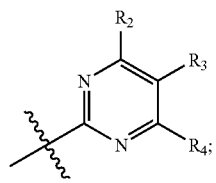

and P, Q, S, T, X, Y, Z, $R_2$, $R_3$, $R_4$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof wherein A is

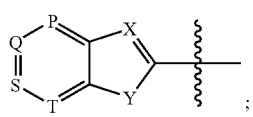

D is

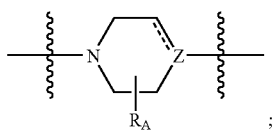

$B_1$ is

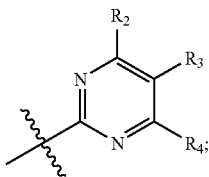

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, Z, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

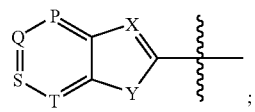

D is

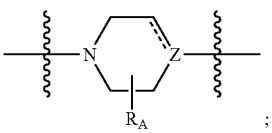

$B_1$ is

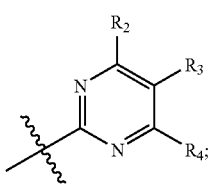

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_2$, $R_3$, and $R_4$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

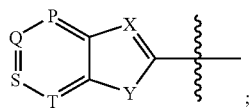

D is

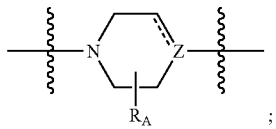

B$_1$ is

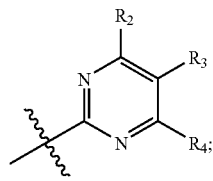

P is CR$_P$; Q is CR$_Q$; S is CR$_S$; T is N; X is CR$_X$; Y is selected from NR$_Y$, O, or S; and R$_P$, R$_Q$, R$_S$, R$_X$, Z, R$_2$, R$_3$, R$_4$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

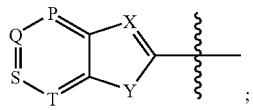

D is

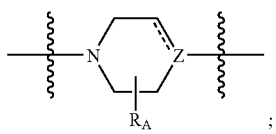

B$_1$ is

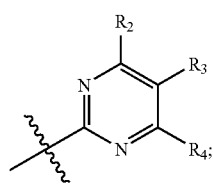

P is CR$_P$; Q is CR$_Q$; S is CR$_S$; T is N; X is CR$_X$; R$_P$, R$_Q$, R$_S$, and R$_X$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_2$, R$_3$, and R$_4$ are independently selected from hydrogen, alkyl, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

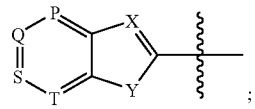

D is

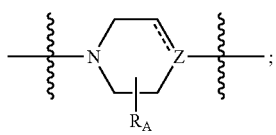

B$_1$ is

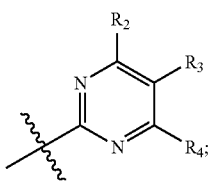

P is N; Q is CR$_Q$; S is CR$_S$; T is CR$_T$; X is CR$_X$; Y is selected from NR$_Y$, O, or S; and R$_Q$, R$_S$, R$_T$, R$_X$, Z, R$_2$, R$_3$, R$_4$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

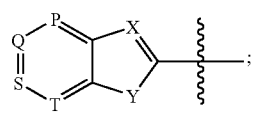

D is

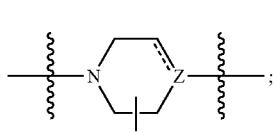

B$_1$ is

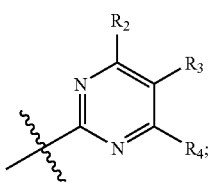

P is N; Q is CR$_Q$; S is CR$_S$; T is CR$_T$; X is CR$_X$; R$_Q$, R$_S$, R$_T$, and R$_X$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_2$, R$_3$, and R$_4$ are independently selected from hydrogen, alkyl, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

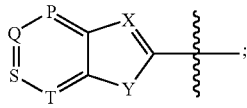

D is

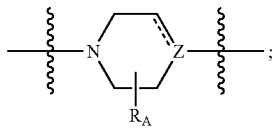

B$_1$ is

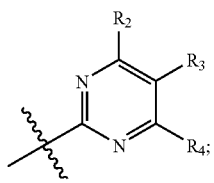

P is N; Q is CR$_Q$; S is CR$_S$; T is CR$_T$; X is N; Y is selected from NR$_Y$, O, or S; and R$_Q$, R$_S$, R$_T$, Z, R$_2$, R$_3$, R$_4$, R$_A$, R$_Y$, and --- are as defined in formula (I).

In another embodiment, the present invention relates to a method of treating sexual d y s f u n c t i o n in a mammal comprising administering to the mammal a therapeutically effective amount of a compound of formula (I) or a pharmaceutically acceptable salt, ester, amide, N-oxide, or prodrug thereof, wherein A is

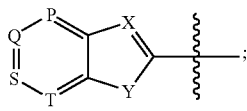

D is

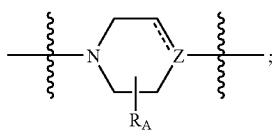

B$_1$ is

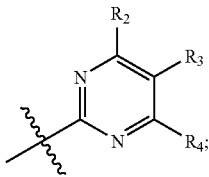

P is N; Q is CR$_Q$; S is CR$_S$; T is CR$_T$; X is N; Y is selected from NR$_Y$, O, or S; R$_Y$ is selected from hydrogen or alkyl; R$_Q$, R$_S$, and R$_T$ are independently selected from hydrogen, alkoxy, alkyl, haloalkyl, or halogen; Z is N; --- is absent; R$_2$, R$_3$, and R$_4$ are independently selected from hydrogen, alkyl, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

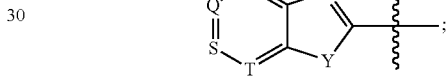

D is

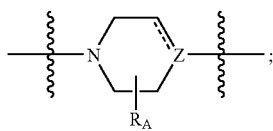

B$_1$ is

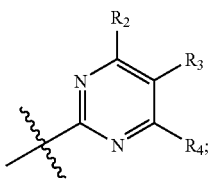

P is CR$_P$; Q is CR$_Q$; S is CR$_S$; T is N; X is N; Y is selected from NR$_Y$, O, or S; and R$_P$, R$_Q$, R$_S$, Z, R$_2$, R$_3$, R$_4$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

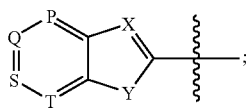

D is

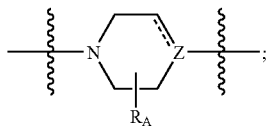

B₁ is

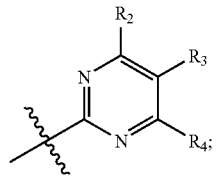

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; Z is N; --- is absent; $R_2$, $R_3$, and $R_4$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

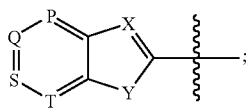

D is

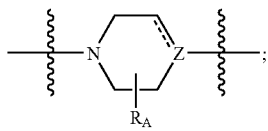

B₁ is

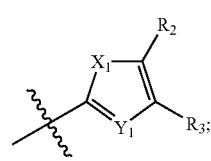

and P, Q, S, T, X, Y, Z, $X_1$, $Y_1$, $R_2$, $R_3$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

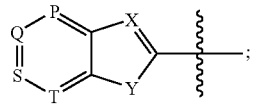

D is

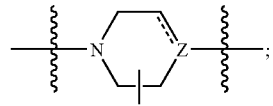

B₁ is

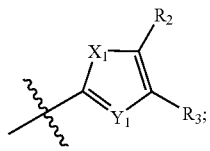

P is $CR_P$; Q is $CR_Q$; S is $CR_S$; T is $CR_T$; X is $CR_X$; Y is selected from $NR_Y$, O, or S; and $R_P$, $R_Q$, $R_S$, $R_T$, $R_X$, Z, $X_1$, $Y_1$, $R_2$, $R_3$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

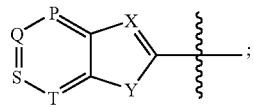

D is

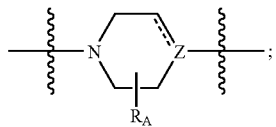

B₁ is

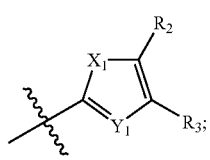

P is $CR_P$; Q is $CR_Q$; S is $CR_S$; T is $CR_T$; X is $CR_X$; $R_P$, $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $X_1$ is S; $Y_1$ is N; Z is N; --- is absent; $R_2$ and $R_3$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

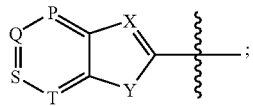

D is

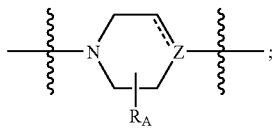

$B_1$ is

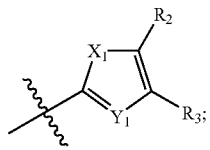

P is $CR_P$; Q is $CR_Q$; S is $CR_S$; T is N; X is $CR_X$; Y is selected from $NR_Y$, O, or S; and $R_P$, $R_Q$, $R_S$, $R_X$, Z, $X_1$, $Y_1$, $R_2$, $R_3$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

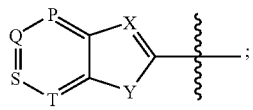

D is

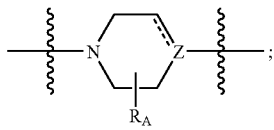

$B_1$ is

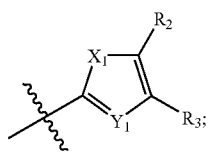

P is $CR_P$; Q is $CR_Q$; S is $CR_S$; T is N; X is $CR_X$; $R_P$, $R_Q$, $R_S$, and $R_X$ are independently selected from hydrogen, alkoxy, alkyl, haloalkyl, or halogen; Y is selected from $NR_Y$, O, or S; $X_1$ is S; $Y_1$ is N; $R_Y$ is selected from hydrogen or alkyl; Z is N; --- is absent; $R_2$ and $R_3$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

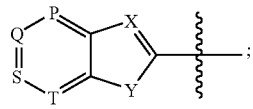

D is

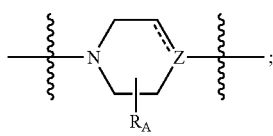

$B_1$ is

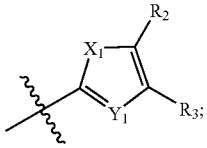

P is N; Q is $CR_Q$; S is $CR_S$; T is $CR_T$; X is $CR_X$; Y is selected from $NR_Y$, O, or S; and $R_Q$, $R_S$, $R_T$, $R_X$, Z, $X_1$, $Y_1$, $R_2$, $R_3$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

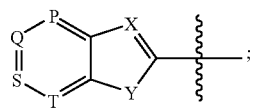

D is

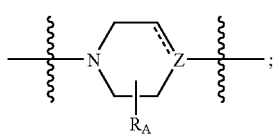

$B_1$ is

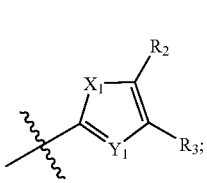

P is N; Q is $CR_Q$; S is $CR_S$; T is $CR_T$; X is $CR_X$; $R_Q$, $R_S$, $R_T$, and $R_X$ are independently selected from hydrogen, alkoxy, alkyl, haloalkyl, or halogen; Y is selected from $NR_Y$, O, or S; $R_Y$ is selected from hydrogen or alkyl; $X_1$ is S; $Y_1$ is N; Z is N; --- is absent; $R_2$ and $R_3$ are independently selected from hydrogen, alkyl, or halogen; and $R_4$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

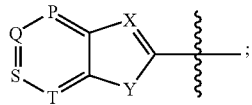

D is

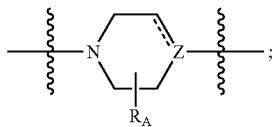

$B_1$ is

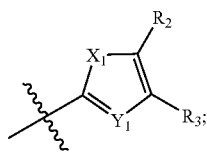

P is N; Q is $CR_Q$; S is $CR_S$; T is $CR_T$; X is N; Y is selected from $NR_Y$, O, or S; and $R_Q$, $R_S$, $R_T$, Z, $X_1$, $Y_1$, $R_2$, $R_3$, $R_4$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

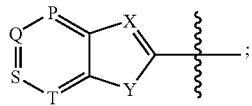

D is

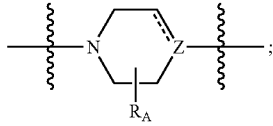

$B_1$ is

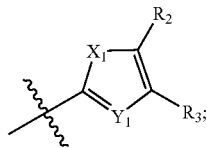

P is N; Q is $CR_Q$; S is $CR_S$; T is $CR_T$; X is N; Y is selected from $NR_Y$, O, or S; $R_Y$ is selected from hydrogen or alkyl; $R_Q$, $R_S$, and $R_T$ are independently selected from hydrogen, alkoxy, alkyl, haloalkyl, or halogen; $X_1$ is S; $Y_1$ is N; Z is N; --- is absent; $R_2$ and $R_3$ are independently selected from hydrogen, alkyl, or halogen; and $R_4$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

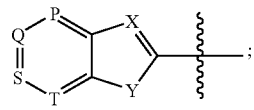

D is

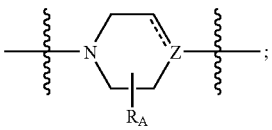

$B_1$ is

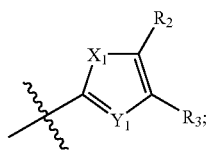

P is N; Q is $CR_Q$; S is $CR_S$; T is N; X is N; Y is selected from $NR_Y$, O, or S; and $R_P$, $R_Q$, $R_S$, Z, $X_1$, $Y_1$, $R_2$, $R_3$, $R_4$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

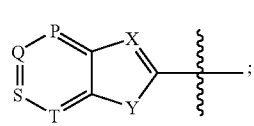

D is

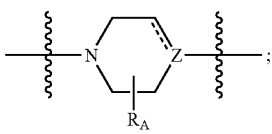

$B_1$ is

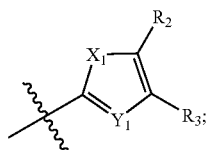

P is $CR_P$; Q is $CR_Q$; S is $CR_S$; T is N; X is N; Y is selected from $NR_Y$, O, or S; $R_Y$ is selected from hydrogen or alkyl; $R_P$, $R_Q$, and $R_S$ are independently selected from hydrogen, alkoxy, alkyl, haloalkyl, or halogen; $X_1$ is S; $Y_1$ is N; Z is N; --- is absent; $R_2$ and $R_3$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

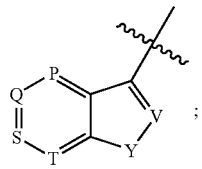

D is

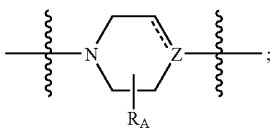

$B_1$ is

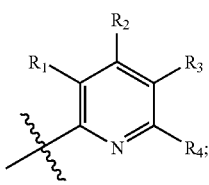

and P, Q, S, T, V, Y, Z, $R_P$, $R_2$, $R_3$, $R_4$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

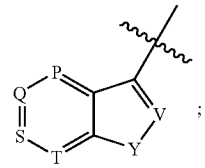

D is

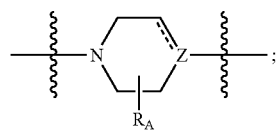

$B_1$ is

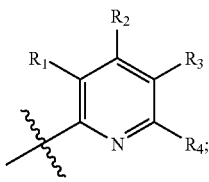

P is $CR_P$; Q is $CR_Q$; S is $CR_S$; T is $CR_T$; V is $CR_V$; Y is selected from $NR_Y$, O, or S; and $R_P$, $R_Q$, $R_S$, $R_T$, $R_V$, Z. $R_1$, $R_2$, $R_3$, $P_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

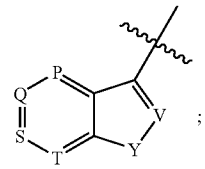

D is

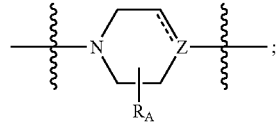

$B_1$ is

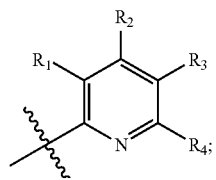

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

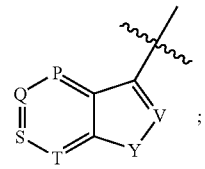

D is

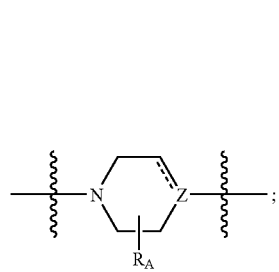

$B_1$ is

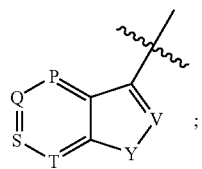

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

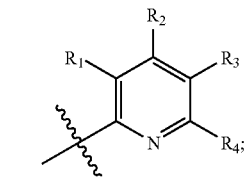

D is

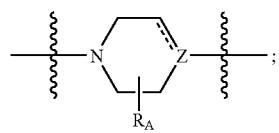

$B_1$ is

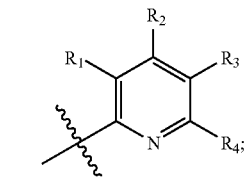

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

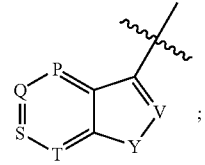

D is

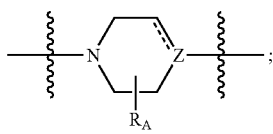

B₁ is

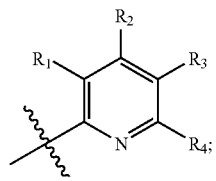

P is CR$_P$; Q is CR$_Q$; S is CR$_S$; T is N; V is CR$_V$; Y is selected from NR$_Y$, O, or S; and R$_P$, R$_Q$, R$_S$, R$_V$, Z, R$_1$, R$_2$, R$_3$, R$_4$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

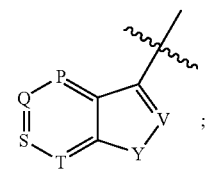

D is

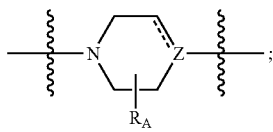

B₁ is

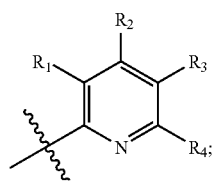

P is CR$_P$; Q is CR$_Q$; S is CR$_S$; T is N; V is CR$_V$; R$_P$, R$_Q$, R$_S$, and R$_V$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_1$, R$_2$, R$_3$, and R$_4$ are independently selected from hydrogen, alkoxy, alkyl, alkylthio, cyano, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

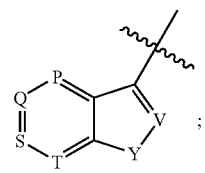

D is

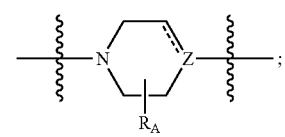

B₁ is

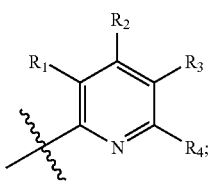

P is CR$_P$; Q is CR$_Q$; S is CR$_S$; T is N; V is CR$_V$; R$_P$, R$_Q$, R$_S$, and R$_V$ are independently selected from hydrogen, alkoxy, alkyl, haloalkyl, or halogen; Y is selected from NR$_Y$, O, or S; R$_Y$ is selected from hydrogen or alkyl; Z is CH; --- is absent; R$_1$, R$_2$, R$_3$, and R$_4$ are independently selected from hydrogen, alkoxy, alkyl, alkylthio, cyano, or halogen; and R$_A$ is as defined in formula (I).

In another embodiment, the present invention relates to a method of treating sexual dysfunction in a manual comprising administering to the mammal a therapeutically effective amount of a compound of formula (I) or a pharmaceutically acceptable salt, ester, amide, N-oxide, or prodrug thereof, wherein A is

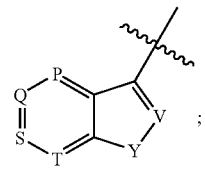

D is

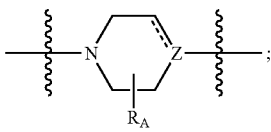

B₁ is

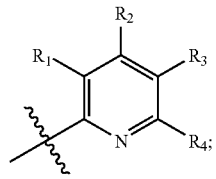

P is CR$_P$; Q is CR$_Q$; S is CR$_S$; T is N; V is CR$_V$; R$_P$, R$_Q$, R$_S$, and R$_V$ are independently selected from hydrogen, alkoxy, alkyl, haloalkyl, or halogen; Y is selected from NR$_Y$, O, or S; R$_Y$ is selected from hydrogen or alkyl; Z is C; --- is a bond; R$_1$, R$_2$, R$_3$, and R$_4$ are independently selected from hydrogen, alkoxy, alkyl, alkylthio, cyano, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

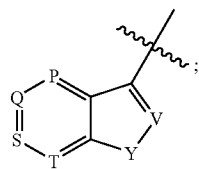

D is

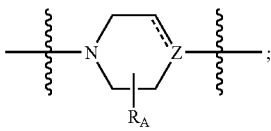

B₁ is

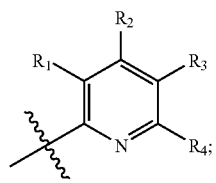

P is N; Q is CR$_Q$; S is CR$_S$; T is CR$_T$; V is CR$_V$; Y is selected from NR$_Y$, O., or S; and R$_Q$, R$_S$, R$_T$, R$_V$, Z, R$_1$, R$_2$, R$_3$, R$_4$, R$_A$, R$_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

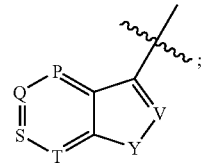

D is

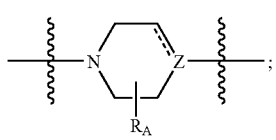

B₁ is

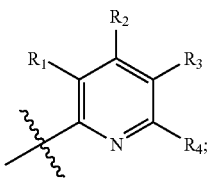

P is N; Q is CR$_Q$; S is CR$_S$; T is CR$_T$; V is CR$_V$; R$_Q$, R$_S$, R$_T$ and R$_V$ are independently selected from hydrogen, alkoxy, alkyl, haloalkyl, or halogen; Y is selected from NR$_Y$, O, or S; R$_Y$ is selected from hydrogen or alkyl; Z is N; --- is absent; R$_1$, R$_2$, R$_3$, and R$_4$ are independently selected from hydrogen, alkoxy, alkyl, alkylthio, cyano, or halogen; and R$_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

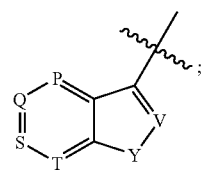

D is

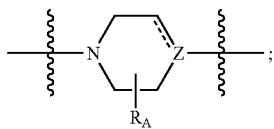

$B_1$ is

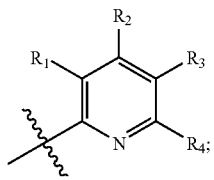

P is N; Q is $CR_Q$; S is $CR_S$; T is $CR_T$; V is $CR_V$; $R_Q$, $R_S$, $R_T$ and $R_V$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

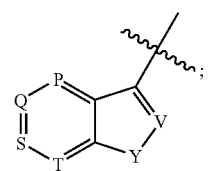

D is

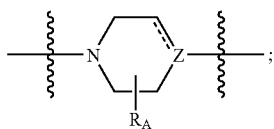

$B_1$ is

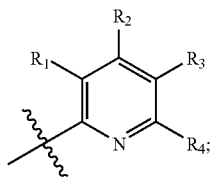

P is N; Q is $CR_Q$; S is $CR_S$; T is $CR_T$; V is $CR_V$; $R_Q$, $R_S$, $R_T$ and $R_V$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

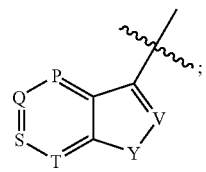

D is

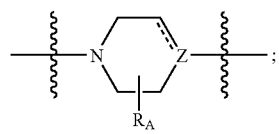

$B_1$ is

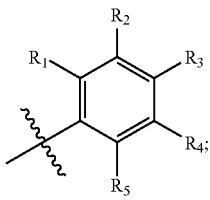

and P, Q, S, T, V, Y, Z, $R_1$, $R_2$, $R_3$, $R_4$, $R_5$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

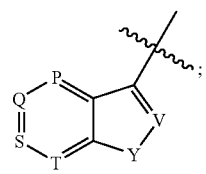

D is

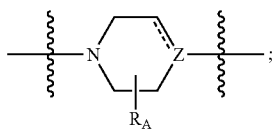

$B_1$ is

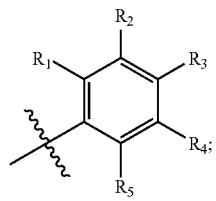

P is $CR_P$; Q is $CR_Q$; S is $CR_S$; T is $CR_T$; V is $CR_V$; Y is selected from $NR_Y$, O, or S; and $R_P$, $R_Q$, $R_S$, $R_T$, $R_V$, Z, $R_1$, $R_2$, $R_3$, $R_5$, $R_4$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

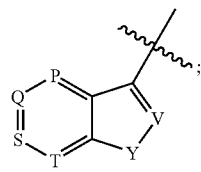

D is

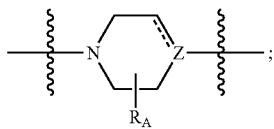

$B_1$ is

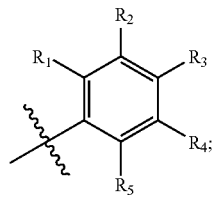

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

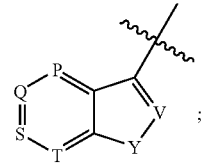

D is

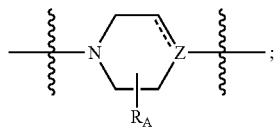

$B_1$ is

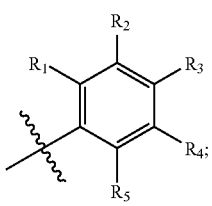

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

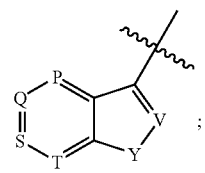

D is

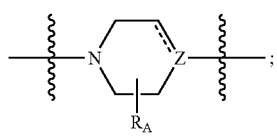

$B_1$ is

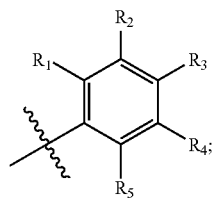

P is $CR_P$; Q is $CR_Q$; S is $CR_S$; T is $CR_T$; V is $CR_V$; $R_P$, $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

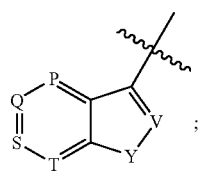

D is

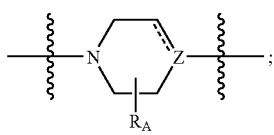

$B_1$ is

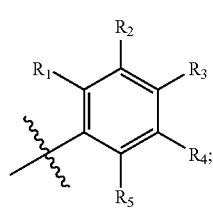

P is $CR_P$; Q is $CR_Q$; S is $CR_S$; T is N; V is $CR_V$; Y is selected from $NR_Y$, O, or S; and $R_P$, $R_Q$, $R_S$, $R_V$, Z, $R_1$, $R_2$, $R_3$, $R_4$, $R_5$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

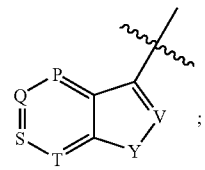

D is

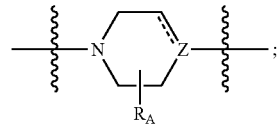

$B_1$ is

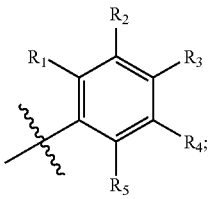

P is $CR_P$; Q is $CR_Q$; S is $CR_S$; T is N; V is $CR_V$; $R_P$, $R_Q$, $R_S$, and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

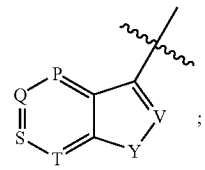

D is

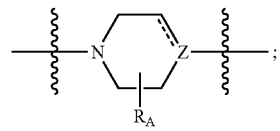

$B_1$ is

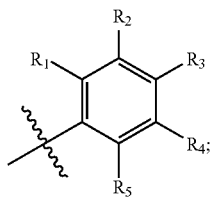

P is $CR_P$; Q is $CR_Q$; S is $CR_S$; T is N; V is $CR_V$; $R_P$, $R_Q$, $R_S$, and $R_V$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

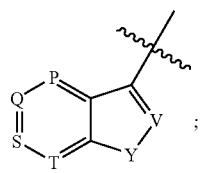

D is

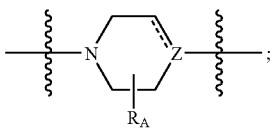

$B_1$ is

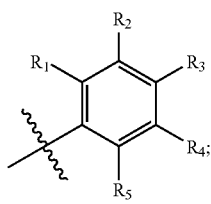

P is $CR_P$; Q is $CR_Q$; S is $CR_S$; T is N; V is $CR_V$; $R_P$, $R_Q$, $R_S$, and $R_V$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

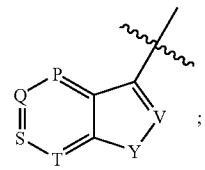

D is

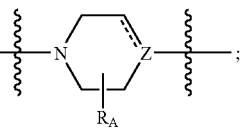

$B_1$ is

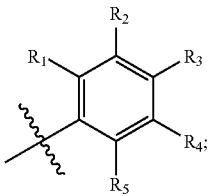

P is N; Q is $CR_Q$; S is $CR_S$; T is $CR_T$; V is $CR_V$; Y is selected from $NR_Y$, O, or S; and $R_Q$, $R_S$, $R_T$, $R_V$, Z, $R_1$, $R_2$, $R_3$, $R_4$, $R_5$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

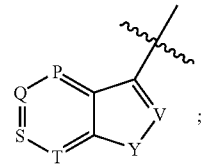

D is

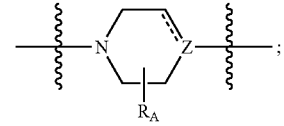

$B_1$ is

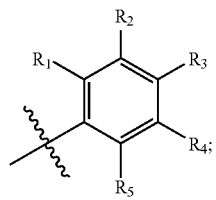

P is N; Q is $CR_Q$; S is $CR_S$; T is $CR_T$; V is $CR_V$; $R_Q$, $R_S$, $R_T$ and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

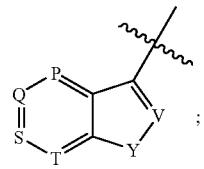

D is

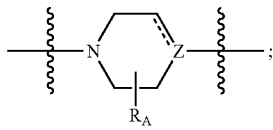

$B_1$ is

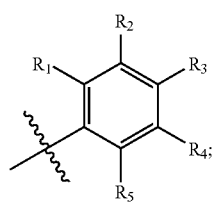

P is N; Q is $CR_Q$; S is $CR_S$; T is $CR_T$; V is $CR_V$; $R_Q$, $R_S$, $R_T$ and $R_V$ are independently selected from hydrogen, alkoxy, alkyl, haloalkyl, or halogen; Y is selected from $NR_Y$, O, or S; $R_Y$ is selected from hydrogen or alkyl; Z is CH; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

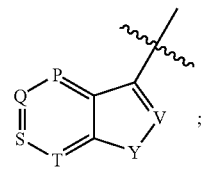

D is

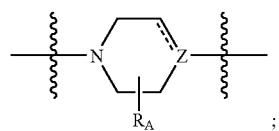

$B_1$ is

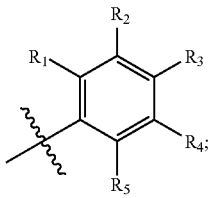

P is N; Q is $CR_Q$; S is $CR_S$; T is $CR_T$; V is $CR_V$; $R_Q$, $R_S$, $R_T$ and $R_V$ are independently selected from hydrogen, alkoxy, alkyl, haloalkyl, or halogen; Y is selected from $NR_Y$, O, or S; $R_Y$ is selected from hydrogen or alkyl; Z is C; --- is a bond; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

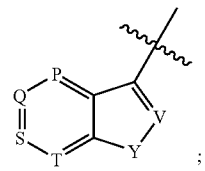

D is

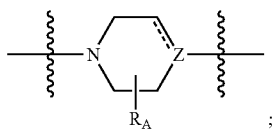
;

B₁ is

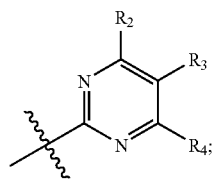

and P, Q, S, T, V, Y, Z, R₂, R₃, R₄, R_A, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

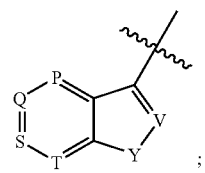
;

D is

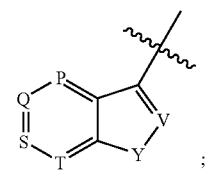
;

B₁ is

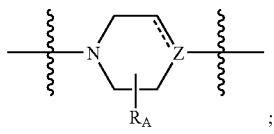

P is CR_P; Q is CR_Q; S is CR_S; T is CR_T; V is CR_V; Y is selected from NR_Y, O, or S; and R_P, R_Q, R_S, R_T, R_V, Z, R₂, R₃, R₄, R_A, R_Y, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

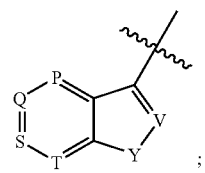
;

D is

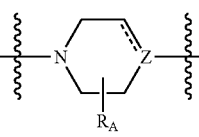
;

B₁ is

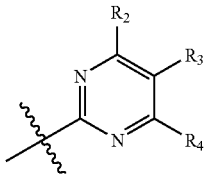

P is CR_P; Q is CR_Q; S is CR_S; T is CR_T; V is CR_V; R_P, R_Q, R_S, R_T, and R_V are independently selected from hydrogen, alkoxy, alkyl, haloalkyl, or halogen; Y is selected from NR_Y, O, or S; R_Y is selected from hydrogen or alkyl; Z is N; --- is absent; R₂, R₃, and R₄ are independently selected from hydrogen, alkyl, or halogen; and R_A is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

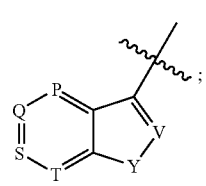
;

D is

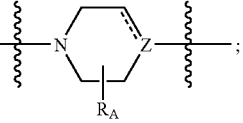
;

$B_1$ is

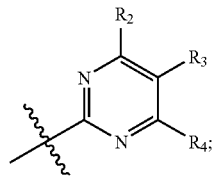

P is $CR_P$; Q is $CR_Q$; S is $CR_S$; T is N; V is $CR_V$; Y is selected from $NR_Y$, O, or S; and $R_P$, $R_Q$, $R_S$, $R_V$, Z, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

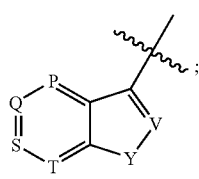

D is

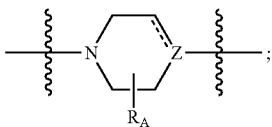

$B_1$ is

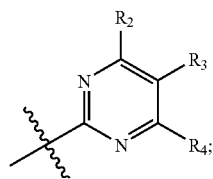

P is $CR_P$; Q is $CR_Q$; S is $CR_S$; T is N; V is $CR_V$; $R_P$, $R_Q$, $R_S$, and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_2$, $R_3$, and $R_4$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

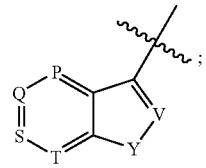

D is

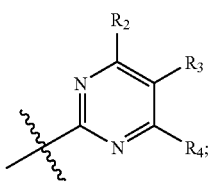

$B_1$ is

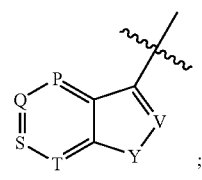

P is N; Q is $CR_Q$; S is $CR_S$; T is $CR_T$; V is $CR_V$; Y is selected from $NR_Y$, O, or S; and $R_Q$, $R_S$, $R_T$, $R_V$, Z, $R_2$, $R_3$, $R_4$, $R_A$, $R_Y$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

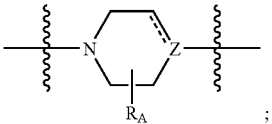

D is $B_1$ is

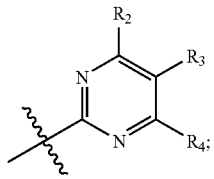

P is N; Q is $CR_Q$; S is $CR_S$; T is $CR_T$; V is $CR_V$; $R_Q$, $R_S$, $R_T$, and $R_V$ are independently selected from hydrogen, alkoxy, alkyl, haloalkyl, or halogen; Y is selected from $NR_Y$, O, or S; $R_Y$ is selected from hydrogen or alkyl; Z is N; --- is absent; $R_2$, $R_3$, and $R_4$ are independently selected from hydrogen, alkyl, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

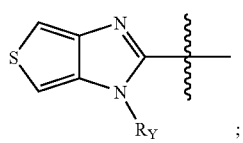

D is

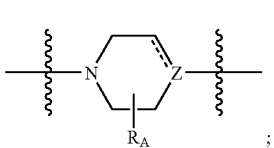

$B_1$ is

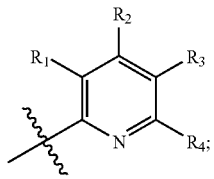

and Z, $R_1$, $R_2$, $R_3$, $R_4$, $R_Y$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

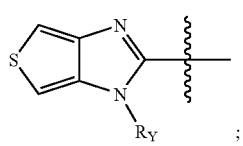

D is

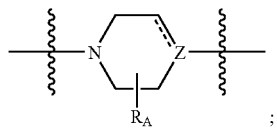

$B_1$ is

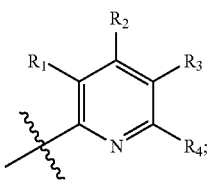

$R_Y$ is selected from hydrogen or alkyl; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

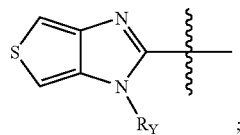

D is

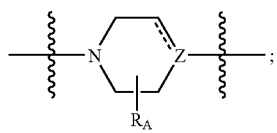

$B_1$ is

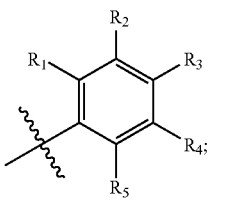

and Z, $R_1$, $R_2$, $R_3$, $R_4$, $R_S$, $R_Y$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

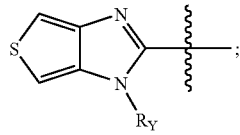

D is

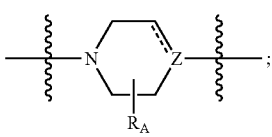

$B_1$ is

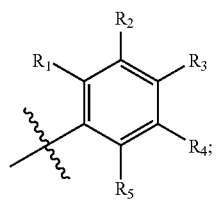

$R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

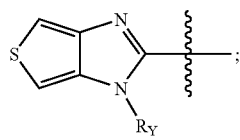

D is

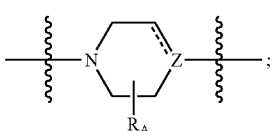

$B_1$ is

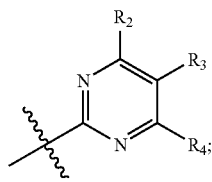

and Z, $R_2$, $R_3$, $R_4$, $R_Y$, $R_A$, and --- are as defined in formula (I).

In another embodiment, the present invention relates to a method of treating sexual dysfunction in a mammal comprising administering to the mammal a therapeutically effective amount of a compound of formula (I) or a pharmaceutically acceptable salt, ester, amide, N-oxide, or prodrug thereof, wherein A is

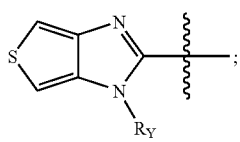

D is

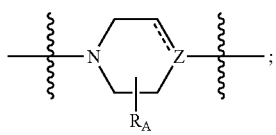

$B_1$ is

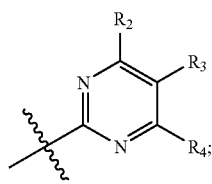

$R_Y$ is selected from hydrogen or alkyl; Z is N; --- is absent; $R_2$, $R_3$, and $R_4$ are independently selected from hydrogen, alkyl, or halogen; and $R_A$ is as defined in formula (I).

In another embodiment, the present invention relates to method of treating sexual dysfunction in a mammal comprising administering to the mammal a therapeutically effective amount of a compound of formula (I) or a pharmaceutically acceptable salt, ester, amide, N-oxide, or prodrug thereof in combination with a pharmaceutically acceptable carrier.

In another embodiment, the present invention relates to method of treating sexual dysfunction in a mammal comprising administering to the mammal a therapeutically effective amount of a compound of formula (I) or a pharmaceutically acceptable salt, ester, amide, N-oxide, or prodrug thereof in combination with a phosphodiesterase 5 inhibitor.

In another embodiment, the present invention relates to method of treating sexual dysfunction in a mammal comprising administering to the mammal a therapeutically effective amount of a compound of formula (I) or a pharmaceutically acceptable salt, ester, amide, N-oxide, or prodrug thereof in combination with an adrenergic receptor antagonist.

In another embodiment, the present invention relates to method of treating sexual dysfunction in a mammal comprising administering to the mammal a therapeutically effective amount of a compound of formula (I) or a pharmaceutically acceptable salt, ester, amide, N-oxide, or prodrug thereof in combination with a dopamine agonist.

In another embodiment, the present invention relates to method of treating male erectile dysfunction in a male human comprising administering to the male human in need of such treatment a therapeutically effective amount of a compound of formula (I) or a pharmaceutically acceptable salt, ester, amide, N-oxide, or prodrug thereof in combination with a pharmaceutically acceptable carrier.

In another embodiment, the present invention relates to method of treating male erectile dysfunction in a mammal comprising administering to the mammal a therapeutically effective amount of a compound of formula (I) or a pharmaceutically acceptable salt, ester, amide, N-oxide, or prodrug thereof in combination with a phosphodiesterase 5 inhibitor.

In another embodiment, the present invention relates to method of treating male erectile dysfunction in a mammal comprising administering to the mammal a therapeutically effective amount of a compound of formula (I) or a pharmaceutically acceptable salt, ester, amide, N-oxide, or prodrug thereof in combination with all adrenergic receptor antagonist.

In another embodiment, the present invention relates to method of treating male erectile dysfunction in a mammal comprising administering to the mammal a therapeutically effective amount of a compound of formula (I) or a pharmaceutically acceptable salt, ester, amide, N-oxide, or prodrug thereof in combination with a dopamine agonist.

In another embodiment, the present invention relates to method of treating female sexual dysfunction in a mammal comprising administering to the mammal in need of such treatment a therapeutically effective amount of a compound of formula (I) or a pharmaceutically acceptable salt, ester, amide, N-oxide, or prodrug thereof in combination with a pharmaceutically acceptable carrier.

In another embodiment, the present invention relates to method of treating female sexual dysfunction in a mammal comprising administering to the mammal a therapeutically effective amount of a compound of formula (I) or a pharmaceutically acceptable salt, ester, amide, N-oxide, or prodrug thereof in combination with a phosphodiesterase 5 inhibitor.

In another embodiment, the present invention relates to method of treating female sexual dysfunction in a mammal comprising administering to the mammal a therapeutically effective amount of a compound of formula (I) or a pharmaceutically acceptable salt, ester, amide, N-oxide, or prodrug thereof in combination with an adrenergic receptor antagonist.

In another embodiment, the present invention relates to method of treating female sexual dysfunction in a mammal comprising administering to the mammal a therapeutically effective amount of a compound of formula (I) or a pharmaceutically acceptable salt, ester, amide, N-oxide, or prodrug thereof in combination with a dopamine agonist.

In another embodiment, the present invention relates to method of treating a disorder selected from cardiovascular disorders, inflamatory disorders, attention deficit hyperactivity disorder, Alzheimer's disease, drug abuse, Parkinson's disease, schizophrenia, anxiety, mood disorders or depression in a mammal comprising administering to the mammal in need of such treatment a therapeutically effective amount of a compound of formula (I) or a pharmaceutically acceptable salt, ester, amide, N-oxide, or prodrug thereof.

In another embodiment of the present invention, compounds of formula (II)

or a pharmaceutically acceptable salt, ester, amide, N-oxide, or prodrug thereof, are disclosed wherein A is selected from the group consisting

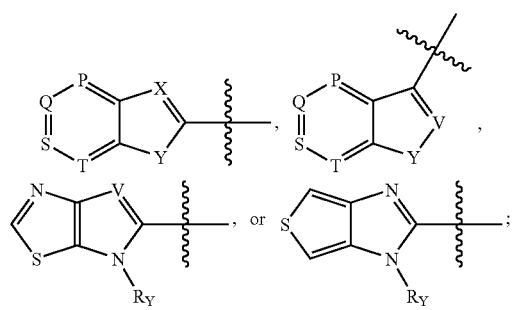

X is selected from $CR_X$ or N;
Y is selected from O, or S;
V is selected from $CR_V$ or N;
P is selected from $CR_P$ or N;
Q is selected from $CR_Q$ or N;
S is selected from $CR_S$ or N;
T is selected from $CR_T$ or N;
provided that 1, or 2 of P, Q, S, and T are N;
$R_P$, $R_Q$, $R_S$, $R_T$, $R_V$, and $R_X$ are independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —$NZ_1Z_2$, $(NZ_3Z_4)$carbonyl, or $(NZ_3Z_4)$sulfonyl;
$Z_1$ and $Z_2$ are each independently selected from hydrogen, alkyl, alkylcarbonyl, alkylsulfonyl, aryl, arylalkyl, arylalkylsulfonyl, arylsulfonyl, or formyl;
$Z_3$ and $Z_4$ are each independently selected from hydrogen, alkyl, aryl, or arylalkyl;
L is alkylene;
D is selected from

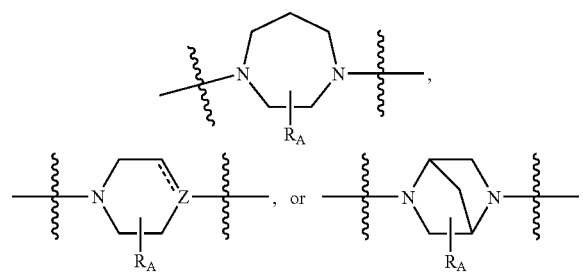

wherein the left end is attached to L and the right end is attached to $B_1$;
$R_A$ is selected from hydrogen or alkyl;
Z is selected from N, C or CH;

--- is a bond when Z is C and --- is absent when Z is N or CH;

B$_1$ is selected from

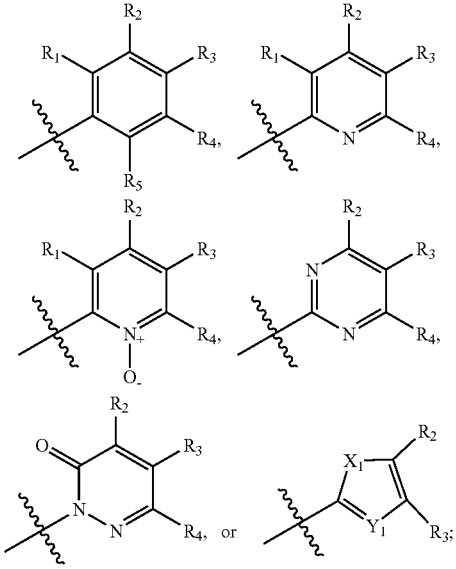

R$_1$, R$_2$, R$_3$, R$_4$ and R$_5$ are each independently selected from hydrogen, alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ$_1$Z$_2$, (NZ$_3$Z$_4$)carbonyl, or (NZ$_3$Z$_4$)sulfonyl;

X$_1$ is selected from N(R$_6$), O or S;

Y$_1$ is selected from C(R$_7$) or N;

R$_6$ is selected from hydrogen or alkyl; and

R$_7$ is selected from hydrogen or alkyl.

In another embodiment of the present invention, compounds of formula (II) or a pharmaceutically acceptable salt, ester, amide, N-oxide, or prodrug thereof, are disclosed wherein A is

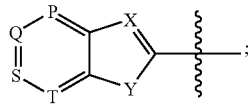

P is N; Q is CR$_Q$; S is CR$_S$; T is CR$_T$; X is CR$_X$; Y is selected from O or S; and R$_Q$, R$_S$, R$_T$, and R$_X$ are as defined in formula (II).

In another embodiment of the present invention, compounds of formula (II) or a pharmaceutically acceptable salt, ester, amide, N-oxide, or prodrug thereof, are disclosed wherein A is

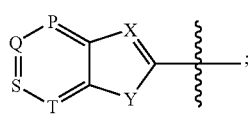

D is

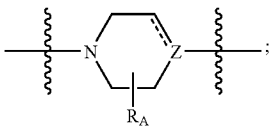

B$_1$ is

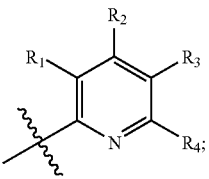

P is N; Q is CR$_Q$; S is CR$_S$; T is CR$_T$; X is CR$_X$; Y is selected from O or S; and Z, R$_Q$, R$_S$, R$_T$, R$_X$, R$_1$, R$_2$, R$_3$, R$_4$, R$_A$ and --- are as defined in formula (II).

In another embodiment of the present invention, compounds of formula (II) or a pharmaceutically acceptable salt, ester, amide, N-oxide, or prodrug thereof, are disclosed wherein A is

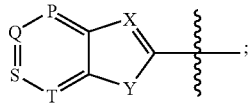

D is

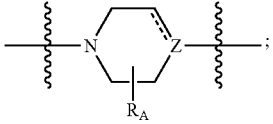

B$_1$ is

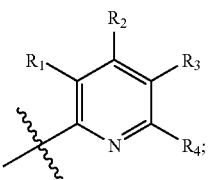

P is N; Q is CR$_Q$; S is CR$_S$; T is CR$_T$; X is CR$_X$; Y is selected from O or S; R$_Q$, R$_S$, R$_T$, and R$_X$ are independently selected from hydrogen, alkoxy, alkyl, haloalkyl, or halogen; Z is N; --- is absent; R$_1$, R$_2$, R$_3$, and R$_4$ are independently selected from hydrogen, alkoxy, alkyl, alkylthio, cyano, or halogen; and R$_A$ is as defined in formula (II).

In another embodiment of the present invention, compounds of formula (II) or a pharmaceutically acceptable salt, ester, amide, N-oxide, or prodrug thereof, are disclosed wherein A is

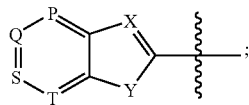

D is

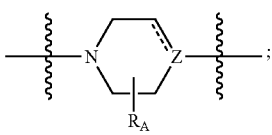

$B_1$ is

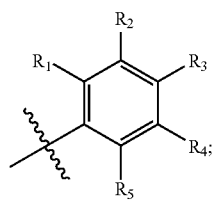

P is N; Q is $CR_Q$; S is $CR_S$; T is $CR_T$; X is $CR_X$; Y is selected from O or S; and $R_Q$, $R_S$, $R_T$, and Z, $R_Q$, $R_S$, $R_T$, $R_X$, $R_1$, $R_2$, $R_3$, $R_4$, $R_5$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

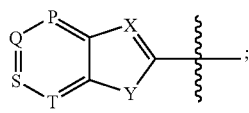

D is

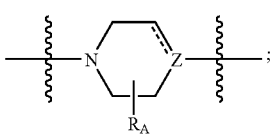

$B_1$ is

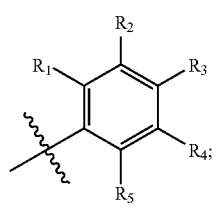

P is N; Q is $CR_Q$; S is $CR_S$; T is $CR_T$; X is $CR_X$; Y is selected from O or S; $R_Q$, $R_S$, $R_T$, and $R_X$ are independently selected from hydrogen, alkoxy, alkyl, haloalkyl, or halogen; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (II).

In another embodiment of the present invention, compounds of formula (II) or a pharmaceutically acceptable salt, ester, amide, N-oxide, or prodrug thereof, are disclosed wherein A is

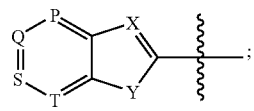

D is

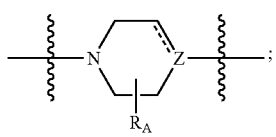

$B_1$ is

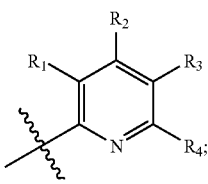

P is N; Q id $CR_Q$; S is $CR_S$; T is $CR_T$; X is N; Y is selected from O or S; and Z, $R_Q$, $R_S$, $R_T$, $R_1$, $R_2$, $R_3$, $R_4$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

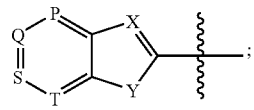

D is

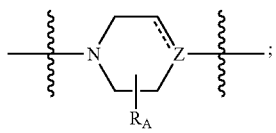

$B_1$ is

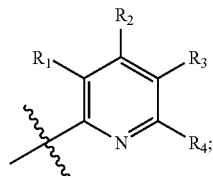

P is N; Q is $CR_Q$; S is $CR_S$; T is $CR_T$; X is N; Y is selected from O or S; $R_Q$, $R_S$, and $R_T$ are independently selected from hydrogen, alkoxy, alkyl, haloalkyl, or halogen; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (II).

In another embodiment of the present invention, compounds of formula (II) or a pharmaceutically acceptable salt, ester, amide, N-oxide, or prodrug thereof, are disclosed wherein A is

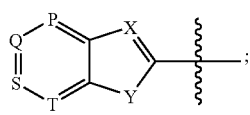

D is

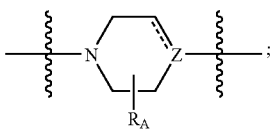

$B_1$ is

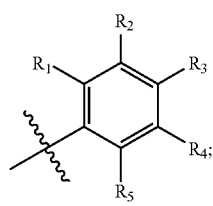

P is N; Q is $CR_Q$; S is $CR_S$; T is $CR_T$;
X is N; Y is selected from O or S; and Z, $R_Q$, $R_S$, $R_T$, $R_1$, $R_2$, $R_3$, $R_4$, $R_5$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

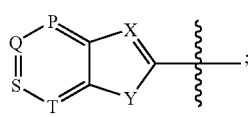

D is

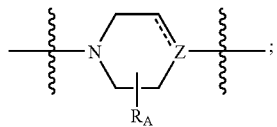

$B_1$ is

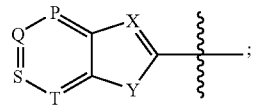

P is N; Q is $CR_Q$; S is $CR_S$; T is $CR_T$; X is N; Y is selected from O or S; $R_Q$, $R_S$, and $R_T$ are independently selected from hydrogen, alkoxy, alkyl, haloalkyl, or halogen; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (II).

In another embodiment of the present invention, compounds of formula (II) or a pharmaceutically acceptable salt, ester, amide, N-oxide, or prodrug thereof, are disclosed wherein

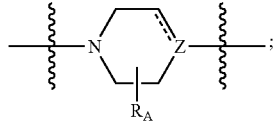

D is

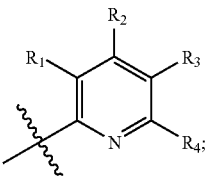

$B_1$ is

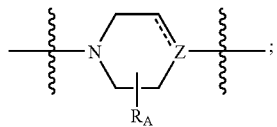

P is $CR_P$; Q is $CR_Q$; S is $CR_S$; T is N; X is N; Y is selected from O or S; and Z, $R_P$, $R_Q$, $R_S$, $R_1$, $R_2$, $R_3$, $R_4$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

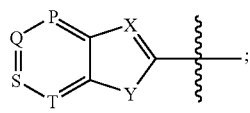

D is

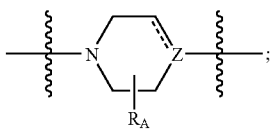

$B_1$ is

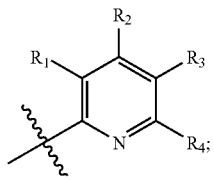

P is $CR_P$; Q is $CR_Q$; S is $CR_S$; T is N; X is N; Y is selected from O or S; $R_P$, $R_Q$, and $R_S$ are independently selected from hydrogen, alkoxy, alkyl, haloalkyl, or halogen; Z is N; --- is absent; $R_1$, $R_2$, $R_3$, and $R_4$ are independently selected from hydrogen, alkoxy, alkyl, alkylthio, cyano, or halogen; and $R_A$ is as defined in formula (II).

In another embodiment of the present invention, compounds of formula (II) or a pharmaceutically acceptable salt, ester, amide, N-oxide, or prodrug thereof, are disclosed wherein A is

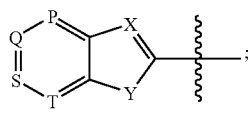

D is

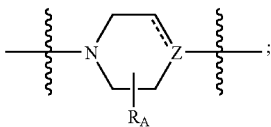

$B_1$ is

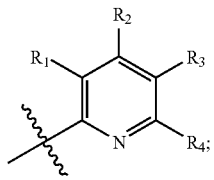

P is $CR_P$; Q is $CR_Q$; S is $CR_S$; T is N; X is N; Y is selected from O or S; $R_P$, $R_Q$, and $R_S$ are independently selected from the group consisting of hydrogen, alkoxy, alkyl, haloalkyl, or halogen; Z is CH; --- is absent; $R_1$, $R_2$, $R_3$, and $R_4$ are independently selected from the group consisting of hydrogen, alkoxy, alkyl, alkylthio, cyano, or halogen; and $R_A$ is as defined in formula (II).

In another embodiment of the present invention, compounds of formula (II) or a pharmaceutically acceptable salt, ester, amide, N-oxide, or prodrug thereof, are disclosed wherein A is

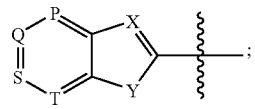

D is

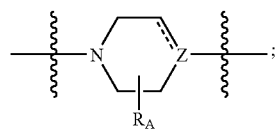

$B_1$ is

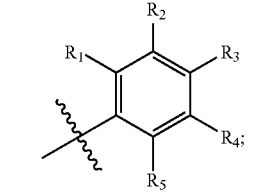

P is $CR_P$; Q is $CR_Q$; S is $CR_S$; T is N; X is N; Y is selected from O or S; and Z, $R_P$, $R_Q$, $R_S$, $R_1$, $R_2$, $R_3$, $R_4$, $R_5$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

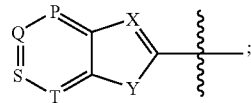

D is

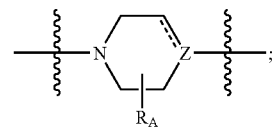

$B_1$ is

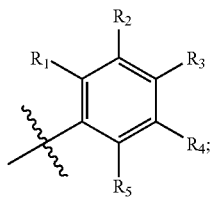

P is $CR_P$; Q is $CR_Q$; S is $CR_S$; T is N; X is N; Y is selected from O or S; $R_P$, $R_Q$, and $R_S$ are independently selected from hydrogen, alkoxy, alkyl, haloalkyl, or halogen; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (II).

In another embodiment of the present invention, compounds of formula (II) or a pharmaceutically acceptable salt, ester, amide, N-oxide, or prodrug thereof, are disclosed wherein A is

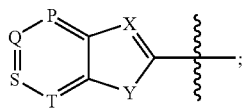

D is

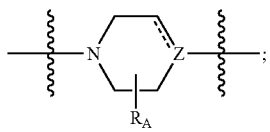

$B_1$ is

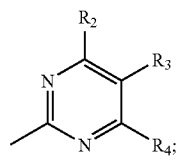

P is $CR_P$; Q is $CR_Q$; S is $CR_S$; T is N; X is N; Y is selected from O or S; and Z, $R_P$, $R_Q$, $R_S$, $R_2$, $R_3$, $R_4$, $R_A$ and --- are as defined in formula (II).

In another embodiment of the present invention, compounds of formula (II) or a pharmaceutically acceptable salt, ester, amide, N-oxide, or prodrug thereof, are disclosed wherein A is

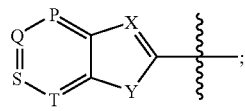

D is

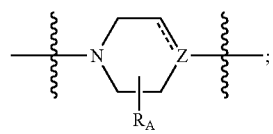

$B_1$ is

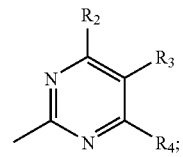

P is $CR_P$; Q is $CR_Q$; S is $CR_S$; T is N; X is N; Y is selected from O or S; $R_P$, $R_Q$, and $R_S$ are independently selected from hydrogen, alkoxy, alkyl, haloalkyl, or halogen; Z is N; --- is absent; $R_2$, $R_3$, and $R_4$ are independently selected from hydrogen, alkyl, or halogen; and $R_A$ is as defined in formula (II).

In another embodiment of the present invention, compounds of formula (II) or a pharmaceutically acceptable salt, ester, amide, N-oxide, or prodrug thereof, are disclosed wherein A is

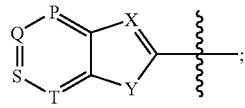

D is

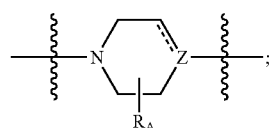

$B_1$ is

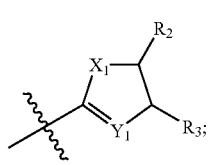

P is CR$_P$; Q is CR$_Q$; S is CR$_S$; T is N; X is N; Y is selected from O or S; and X$_1$, Y$_1$, Z, R$_P$, R$_Q$, R$_S$, R$_2$, R$_3$, R$_4$ and --- are as defined in formula (II).

In another embodiment of the present invention, compounds of formula (II) or a pharmaceutically acceptable salt, ester, amide, N-oxide, or prodrug thereof, are disclosed wherein A is

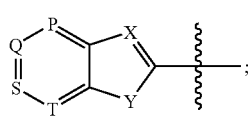

D is

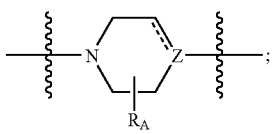

B$_1$ is

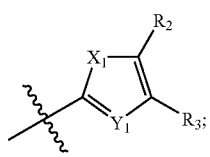

P is CR$_P$; Q is CR$_Q$; S is CR$_S$; T is N; X is N; Y is selected from O or S; R$_P$, R$_Q$, and R$_S$ are independently selected from hydrogen, alkoxy, alkyl, haloalkyl, or halogen; X$_1$ is S; Y$_1$ is N; Z is N; --- is absent; R$_2$, and R$_3$ are independently selected from hydrogen, alkyl, or halogen; and R$_4$ is as defined in formula (II).

In another embodiment of the present invention, compounds of formula (II) or a pharmaceutically acceptable salt, ester, amide, N-oxide, or prodrug thereof, are disclosed wherein A is

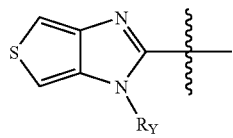

and R$_Y$ is as defined in formula (II).

In another embodiment of the present invention, compounds of formula (II) or a pharmaceutically acceptable salt, ester, amide, N-oxide, or prodrug thereof, are disclosed wherein A is

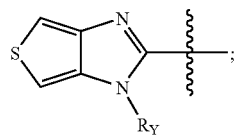

D is

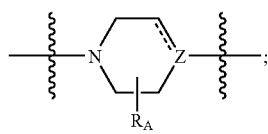

B$_1$ is

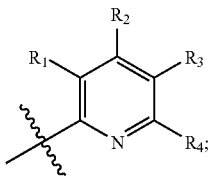

R$_Y$ is selected from hydrogen or alkyl; Z is N; --- is absent; R$_1$, R$_2$, R$_3$, and R$_4$ are independently selected from hydrogen, alkoxy, alkyl, alkylthio, cyano, or halogen; and R$_A$ is as defined in formula (II).

In another embodiment of the present invention, compounds of formula (II) or a pharmaceutically acceptable salt, ester, amide, N-oxide, or prodrug thereof, are disclosed wherein A is

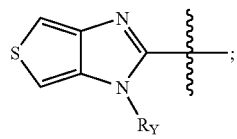

D is

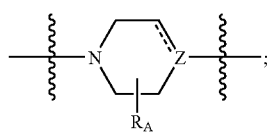

B$_1$ is

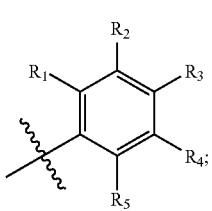

and $R_Y$, $R_A$, Z, $R_1$, $R_2$, $R_3$, $R_4$, $R_5$, and --- are as defined in formula (II).

In another embodiment of the present invention, compounds of formula (II) or a pharmaceutically acceptable salt, ester, amide, N-oxide, or prodrug thereof, are disclosed wherein A is

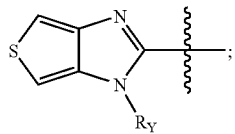

D is

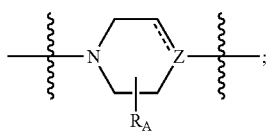

$B_1$ is

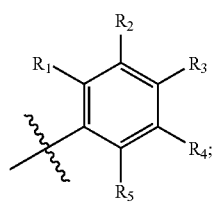

$R_Y$ is selected from hydrogen or alkyl; Z is N; --- is absent; $R_1$, $R_2$, $R_3$, $R_4$, and $R_5$ are independently selected from hydrogen, alkoxy, alkyl, alkylthio, cyano, halogen, or hydroxy; and $R_A$ is as defined in formula (II).

In another embodiment of the present invention, compounds of formula (II) or a pharmaceutically acceptable salt, ester, amide, N-oxide, or prodrug thereof, are disclosed wherein A is

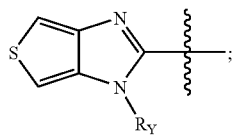

D is

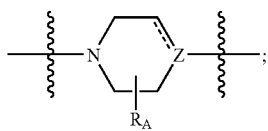

$B_1$ is

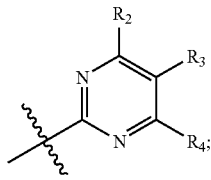

and $R_Y$, $R_A$, Z, $R_2$, $R_3$, $R_4$, and --- are as defined in formula (II).

In another embodiment of the present invention, compounds of formula (II) or a pharmaceutically acceptable salt, ester, amide, N-oxide, or prodrug thereof, are disclosed wherein A is

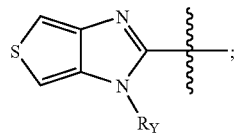

D is

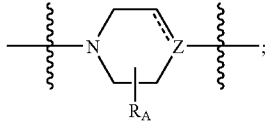

$B_1$ is

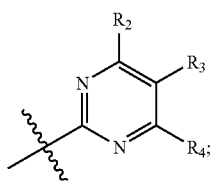

$R_Y$ is selected from hydrogen or alkyl; Z is N; --- is absent; $R_2$, $R_3$, and $R_4$ are independently selected from hydrogen, alkyl, or halogen; and $R_A$ is as defined in formula (II).

DEFINITIONS OF THE PRESENT INVENTION

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a monocyclic-ring system, or a bicyclic- or a tricyclic-fused ring system wherein one or more of the fused rings are aromatic. Representative examples of aryl include, but are not limited to, anthracenyl, azulenyl, fluorenyl, 2,3-dihydroindenyl, indenyl, naphthyl, phenyl, and tetrahydronaphthyl.

The aryl groups of this invention are substituted with 0, 1, 2, 3, 4, or 5 substituents independently selected from alkoxy, alkenyl, alkyl, alkylsulfinyl, alkylsulfonyl, alkylthio, alkynyl, alkoxycarbonyl, alkylcarbonyl, alkylcarbonyloxy, carboxy, cyano, formyl, halogen, haloalkoxy, haloalkyl, hydroxy, hydroxyalkyl, mercapto, nitro, —NZ$_1$Z$_2$, (NZ$_3$Z$_4$)carbonyl, and (NZ$_3$Z$_4$)sulfonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "arylalkylsulfonyl" as used herein, means an arylalkyl group, as defined herein, appended to the parent molecular moiety through a sulfonyl group.

The term "arylsulfonyl" as used herein, means an aryl group, as defined herein, appended to the parent molecular moiety through a sulfonyl group.

The term "carbonyl" as used herein, means a —C(O)— group.

The term "carboxy" as used herein, means a —CO$_2$H group.

The term "cyano" as used herein, means a —CN group.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitrogen protecting group" as used herein, means those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), tert-butylacetyl, trifluoroacetyl, and triphenylmethyl (trityl).

The term "nitro" as used herein, means a —NO$_2$ group.

The term "(NZ$_3$Z$_4$)carbonyl" as used herein, means a —NZ$_3$Z$_4$ group, as defined herein, appended to the parent molecular moiety through a carbonyl group, as defined herein. Representative examples of (NZ$_3$Z$_4$)carbonyl include, but are not limited to, aminocarbonyl, (methylamino)carbonyl, (dimethylamino)carbonyl, benzylamino, phenylamino, and (ethylmethylamino)carbonyl.

The term "(NZ$_3$Z$_4$)sulfonyl" as used herein, means a —NZ$_3$Z$_4$ group, as defined herein, appended to the parent molecular moiety through a sulfonyl group, as defined herein.

The term "oxo" as used herein, means a =O moiety.

The term "sulfinyl" as used herein, means a —S(O)— group.

The term "sulfonyl" as used herein, means a —SO$_2$— group.

The term "sexual dysfunction" as used herein, means sexual dysfunction in mammals including human male and human female sexual dysfunction.

The term "male sexual dysfunction" as used herein includes, but is not limited to, male erectile dysfunction or premature ejaculation.

The term "female sexual dysfunction" as used herein includes, but is not limited to, female anorgasmia, clitoral erectile insufficiency, vaginal engorgement, dyspareunia, or vaginismus.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The present invention contemplates various stereoisomers and mixtures thereof and are specifically included within the scope of this invention. Stereoisomers include enanitiomers and diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.0 (developed by Advanced Chemistry Development, Inc., Toronto, ON, Canada) or were given names which appeared to be consistent with ACD nomenclature.

Preferred compounds of the present invention include:
2-{1-[(5-chloro-1-benzothien-3-yl)methyl]-4-piperidinyl}pyridine;
1-[(5-chloro-1-benzothien-3-yl)methyl]-4-(6-methyl-2-pyridinyl)piperazine;
2-{4-[(5-chloro-1-benzothien-3-yl)methyl]-1-piperazinyl}benzonitrile;
1-[(5-chloro-1-benzothien-3-yl)methyl]-4-(2-pyridinyl)piperazine;
1-[(5-chloro-1-benzothien-3-yl)methyl]-4-(2-fluorophenyl)piperazine;
2-{4-[(5-chloro-1-benzothien-3-yl)methyl]-1-piperazinyl}pyrimidine;
1-(1-benzothien-3-ylmethyl)-4-(2-pyridinyl)piperazine;
2-[4-(1-benzothien-2-ylmethyl)-1-piperazinyl]benzonitrile;
1-(1-benzothien-2-ylmethyl)-4-(2-fluorophenyl)piperazine;
1-(1-benzothien-2-ylmethyl)-4-(2-pyridinyl)piperazine;
2-{4-[(5-fluoro-1H-indol-2-yl)methyl]-1,4-diazepan-1-yl}benzonitrile;
2-{1-[4-(2-methoxyphenyl)-1-piperazinyl]ethyl}-1H-indole;
2-{[4-(2-methoxyphenyl)-1-piperazinyl]methyl}-1-methyl-1H-indole;
2-{1-[4-(2-pyridinyl)-1-piperazinyl]ethyl}-1H-indole;
5-fluoro-2-{[(1S,4S)-5-(2-pyridinyl)-2,5-diazabicyclo[2.2.1]hept-2-yl]methyl}-1H-indole;
5-fluoro-2-{[4-(2-pyridinyl)-1,4-diazepan-1-yl]methyl}-1H-indole;
2-[4-(1H-pyrrolo[2,3-b]pyridin-2-ylmethyl)-1-piperazinyl]benzonitrile;
2-{[4-(2-pyrimidinyl)-1-piperazinyl]methyl}-1H-pyrrolo[2,3-b]pyridine;
2-{[4-(2-methoxyphenyl)-1-piperazinyl]methyl}-1H-pyrrolo[2,3-b]pyridine;
2-{[4-(2-pyridinyl)-1-piperazinyl]methyl}-1H-pyrrolo[2,3-b]pyridine;
2-[(4-phenyl-1-piperazinyl)methyl]-1H-pyrrolo[2,3-b]pyridine;
2-{[4-(2-fluorophenyl)-1-piperazinyl]methyl}-1H-pyrrolo[2,3-b]pyridine;
2-[4-(1H-pyrrolo[2,3-b]pyridin-2-ylmethyl)-1-piperazinyl]nicotinonitrile;
4-(4-{[6-(trifluoromethyl)thieno[3,2-b]pyridin-2-yl]methyl}-1-piperazinyl)phenol;
2-{[4-(2-methoxyphenyl)-1-piperazinyl]methyl}-6-(trifluoromethyl)thieno[3,2-b]pyridine;
2-(4-{[6-(trifluoromethyl)thieno[3,2-b]pyridin-2-yl]methyl}-1-piperazinyl)benzonitrile;
4-[4-(furo[3,2-b]pyridin-2-ylmethyl)-1-piperazinyl]phenol;
2-[(4-phenyl-1-piperazinyl)methyl]furo[3,2-b]pyridine;
2-{[4-(2-methoxyphenyl)-1-piperazinyl]methyl}furo[3,2-b]pyridine;
2-[4-(furo[3,2-b]pyridin-2-ylmethyl)-1-piperazinyl]benzonitrile;
2-{[4-(3-methyl-2-pyridinyl)-1-piperazinyl]methyl}furo[3,2-b]pyridine;
2-[4-(furo[3,2-b]pyridin-2-ylmethyl)-1-piperazinyl]nicotinonitrile;
2-{[4-(2-pyridinyl)-1-piperazinyl]methyl}furo[3,2-b]pyridine;
2-{[4-(2-fluorophenyl)-1-piperazinyl]methyl}furo[3,2-b]pyridine;
2-{[4-(2-methoxyphenyl)-1-piperazinyl]methyl}[1,3]oxazolo[4,5-b]pyridine;
2-[4-([1,3]oxazolo[4,5-b]pyridin-2-ylmethyl)-1-piperazinyl]benzonitrile;
2-{[4-(2-pyridinyl)-1-piperidinyl]methyl}[1,3]thiazolo[5,4-b]pyridine;
2-{[4-(1,3-thiazol-2-yl)-1-piperazinyl]methyl}[1,3]thiazolo[5,4-b]pyridine;
4-{4-[(5-methoxy[1,3]thiazolo[5,4-b]pyridin-2-yl)methyl]-1-piperazinyl}phenol;
2-{[4-(2-fluorophenyl)-1-piperazinyl]methyl}-5-methoxy[1,3]thiazolo[5,4-b]pyridine;
5-methoxy-2-({4-[2-(methylthio)phenyl]-1-piperazinyl}methyl)[1,3]thiazolo[5,4-b]pyridine;
5-methoxy-2-{[4-(6-methyl-2-pyridinyl)-1-piperazinyl]methyl}[1,3]thiazolo[5,4-b]pyridine;
5-methoxy-2-{[4-(2-pyridinyl)-1-piperazinyl]methyl}[1,3]thiazolo[5,4-b]pyridine;
5-methoxy-2-{[4-(2-pyrimidinyl)-1-piperazinyl]methyl}[1,3]thiazolo[5,4-b]pyridine;
5-methoxy-2-{[4-(2-methoxyphenyl)-1-piperazinyl]methyl}[1,3]thiazolo[5,4-b]pyridine;
2-{[4-(2-chlorophenyl)-1-piperazinyl]methyl}-5-methoxy[1,3]thiazolo[5,4-b]pyridine;
2-{4-[(5-methoxy[1,3]thiazolo[5,4-b]pyridin-2-yl)methyl]-1-piperazinyl}benzonitrile;
2-{[4-(2-chlorophenyl)-1-piperazinyl]methyl}[1,3]thiazolo[5,4-b]pyridine;
2-{[4-(6-methyl-2-pyridinyl)-1-piperazinyl]methyl}[1,3]thiazolo[5,4-b]pyridine;

2-{[4-(5-chloro-2-methoxyphenyl)-1-piperazinyl]methyl}[1,3]thiazolo[5,4-b]pyridine;

4-[4-([1,3]thiazolo[5,4-b]pyridin-2-ylmethyl)-1-piperazinyl]phenol;

2-[4-([1,3]thiazolo[5,4-b]pyridin-2-ylmethyl)-1-piperazinyl]nicotinonitrile;

2-({4-[2-(methylthio)phenyl]-1-piperazinyl}methyl)[1,3]thiazolo[5,4-b]pyridine;

2-{[4-(2-pyrimidinyl)-1-piperazinyl]methyl}[1,3]thiazolo[5,4-b]pyridine;

2-{[4-(2-pyridinyl)-1-piperazinyl]methyl}[1,3]thiazolo[5,4-b]pyridine;

2-{[4-(2-fluorophenyl)-1-piperazinyl]methyl}[1,3]thiazolo[5,4-b]pyridine;

2-[4-([1,3]thiazolo[5,4-b]pyridin-2-ylmethyl)-1-piperazinyl]benzonitrile;

2-{[4-(2-methoxyphenyl)-1-piperazinyl]methyl}[1,3]thiazolo[5,4-b]pyridine;

2-[(4-phenyl-1-piperazinyl)methyl][1,3]thiazolo[5,4-b]pyridine;

2-{[4-(2-fluorophenyl)-1-piperazinyl]methyl}-1H-thieno[3,4-d]imidazole;

2-{[4-(2-methoxyphenyl)-1-piperazinyl]methyl}-1H-thieno[3,4-d]imidazole;

2-{[4-(2-pyrimidinyl)-1-piperazinyl]methyl}-1H-thieno[3,4-d]imidazole;

2-{[4-(2-pyridinyl)-1-piperazinyl]methyl}-1H-thieno[3,4-d]imidazole;

2-[4-(1H-thieno[3,4-d]imidazol-2-ylmethyl)-1-piperazinyl]nicotinonitrile;

4-[4-(1H-thieno[3,4-d]imidazol-2-ylmethyl)-1-piperazinyl]phenol; and 2  2-({4-[2-(methylthio)phenyl]-1-piperazinyl}methyl)-1H-thieno[3,4-d]imidazole or a pharmaceutically acceptable salt, ester, amide, N-oxide, or prodrug thereof.

Abbreviations

Abbreviations which have been used in the descriptions of the Schemes and the Examples that follow are: Ac for acetyl; BINAP for 2,2'-bis(diphenylphosphino)-1,1'-binaphthyl; Boc for tert-butoxycarbonyl; nBuLi for n-butyllithium; dba for dibeizylideneacetone; DCC for 1,3-dicyclohexylcarbodiimide; DCM for dichloromethane; $D_1$ EA for diisopropylethylamine; DME for 1,2-dimethoxyethane; DMF for N,N-dimethylformamide; DMSO for dimethylsulfoxide; EtOH for ethanol; HPLC for high pressure liquid chromatography; LAH for lithium aluminum hydride; MeOH for methanol; TEA for triethylamine; Tf for $CF_3S(O)_2$—; TFA for trifluoroacetic acid; THF for tetrahydrofuran; TLC for thin layer chromatography.

PREPARATION OF COMPOUNDS OF THE PRESENT INVENTION

The compounds and processes of the present invention will be better understood in connection with the following synthetic Schemes and Examples which illustrate a means by which the compounds of the present invention can be prepared.

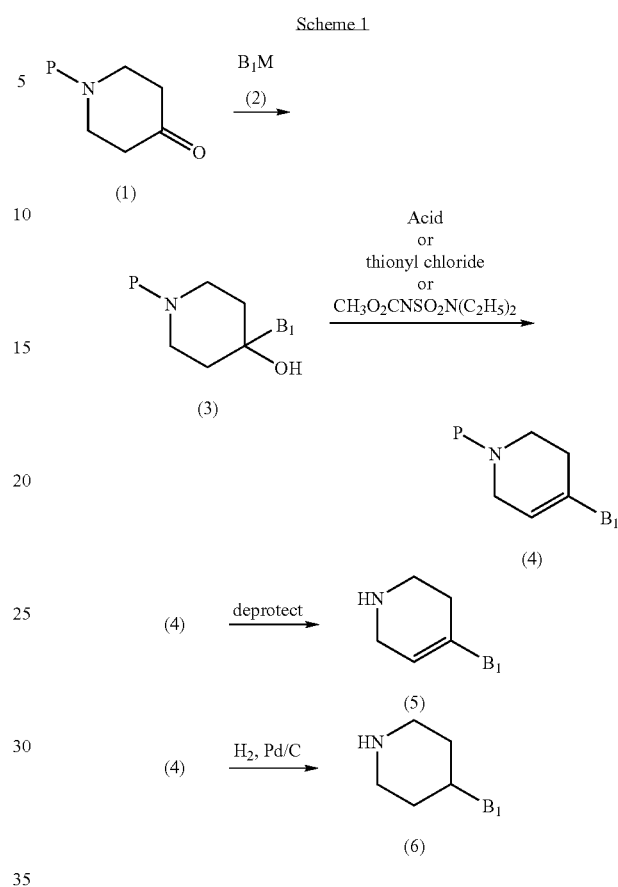

Compounds of general formula (5) and (6), wherein $B_1$ is as defined in formula (I) can be prepared as described in Scheme 1. Piperidinones of general formula (I), purchased commercially or prepared using standard methods know to those of skill in the art wherein P is a nitrogen protecting group such as, but not limited to, $(CH_3)_3CO_2C$— or $C_6H_5CH_2O_2C$—, can be treated with compounds of general formula (2), wherein M is Li, MgBr, MgCl, Cu, or Zn to provide compounds of general formula (3). Compounds of general formula (3) can be treated with Burgess Reagent, thionyl chloride or an acid such as, but not limited to, sulfuric acid or trifluoracetic acid to provide dihyropyridines of general formula (4). Dihyropyridines of general formula (4) can be deprotected using standard methods known to those of ordinary skill in the art to provide compounds of general formula (5). Compounds of general formula (4) can also be treated with a metal catalyst such as palladium on carbon under a hydrogen atmosphere in a solvent such as ethyl acetate, ethanol, or methanol to provide compounds of general formula (6).

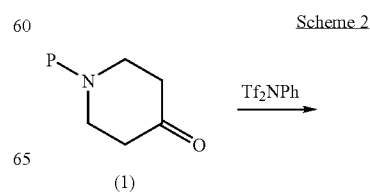

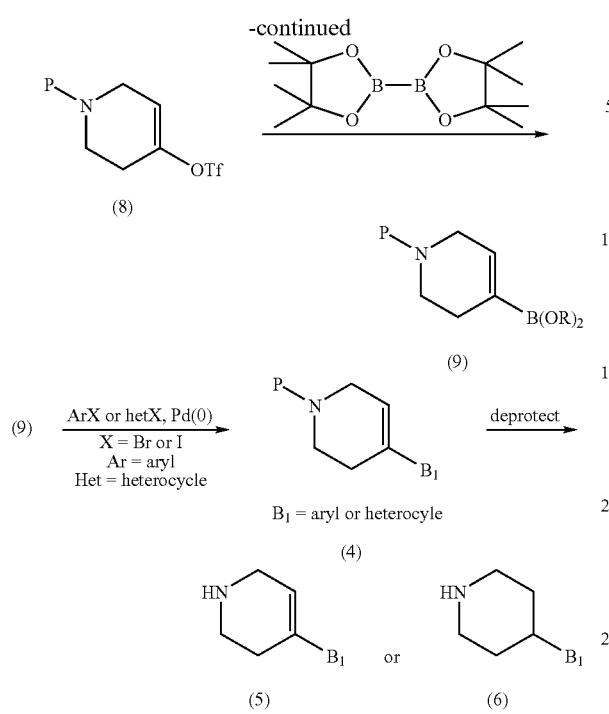

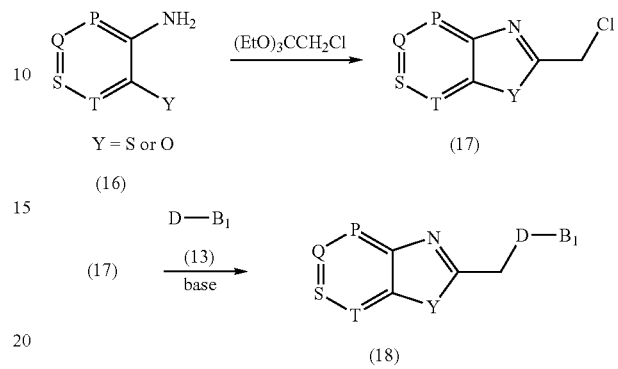

Compounds of general formula (18), wherein P, Q, S, T, D, and $B_1$ are as defined in formula (I), can be prepared as described in Scheme 4. Anilines of general formula (16), purchased or prepared using standard chemistry known to the art, can be treated with 2-chloro-1,1,1-triethoxyethane to provide chloromethyl compounds of general formula (17). Chloromethyl compounds of general formula (17) can be treated with compounds of general formula (13) and a base such as, but not limited to, TEA or $D_1$ EA to provide compounds of general formula (18).

Compounds of general formula (5) and (6), wherein $B_1$ is as defined in formula (I), can be prepared as described in Scheme 2. Piperidinones of general formula (I), purchased commercially or prepared using standard methods know to those of skill in the art wherein P is a nitrogen protecting group such as, but not limited to, $(CH_3)_3CO_2C$— or $C_6H_5CH_2O_2C$—, can be treated with $Tf_2NPh$ to provide triflates of general formula (8). Triflates of general formula (8) can be treated with diborane pinacol ester to provide boranes of general formula (9). Boranes of general formula (9) can be treated with ArX or HetX in the presence of a Pd(0) catalyst to provide compounds of general formula (4). Compounds of general formula (4) can be processed as described in Scheme 1 to provide compounds of general formula (5) and (6).

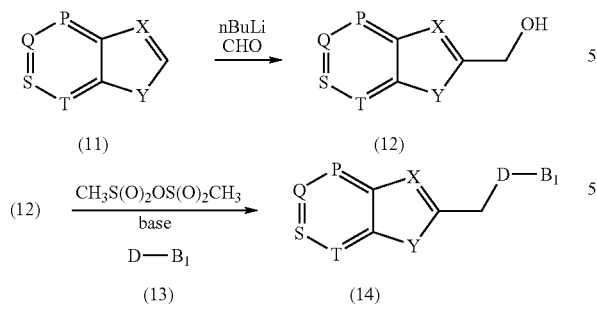

Compounds of general formula (14), wherein P, Q, S, T, X, Y, D, and $B_1$ are as defined in formula (I), can be prepared as described in Scheme 3. Fused heterocycles of general formula (11) can be treated with n-butyllithium and paraformaldehyde to provide alcohols of general formula (12). Alcohols of general formula (12) can be treated with methane sulfonic anhydride, a base such as, but not limited to, TEA or $D_1$ EA, and a compound of formula (13) to provide compounds of formula (14).

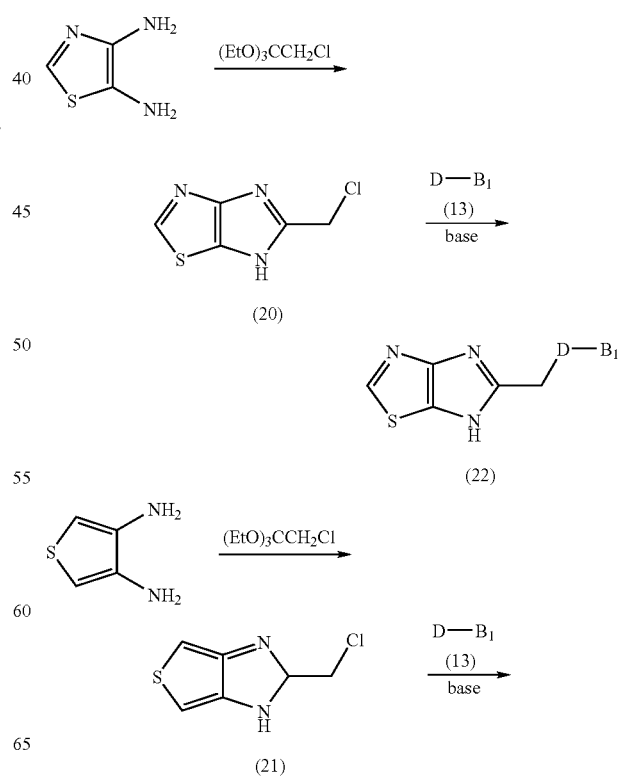

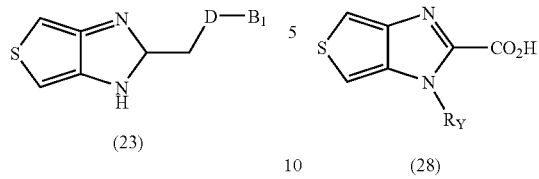

(23)

Compounds of general formula (22) and (23), wherein D and $B_1$ are as defined in formula (I), can be prepared as described in Scheme 5. 3,4-Thiophenediamine or 1,3-thiazole-4,5-diamine can be treated with 2-chloro-1,1,1-triethoxyethane to provide chloromethyl compounds of general formula (20) and (21). Chloromethyl compounds of general formula (20) and (21) can be treated with compounds of general formula (13) and a base such as, but not limited to, TEA or $D_1$EA to provide compounds of general formula (22) and (23).

Scheme 6

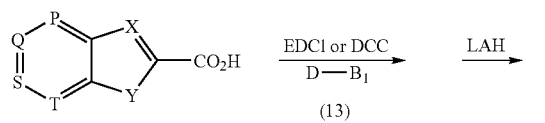

(25)

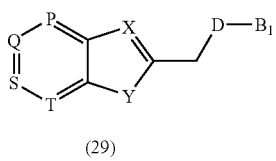

(29)

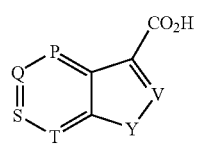

(26)

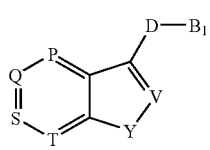

(30)

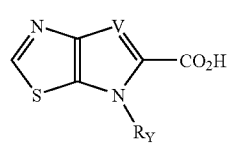

(27)

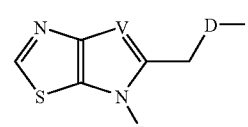

(31)

(28)

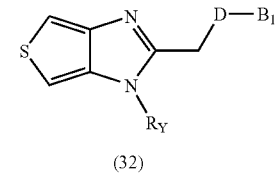

(32)

Compounds of general formula (29), (30), (31), and (32), wherein $R_Y$ is as defined in formula (I), can be prepared as described in Scheme 6. Acids of general formula (25), (26), (27), and (28), purchased or prepared using standard methods known to those in the art, can be treated with compounds of general formula (13) and a coupling reagent such as, but not limited to, EDCI or DCC to provide the corresponding amides. The amides can be treated with LAH or $BH_3$ to provide compounds of general formula (29), (30), (31), and (32).

Scheme 7

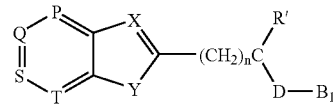

(34)

R' = H or alkyl
n = 0-6

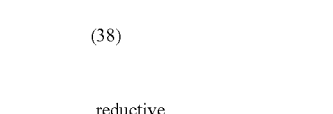

(38)

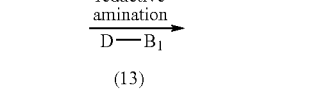

(35)

R' = H or alkyl
n = 0-6

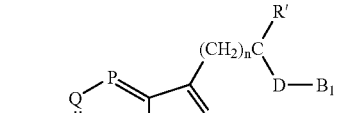

(39)

-continued

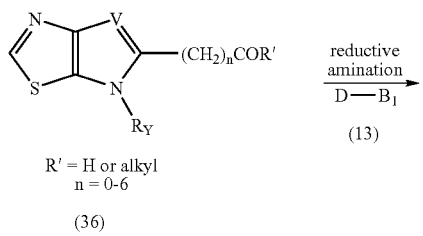

R' = H or alkyl
n = 0-6
(36)

(40)

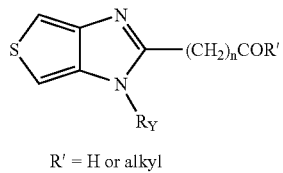

R' = H or alkyl
n = 0-6
(37)

(41)

Compounds of general formula (38), (39), (40), and (41), wherein $R_Y$, D, and $B_1$ are as defined in formula (I), can be prepared as described in Scheme 7. Ketones or aldehydes of general formula (34), (35), (36), or (37), purchased or prepared using standard methods known to those in the art, can be treated with compounds of general formula (13) under standard reductive amination conditions known to those in the art such as, but not limited to, sodium cyanoborohydride or sodium triacetoxyborohydride under acidic conditions in a solvent such as but not limited to, THF, ethanol, or methanol, to provide compounds of general formula (38), (39), (40), and (41).

The following Examples are intended as an illustration of and not a limitation upon the scope of the invention as defined in the appended claims.

EXAMPLE 1

2-{1-[(5-chloro-1-benzothien-3-yl)methyl]-4-piperidinyl}pyridine 3-(Bromomethyl)-5-chloro-1-benzothiophene (150 mg 0.9 mmol) and 4-(2-pyridyl)piperidine (181 mg, 1.0 mmol) were processed as described in Example 2 to provide the title compound. $^1$H NMR (300 MHz, $d_6$-DMSO) δ 2.73 (t, J=1.86 Hz, 4H)) 3.18 (m, 4H) 3.55 (s, 1H) 4.63 (s, 2H) 7.29 (m, 2H) 7.50 (dd, J=8.31, 1.86 Hz, 1H) 7.78 (m, 1H) 8.15 (m, 2H) 8.32 (m, 1H) 8.53 (s, 1H); (ESI) m/z 343 (M+H)$^+$.

EXAMPLE 2

1-[(5-chloro-1-benzothien-3-yl)methyl]-4-(6-methyl-2-pyridinyl)piperazine 3-(Bromomethyl)-5-chloro-1-benzothiophene (1 mmol, maybridge chemical) and 1-(6-methyl-2-pyridinyl)piperazine (1 mmol) were combined in 2 mL of acetonitrile and 1 mL of dimethylformamide and stirred at 25° C. for 5 minutes. The mixture was heated briefly to dissolve any solids and allowed to cool to 25° C. The mixture was monitored by thin layer chromatography until disappearance of starting residue. The mixture was poured into dichloromethane and washed with dilute aqueous ammonium hydroxide. The organic phase was dried over sodium sulfate, filtered, and the filtrate concentrated. The residue was purified by flash chromatography with dichloromethane/methanol/saturated aqueous ammonia to provide the title compound. $^1$H NMR ($d_6$-DMSO, 300 MHz) δ 2.29 (s, 3H), 3.31 (m, 6H), 3.45 (m, 2H), 3.74 (s, 2H), 6.48 (d, 1H, J=7.5 Hz), 6.57 (d, 1H, J=7.8 Hz), 7.38-7.42 (m, 2H), 7.71 (s, 1H), 8.02 (d, 1H, J=7.8 Hz), 8.06 (d, 1H, J=1.5 Hz); MS (DCI/NH$_3$) m/z 358.1 (M+H)$^+$.

EXAMPLE 3

2-{4-[(5-chloro-1-benzothien-3-yl)methyl]-1-piperazinyl}benzonitrile 3-(Bromomethyl)-5-chloro-1-benzothiophene and 2-(1-piperazinyl)benzonitrile were processed as described in Example 2 to provide the title compound. $^1$H NMR ($d_6$-DMSO, 300 MHz) δ 3.2-3.65 (m, 10H), 7.21 (m, 1H), 7.28 (d, 1H, J=7.8 Hz), 7.51 (dd, 1H, J=7.8, 1.5 Hz), 7.66 (m, 1H), 7.79 (dd, 1H, J=7.5, 1.5 Hz), 8.14 (d, 1H, J=7.8 Hz), 8.25 (s, 1H), 8.40 (s, 1H). MS (DCI/NH$_3$) m/z 368.1 (M+H)$^+$.

EXAMPLE 4

1-[(5-chloro-1-benzothien-3-yl)methyl]-4-(2-pyridinyl)piperazine 3-(Bromomethyl)-5-chloro-1-benzothiophene and 1-(2-pyridinyl)piperazine were processed as described in Example 2 to provide the title compound. $^1$H NMR ($d_6$-DMSO, 300 MHz) δ 3.15 (m, 2H), 3.49 (m, 6H), 3.75 (s, 2H), 6.61 (dd, 1H, J=7.5, 4.5 Hz), 6.80 (d, 1H, J=8.7 Hz), 7.40 (dd, 1H, J=8.7, 1.5), 7.52 (m, 1H), 7.70 (s, 1H), 8.00 (d, 1H, J=8.7 Hz), 8.08 (m, 2H). MS (DCI/NH$_3$) m/z 344.0 (M+H)$^+$. Anal. Calcd for C$_{18}$H$_{18}$N$_3$SCl: C, 62.87;H, 5.28; N, 12.22. Found: C, 62.71; H, 5.23; N, 12.26.

EXAMPLE 5

1-[(5-chloro-1-benzothien-3-yl)methyl]-4-(2-fluorophenyl)piperazine 3-(Bromomethyl)-5-chloro-1-benzothiophene and 1-(2-fluorophenyl)piperazine were processed as described in Example 2 to provide the title compound. $^1$H NMR ($d_6$-DMSO, 300 MHz) δ 2.65 (m, 2H), 3.02 (m, 6H), 3.78 (s, 2H), 6.92-7.10 (m, 4H), 7.40 (dd, 1H, J=8.7, 1.5), 7.67 (s, 1H), 7.78 (d, 1H, J=8.7 Hz), 8.06 (d, 1H, J=1.5 Hz). MS (DCI/NH$_3$) m/z 361.0 (M+H)$^+$. Anal. Calcd for C$_{19}$H$_{18}$N$_2$SClF: C, 63.24;H, 5.03; N, 7.76. Found: C, 63.17;H, 4.90; N, 7.67.

EXAMPLE 6

2-{4-[(5-chloro-1-benzothien-3-yl)methyl]-1-piperazinyl}pyrimidine 3-(Bromomethyl)-5-chloro-1-benzothiophene and 2-(1-piperazinyl)pyrimidine were processed as described in Example 2 to provide the title compound. $^1$H NMR (CDCl$_3$, 300 MHz) δ (2.62-2.9 (m, 4H), 3.75 (m, 6H), 6.6 (m, 1H), 7.38 (m, 2H), 7.85 (m, 2H), 8.31 (M, 2H). MS (DCI/NH$_3$) m/z 345.0 (M+H)$^+$; Anal. Calcd for C$_{17}$H$_{17}$ClN$_4$S: C, 53.04;H, 4.74; N, 14.55. Found: C, 52.79;H, 4.41; N, 14.55.

EXAMPLE 7

1-(1-benzothien-3-ylmethyl)-4-(2-pyridinyl)piperazine

1-Benzothiophene-3-carbaldehyde (6.17 mmole), 1-(2-pyridinyl)piperazine (6.17 mmole), and sodium triacetoxyborohydride (9.26 mmole) were combined in 25 mL of 1,2-dichloroethane and stirred at 0° C. for one hour. The mixture was allowed to warm to room temperature and stir for 12 hours. The mixture was poured into a diethyl ether:dichloromethane mixture and washed with a solution of saturated aqueous NaCl made basic with sodium hydroxide solution. The organic phase was dried over sodium sulfate, filtered, and the filtrate concentrated under reduced pressure. The residue was purified by flash chromatography with 96:4:0.5 dichloromethane/methanol/saturated aqueous ammonia to provide the title compound. $^1$H NMR (d$_6$-DMSO, 300 MHz) δ 2.62 (t, 4H, J=4.5 Hz), 3.51 (t, 4H, J=4.5 Hz), 3.82 (s, 2H), 6.65 (m, 1H), 6.80 (d, 1H, J=8.7 Hz), 7.40 (m, 2H), 7.48 (s, 1H), 7.53 (m, 1H), 7.86 (m, 1H), 8.04 (m, 2H); MS (DCI/NH$_3$) m/z 310.0 (M+H)$^+$.

EXAMPLE 8

2-[4-(1-benzothien-2-ylmethyl)-1-piperazinyl]benzonitrile

EXAMPLE 8A

1-benzothien-2-ylmethanol

Benzothiophene (5.0 g, 37.3 mmol) in anhydrous THF (100 ml) stirring at −20° C. was treated with n-butyllithium (34 ml, 1.6 M, 55.8 mmol) and stirred for 1 hour. The mixture was cooled to −78° C. and treated with paraformaldehyde (7.8 g, 261 mmol) in four portions. The mixture was allowed to slowly warm to room temperature with stirring overnight. The mixture was treated with 2N HCl (100 ml) and extracted with diethyl ether (2×100 ml). The organic phases were combined, dried over NaSO$_4$, filtered, and the filtrate concentrated under reduced pressure. The residue was crystallized from DCM/hexanes to provide the title compound. $^1$H NMR (300 MHz, CDCl$_3$) δ 4.94 (s, 2H) 7.23 (s, 1H) 7.33 (m, 3H) 7.74 (m, 1H); (ESI) m/z 165 (M+H)$^+$.

EXAMPLE 8B

2-[4-(1-benzothien-2-ylmethyl)-1-piperazinyl]benzonitrile

The product from Example 8A (150 mg 0.9 mmol), methane sulfonic anhydride (159 mg, 0.9 mmol), and D$_1$ EA (475 μL 2.7 mmol) were combined. After stirring, 2-(1-piperazinyl)benzonitrile (181 mg, 1.0 mmol) in 2 ml DCM was also combined and stirred at room temperature for 18 hours. The mixture was concentrated and the residue was taken up in hot methanol. The methanol was filtered and the filter cake washed with cold methanol to provide the title compound. $^1$H NMR (300 MHz, CDCl$_3$) δ 2.69 (m, 4H) 3.04 (s, 4H) 3.76 (m, 4H) 3.86 (s, 1H) 6.74 (m, 2H) 7.29 (m, 3H) 7.75 (m, 1H); (ESI) m/z 334 (M+H)$^+$.

EXAMPLE 9

1-(1-benzothien-2-ylmethyl)-4-(2-fluorophenyl piperazine

The product from Example 8A (150 mg 0.9 mmol), methane sulfonic anhydride (159 mg, 0.9 mmol), and D$_1$ EA (475 μL 2.7 mmol) were combined. After stirring, 1-(2-fluorophenyl)piperazine (181 mg, 1.0 mmol) was also combined and processed as described in Example 8B to provide the title compound. $^1$H NMR (300 MHz, DMSO-d$_6$) δ 2.63 (m, 4H) 3.04 (m, 4H) 3.86 (s, 2H) 7.04 (m, 6H) 7.32 (m, 2H) 7.77 (m, 1H). (ESI) m/z 327 (M+H)$^+$.

EXAMPLE 10

1-(1-benzothien-2-ylmethyl)-4-(2-pyridinyl)piperazine

The product from Example 8A (300 mg 1.8 mmol), methane sulfonic anhydride (313 mg, 1.8 mmol), and D$_1$ EA (200 μL 5.4 mmol) were combined. After stirring, 1-(2-pyridinyl)piperazine (328 mg, 2.9 mmol) in 4 ml DCM was also combined and the mixture was processed as described in Example 8B to provide the title compound. $^1$H NMR (300 MHz, DMSO-d$_6$) δ 2.57 (m, 4H) 3.50 (m, 4H) 3.84 (s, 2H) 6.63 (m, 2H) 6.81 (d, J=8.48 Hz, 1H) 7.32 (m, 2H) 7.52 (m, 2H) 7.77 (m, 1H) 7.90 (m, 1H). (ESI) m/z 310 (M+H)$^+$.

EXAMPLE 11

2-{4-[(5-fluoro-1H-indol-2-yl)methyl]-1,4-diazepan-1-yl}benzonitrile

EXAMPLE 11A tert-butyl 4-[(5-fluoro-1H-indol-2-yl)carbonyl]-1,4-diazepane-1-carboxylate tert-Butyl 1,4-diazepane-1-carboxylate (2.0 g, 10 mmol, Aldrich), 5-fluoro-1H-indole-2-carboxylic acid (1.79 g, 10 mmol, Aldrich), and EDCI (1.92 g, 10 mmol) were combined in CH$_2$Cl$_2$ (30 mL) at room temperature and stirred for 24 hours. The mixture was concentrated under reduced pressure and the residue was purified by flash chromatography (5% MeOH/CH$_2$Cl$_2$) to provide the title compound. $^1$H NMR (CD$_3$OD, 300 MHz) δ 1.46 (s, 9H), 1.86-2.14 (m, 2H), 3.40-3.58 (m, 2H), 3.62-3.72 (m, 2H), 3.75-4.05 (m, 4H), 6.78 (s, 1H), 6.99-7.09 (m, 1H), 7.28-7.35 (m, 2H); MS (DCI/NH3) m/z 362 (M+H)$^+$.

EXAMPLE 11B tert-butyl 4-[(5-fluoro-1H-indol-2-yl)methyl]-1,4-diazepane-1-carboxylate

The product from Example 11 A (0.56 g, 1.60 mmol) in THF (20 mL) was treated with LAH (4.70 mmol) and stirred at room temperature for 2 hours. The mixture was treated with a saturated solution of $Na_2SO_4$, dried ($MgSO_4$), filtered and the filtrate was concentrated under reduced pressure to provide the title compound which was used in the next step without further purification. $^1H$ NMR ($CD_3OD$, 300 MHz) δ 1.48 (s, 9H), 1.82-1.95 (m, 4H), 2.60-2.68 (m, 2H), 3.41-3.56 (m, 4H), 3.75 (s, 2H), 6.29 (s, 1H), 6.85-6.93 (m, 1H), 7.12-7.28 (m, 2H); MS (DCI/NH3) m/z 348 (M+H)$^+$.

EXAMPLE 11C 2-(1,4-diazepan-1-ylmethyl)-5-fluoro-1H-indole

The product from Example 11B (0.48 g, 1.40 mmol) in $CH_2Cl_2$ (20 mL) was treated with TFA (20 mL) and stirred for 1 hour. The mixture was concentrated under reduced pressure and the residue was purified by flash chromatography (10% $MeOH/CH_2Cl_2/1\%$ $NH_4OH$) to provide the title compound. $^1H$ NMR ($CD_3OD$, 300 MHz) δ 1.85-1.98 (m, 4H), 2.58-2.68 (m, 2H), 3.45-3.57 (m, 4H), 3.67 (s, 2H), 6.25 (s, 1H), 6.75-6.90 (m, 1H), 7.10-7.25 (m, 2H); MS (DCI/NH3) m/z 248 (M+H)$^+$.

EXAMPLE 11D

2-{4-[(5-fluoro-1H-indol-2-yl)methyl]-1,4-diazepan-1-yl}benzonitrile

The product from Example 11C (0.38 g, 1.5 mmol) and 2-bromobenzonitrile (0.28 g, 1.5 mmol, Aldrich) in toluene (15 mL) were treated with $Pd_2(DBA)_3$ (0.028 g, 0.04 mmol), BINAP (0.038 g, 0.10 mmol), and $CsCO_3$ (0.99 g, 3.0 mmol) with stirring at 90° C. for 48 hours. The mixture was allowed to cool to room temperature, filtered, and the filtrate was concentrated under reduced pressure. The residue was purified by flash chromatography (5% $MeOH/CH_2Cl_2$) to provide the title compound. The maleate salt was formed and recrystallization from ethanol/diethyl ether. $^1H$ NMR ($CD_3OD$, 300 MHz) δ 2.26-2.78 (m, 2H), 3.47-3.55 (m, 2H), 3.59-3.65 (m, 2H), 3.67-3.80 (m, 4H), 4.61 (s, 2H), 6.75 (s, 1H), 6.85-7.08 (m, 2H), 7.15 (d, J=9.0 Hz, 1H), 7.26 (dd, J=2.0, 8.0 Hz, 1H), 7.36-7.42 (m, 1H), 7.50-7.66 (m, 2H). m/z 349 (M+H)$^+$. Mp 194-198° C. Anal. Calcd for $C_{21}H_{21}N_4F·2.4$ $C_4H_4O_4$ 1.0 MeOH: C, 57.59;H, 5.29; N, 8.50. Found: C, 57.91;H, 5.10; N, 8.37.

EXAMPLE 12

2-{1-[4-(2-methoxyphenyl)-1-piperazinyl]ethyl}-1H-indole 1-(1H-indol-2-yl)ethanone and 1-(2-methoxyphenyl)piperazine were processed as described in Example 7. The residue was purified by preparative HPLC on a Waters Nova-PakHR C18 column (25 mm×100 mm, 6 um particle size) using a gradient of 10% to 100% acetonitrile: 0.1% aqueous TFA over 8 minutes at a flow rate of 40 mL/minutes to provide the title compound. MS (DCI/NH$_3$) m/z 336 (M+H)$^+$.

EXAMPLE 13

2-{[4-(2-methoxyphenyl)-1-piperazinyl]methyl}-1-methyl-1H-indole

1-Methyl-1H-indole-2-carbaldehyde and 1-(2-methoxyphenyl)piperazine were processed as described in Example 7 to provide the title compound. $^1H$ NMR ($CD_3OD$, 300 MHz) δ 3.0 (m, 2H), 3.45 (m, 2H), 3.74 (m, 4H), 3.86 (s, 3H), 3.88 (s, 2H), 4.70 (s, 3H), 6.83 (s, 1H), 6.90-7.14 (m, 5H), 7.28 (m, 1H), 7.48 (d, 1H, J=7.8 Hz), 7.62 (d, 1H, J=7.8 Hz). MS (DCI/NH$_3$) m/z 336.1 (M+H)$^+$. Anal. Calcd for $C_{21}H_{25}N_3O$: C, 75.19;H, 7.51; N, 12.53. Found: C, 74.45;H, 7.43; N, 12.37.

EXAMPLE 14

2-{1-[4-(2-pyridinyl)-1-piperazinyl]ethyl}-1H-indole 1-(1H-indol-2-yl)ethanone and 1-(2-pyridinyl)piperazine were processed as described in Example 7. The residue was purified by preparative HPLC on a Waters Nova-PakHR C18 column (25 mm×100 mm, 6 um particle size) using a gradient of 10% to 100% acetonitrile: 0.1% aqueous TFA over 8 minutes at a flow rate of 40 mL/minutes to provide the title compound. $^1H$ NMR ($CD_3OD$, 300 MHz) δ 1.90 (d, 3H, J=6.8 Hz), 3.37 (m, 4H), 3.85 (m, 4H), 4.6 (sm, 1H), 6.73 (s, 1H), 6.90 (t, 1H, J=7.8 Hz), 7.06 (m, 2H), 7.19 (t, 1H, J=8.1 Hz), 7.43 (d, 1H, J=8.1 Hz), 7.58 (d, 1H, J=8.1 Hz), 7.79 (m, 1H), 8.08 (m, 1H); MS (DCI/NH$_3$) m/z 307 (M+H)$^+$.

EXAMPLE 15

5-fluoro-2-{[(1S,4S)-5-(2-pyridinyl)-2,5-diazabicyclo[2.2.1]hept-2-yl]methyl}-1H-indole

EXAMPLE 15A tert-butyl (1S,4S)-5-(2-pyridinyl)-2,5-diazabicyclo[2.2.1]heptane-2-carboxylate tert-Butyl (1S,4S)-2,5-diazabicyclo[2.2.1]heptane-2-carboxylate (1.0 g, 5.10 mmol, Aldrich) in 1,4-dioxane (10 mL) in a sealed tube was treated with 2-bromopyridine (0.40 g, 2.50 mmol, Aldrich) and heated at 150° C. for 12 hours. The mixture was allowed to cool to room temperature and was concentrated under reduced pressure. The residue was purified by flash chromatography (5% $MeOH/CH_2Cl_2$) to provide the title compound. $^1H$ NMR ($CDCl_3$, 300 MHz) δ 1.48 (m, 9H), 1.86-1.94 (m, 2H), 3.30-3.58 (m, 4H), 4.52 (brs, 0.5H), 4.67 (brs, 0.5H), 4.80 (brs, 0.5H), 4.92 (brs, 0.5H), 6.32 (d, J=9.0 Hz, 1H), 6.57 (t, J=6.0 Hz, 1H), 7.38-7.55 (m, 1H), 8.12 (d, J=6.0 Hz, 1H). MS (DCI/NH3) m/z 276 (M+H)$^+$.

EXAMPLE 15B (1S,4S)-2-(2-pyridinyl)-2,5-diazabicyclo[2.2.1]heptane

The product from Example 15A (0.52 g, 1.90 mmol) in $CH_2Cl_2$ (20 mL) was treated with TFA (20 mL) and stirred for 1 hour. The mixture was concentrated under reduced pressure. The residue was purified by flash chromatography (10% $MeOH/CH_2Cl_2/1\%$ $NH_4OH$) to provide the title compound. $^1H$ NMR ($CDCl_3$, 300 MHz) δ 1.90-1.98 (m, 2H), 3.25-3.51 (m, 4H), 4.50-4.62 (m, 2H), 6.32 (d, J=9.0 Hz, 1H), 6.57 (t, J=6.0 Hz, 1H), 7.38-7.55 (m, 1H), 8.12 (d, J=6.0 Hz, 1H); MS (DCI/NH3) m/z 176 (M+H)$^+$.

EXAMPLE 15C 5-fluoro-2-{[(1S,4S)-5-(2-pyridinyl)-2,5-diazabicyclo[2.2.1]hept-2-yl]carbonyl}-1H-indole The product from Example 15B (0.40 g, 1.5 mmol) in $CH_2Cl_2$ (30 mL) was treated with 5-fluoro-1H-indole-2-carboxylic acid (0.26 g, 1.5 mmol, Aldrich) and EDCI (0.26 g, 1.5 mmol) and stirred at room temperature for 24 hours. The mixture was concentrated under reduced pressure. The residue was purified by flash chromatography (10% MeOH/CH$_2$Cl$_2$) to provide the title compound. $^1$H NMR (CDCl$_3$, 300 MHz) δ 1.80-2.22 (m, 2H), 3.10-3.25 (m, 2H), 3.35-3.59 (m, 4H), 6.30 (m, 1H), 6.50-6.65 (m, 1H), 6.70 (s, 1H), 6.95-7.10 (m, 1H), 7.35-7.40 (m, 1H), 7.40-7.50 (m, 2H), 8.10 (d, J=8.0 Hz, 1H). m/z 337 (M+H)$^+$.

EXAMPLE 15D 5-fluoro-2-{[(1S,4S)-5-(2-pyridinyl)-2,5-diazabicyclo[2.2.1]hept-2-yl]methyl}-1H-indole The product from Example 15C in THF solution (30 mL) was treated with LAH (5.50 mmol) and stirred at room temperature for 2 hours. The mixture was treated with Na$_2$SO$_4$ decahydrate, filtered and the filtrate concentrated under reduced pressure. The residue was purified by flash chromatography (10% MeOH/CH$_2$Cl$_2$) to provide the title compound. The maleate salt was formed and recrystallization from ethanol/diethyl ether. $^1$H NMR (CD$_3$OD, 300 MHz) δ 2.22-2.36 (m, 2H), 3.45-3.62 (m, 2H), 3.70 (s, 2H), 4.45-4.58 (m, 3H), 4.95 (s, 1H), 6.23 (s, 1H), 6.62-6.65 (m, 1H), 6.70 (t, J=3.0 Hz, 1H), 6.95 (dt, J=2.0, 6.0 Hz, 1H), 7.22 (dd, J=2.0, 8.0 Hz, 1H), 7.40-7.45 (m, 1H), 7.60 (t, J=2.0 Hz, 1H), 8.05 (d, J=2.0 Hz, 1H); MS (DCI/NH3) m/z 322 (M+H)$^+$. Mp 211-214° C. Anal. Calcd for C$_{19}$H$_{19}$N$_4$F.1.3 C$_4$H$_4$O$_4$: C, 61.82;H, 5.36; N, 11.38. Found: C, 61.88;H, 4.99; N, 11.28.

EXAMPLE 16

5-fluoro-2-{[4-(2-pyridinyl)-1,4-diazepan-1-yl]methyl}-1H-indole

EXAMPLE 16A tert-butyl 4-(2-pyridinyl)-1,4-diazepane-1-carboxylate tert-Butyl 1,4-diazepane-1-carboxylate (5.0 g, 25.0 mmol) (Aldrich) and 2-bromopyridine (1.98 g, 12.50 mmol) (Aldrich) were combined in a sealed tube and heated at 150° C. for 12 hours. The mixture was purified by flash chromatography (5% MeOH/CH$_2$Cl$_2$) to provide the title compound. $^1$H NMR (CDCl$_3$, 300 MHz) δ 1.48 (m, 9H), 1.88-2.02 (m, 2H), 3.20-3.48 (m, 2H), 3.52-3.70 (m, 4H), 3.72-3.83 (m, 2H), 6.45-6.59 (m, 2H), 7.47 (m, 2H), 8.11-8.18 (m, 1H); MS (DCI/NH3) m/z 278 (M+H)$^+$.

EXAMPLE 16B 1-(2-pyridinyl)-1,4-diazepane

The product from Example 16A (1.0 g, 4.00 mmol) in CH$_2$Cl$_2$ (10 mL) was treated with TFA (10 mL) and stirred for 1 hour. The mixture was concentrated under reduced pressure. The residue was purified by flash chromatography (10% MeOH/CH$_2$Cl$_2$/1% NH$_4$OH) to provide the title compound. $^1$H NMR (CDCl$_3$, 300 MHz) δ 1.85-2.00 (m, 2H), 3.25-3.43 (m, 2H), 3.50-3.83 (m, 6H), 6.52-6.60 (m, 2H), 7.45 (m, 1H), 8.00 (m, 1H); MS (DCI/NH3) m/z 178 (M+H)$^+$.

EXAMPLE 16C 5-fluoro-2-{[4-(2-pyridinyl)-1,4-diazepan-1-yl]carbonyl}-1-1H-indole The product from Example 16B (0.68 g, 3.8 mmol) in CH$_2$Cl$_2$ (25 mL) was treated with 5-fluoro-1H-indole-2-carboxylic acid (0.68 g, 3.8 mmol, Aldrich) and EDCI (0.73 g, 3.8 mmol) and stirred at room temperature for 48 hours. The mixture was concentrated under reduced pressure. The residue was purified by flash chromatography (10% MeOH/CH$_2$Cl$_2$) to provide the title compound. $^1$H NMR (CDCl$_3$, 300 MHz) δ 2.01-2.22 (m, 2H), 3.65-4.21 (m, 8H), 6.56 (d, J=9.0 Hz, 2H), 6.78 (s, 1H), 7.10 (t, J=3.0 Hz, 1H), 7.27-7.39 (m, 2H), 7.42 (t, J=3.0 Hz, 1H), 8.10-8.20 (m, 1H); MS (DCI/NH3) m/z 338 (M+H)$^+$.

EXAMPLE 16D 5-fluoro-2-{[4-(2-pyridinyl)-1 4-diazepan-1-yl]methyl}-1H-indole

The product from Example 16C in THF solution (10 mL) was treated with LAH (0.90 mmol of 1 M) and stirred at room temperature for 2 hours. The mixture was treated with Na$_2$SO$_4$ decahydrate, filtered, and the filtrate concentrated under reduced pressure. The residue was purified by flash chromatography (10% MeOH/CH$_2$Cl$_2$) to provide the title compound. The maleate salt was formed and recrystallization from ethanol/diethyl ether as a white solid. $^1$H NMR (CD$_3$OD, 300 MHz) δ 2.23-2.32 (m, 2H), 3.35-3.47 (m, 4H), 3.67 (t, J=9.0 Hz, 2H), 3.97-4.08 (m, 2H), 4.45 (s, 2H), 6.25 (s, 1H), 6.63-6.81 (m, 2H), 6.98 (dt, J=2.0, 6.0 Hz, 1H), 7.22 (dd, J=2.0, 6.0 Hz, 1H), 7.33-7.42 (m, 1H), 7.60 (t, J=6.0 Hz, 1H), 8.08 (d, J=3.0 Hz, 1H).MS (DCI/NH3) m/z 325 (M+H)$^+$. Anal. Calcd for C$_{19}$H$_{21}$N$_4$F.1.2 C$_4$H$_4$O$_4$ 0.20H$_2$O: C, 60.28; H, 5.59; N, 12.33. Found: C, 60.52;H, 5.65; N, 12.62

EXAMPLE 17

5-fluoro-2-{[4-(2-pyridinyl)-1-piperazinyl]methyl}-1H-indole

EXAMPLE 17A 5-fluoro-2-{[4-(2-pyridinyl)-1-piperazinyl]carbonyl}-1H-indole

5-Fluoro-1H-indole-2-carboxylic acid (4.0 g) and EDCI (4.29 g) were combined in dichloromethane (90 mL) and treated with 1-(2-pyridinyl)piperazine (3.64 g). After stirring at 25° C. for 24 hours, the mixture was washed with 150 mL of water and filtered. The filter cake was washed in succession with 300 mL of water, 250 mL of dichloromethane and 20 mL of ethyl acetate to provide the title compound. $^1$H NMR (d$_6$-DMSO, 300 MHz) δ 3.61 (m, 4H), 3.85 (m, 4H), 6.67 (dd, 1H, J=7.5, 4.8 Hz), 6.85 (m, 2H), 7.06 (m, 1H), 7.40 (m, 2H), 7.65 (m, 1H), 8.04 (dd, 1H, J=4.5, 1.8 Hz), 11.72 (bs, 1H). MS (DCI/NH$_3$) m/z 325 (M+H)$^+$.

EXAMPLE 17B 5-fluoro-2-{[4-(2-pyridinyl)-1-piperazinyl]methyl}-1H-indole

The product from Example 17A (3.50 g) in tetrahydrofuran (50 mL) was treated with lithium aluminum hydride (30 mmol). The mixture was treated by sequential addition of 1.14 mL of water, 1.14 mL of 15% aqueous sodium hydroxide, and 3.42 mL of water. The slurry was filtered and the filtrate diluted with ethanol and then concentrated under reduced pressure. The residue was filtered through a plug of silica gel, then purified by chromatography on silica gel, eluting with ethyl acetate containing 0.1% ammonium hydroxide to provide the title compound. $^1$H NMR (d$_6$-DMSO, 300 MHz) δ 2.55 (m, 4H), 3.50 (t, 4H, J=4.5 Hz), 3.65 (s, 2H), 6.30 (s, 1H), 6.63 (dd, 1H, J=7.5, 4.8 Hz), 6.80

(d, 1H, J=7.5 Hz), 6.85 (m, 1H), 7.20 (dd, 1H, J=10.5, 2.4 Hz), 7.30 (dd, 1H, J=9, 5.4 Hz), 7.50 (m, 1H), 8.09 (dd, 1H, J=4.5, 1.8 Hz), 11.72 (bs, 1H). MS (DCI/NH$_3$) m/z 311 (M+H)$^+$. The free base was dissolved in 45 mL of methanol, along with 1.0 equivalent of maleic acid. Addition of toluene, then evaporation under reduced pressure gave a glass, which was covered with 25 mL of ether, which yielded crystals when a small amount of methanol was added. Evaporation of solvent, followed by recrystallization of the resulting solid from 15 mL of methanol, 15 mL of toluene, and 200 mL of ether, gave 3.11 g (88% from the free base) of 5-Fluoro-2-(4-pyridin-2-yl-piperazin-1-ylmethyl)-1H-indole maleate. Anal. Calcd for C$_{18}$H$_{19}$N$_4$F.C$_4$H$_4$O$_4$: C, 61.96;H, 5.44; N, 13.14. Found: C, 61.89;H, 5.36; N, 13.12.

EXAMPLE 18

2-[4-(1H-pyrrolo[2,3-b]pyridin-2-ylmethyl)-1-piperazinyl]benzonitrile 1H-pyrrolo[2,3-b]pyridine (47 mg, 0.40 mmol), 2-(1-piperazinyl)benzonitrile (65 mg, 0.48 mmol), sodium acetate (72 mg, 0.53 mmol), and formaldehyde (0.48 mmol) were combined in water and glacial acetic acid (1:2, 1 mL) and stirred at room temperature for 18 hours. The mixture was treated with a solution of 2M NaOH and concentrated under reduced pressure. The residue was treated with hot methanol. The methanol was filtered and the filter cake was washed with cold methanol to provide the title compound. $^1$H NMR (300 MHz, DMSO-d$_6$) δ 2.62 (m, 4H) 3.14 (m, 4H) 4.03 (s, 2H) 5.60 (s, 1H) 7.09 (m, 3H) 7.61 (m, 2H) 8.06 (dd, J=8.31, 1.53 Hz, 1H) 8.20 (dd, J=4.75, 1.70 Hz, 1H). (ESI) m/z 318 (M+H)$^+$.

EXAMPLE 19

2-{[4-(2-pyrimidinyl)-1-piperazinyl]methyl}-1H-pyrrolo[2,3-b]pyridine 1H-pyrrolo[2,3-b]pyridine (47 mg, 0.40 mmol), 2-(1-piperazinyl)pyrimidine (65 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.42 (m, 4H) 3.68 (m, 4H) 4.05 (s, 2H) 5.59 (s, 1H) 6.60 (m, 1H) 7.08 (m, 2H) 7.37 (m, 2H 8.07 (m, 2H). (ESI) m/z 295 (M+H)$^+$.

EXAMPLE 20

2-{[4-(2-methoxyphenyl)-1-piperazinyl]methyl}-1H-pyrrolo[2,3-b]pyridine 1H-pyrrolo[2,3-b]pyridine (47 mg, 0.40 mmol), 1-(2-methoxyphenyl)piperazine (65 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.97 (m, 4H) 3.68 (m, 4H) 3.72 (s, 3H) 4.05 (s, 2H) 5.60 (m, 1H) 6.60 (m, 1H), 6.89 (m, 2H) 7.08 (ddd, J=21.36, 7.80, 4.75 Hz, 1H) 7.52 (m, 2H) 8.07 (m, 2H) (ESI) m/z 323 (M+H)$^+$.

EXAMPLE 21

2-{[4-(2-pyridinyl)-1-piperazinyl]methyl}-1H-pyrrolo[2,3-b]pyridine 1H-pyrrolo[2,3-b]pyridine (47 mg, 0.40 mmol), 1-(2-pyridinyl)piperazine (65 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.49 (m, 4H) 3.45 (m, 4H) 3.67 (s, 2H) 5.59 (s, 1H) 6.60 (dd, J=6.78, 5.09 Hz, 1H) 6.77 (d, J=8.82 Hz, 1H) 7.04 (dd, J=7.97, 4.58 Hz, 1H) 7.49 (m, 2H) 8.06 (m, 1H) 8.19 (dd, J=4.75, 1.70 Hz, 1H) (ESI) 294 m/z (M+H)$^+$.

EXAMPLE 22

2-[(4-phenyl-1-piperazinyl)methyl]-1H-pyrrolo[2,3-b]pyridine 1H-pyrrolo[2,3-b]pyridine (47 mg, 0.40 mmol),1-phenylpiperazine (64.9 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.62 (m, 4H) 3.14 (m, 4H) 4.03 (s, 2H) 5.60 (s, 1H) 7.09 (m, 3H) 7.84 (m, 3H) 8.06 (dd, J=8.31, 1.53 Hz, 1H) 8.20 (dd, J=4.75, 1.70 Hz, 1H). (ESI) m/z 293 (M+H)$^+$.

EXAMPLE 23

2-{[4-(2-fluorophenyl)-1-piperazinyl]methyl}-1H-pyrrolo[2,3-b]pyridine 1H-pyrrolo[2,3-b]pyridine (47 mg, 0.40 mmol), 1-(2-fluorophenyl)piperazine (72.0 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.62 (m, 4H) 3.14 (m, 4H) 4.03 (s, 2H) 5.60 (s, 1H) 7.09 (m, 3H) 7.14 (m, 2H) 8.06 (dd, J=8.31, 1.53 Hz, 1H) 8.20 (dd, J=4.75, 1.70 Hz, 1H). (ESI) m/z 311 (M+H)$^+$.

EXAMPLE 24

2-[4-(1H-pyrrolo[2,3-b]pyridin-2-ylmethyl)-1-piperazinyl]nicotinonitrile 1H-pyrrolo[2,3-b]pyridine (47 mg, 0.40 mmol), 2-(1-piperazinyl)nicotinonitrile (75 mg, 0.48 mmol), sodium acetate (72 mg, 0.53 mmol), and formaldehyde (0.48 mmol) were processed as described in Example 18 to provide the title compound. $^1$H NMR (300 MHz, DMSO-d$_6$) δ 2.57 (m, 4H) 3.50 (m, 4H) 3.84 (s, 2H) 6.63 (m, 2H) 6.81 (m, 1H) 7.32 (m, 1H) 7.52 (m, 1H) 7.77 (m, 1H) 7.90 (m, 1H). (ESI) m/z 319 (M+H)$^+$.

EXAMPLE 25

4-(4-{[6-(trifluoromethyl)thieno[3,2-b]pyridin-2-yl]methyl}-1-piperazinyl)phenol

EXAMPLE 25A ethyl 6-(trifluoromethyl)thieno[3,2-b]pyridine-2-carboxylate

3-Chloro-5-(trifluoromethyl)-2-pyridinecarbaldehyde (Chemical Abstracts number 175277-50-6, purchase from Maybridge), potassium carbonate (4.95 g), and ethyl mercaptoacetate (2.52 g) were combined in N,N-dimethylformamide (25 mL) at 25° C. and stirred for 18 hours. The mixture was then heated at 50° C. for 6 hours, allowed to cool to room temperature, poured into a mixture of diethyl ether (80 mL)

and dichloromethane (25 mL), and washed with aqueous sodium carbonate. The organic phase was dried over sodium sulfate, filtered, and the filtrate concentrated under reduced pressure. The residue was dissolved in dichloromethane and filtered to remove solids. The filtrate was concentrated and the residue purified by flash chromatography (dichloromethane) to provide the title compound. MS (DCI/NH$_3$) m/z 276.0 (M+H)$^+$.

EXAMPLE 25B

[6-(trifluoromethyl)thieno[3,2-b]pyridin-2-yl]methanol

The product from Example 25A (2.80 g) in tetrahydrofuran (20 mL) and ethanol (20 mL) was treated with sodium borohydride (0.388 g) at 25° C. After stirring for 24 hours, the mixture was treated with additional sodium borohydride (1 g) and additional ethanol. After an additional 24 hours, the mixture was poured into 0.2% NH$_4$OH (200 mL) and extracted with dichloromethane. The organic phase was washed with water and concentrated under reduced pressure. The residue was purified by flash chromatography (97:3:0.1 dichloromethane:methanol:sat. NH$_4$OH solution) to provide the title compound. $^1$H NMR (CDCl$_3$, 300 MHz) δ 5.02 (s, 2H), 7.48 (s, 1H), 8.36 (s, 1H), 8.87 (s, 1H). MS (DCI/NH$_3$) m/z 234 (M+H)$^+$.

EXAMPLE 25C

[6-(trifluoromethyl)thieno[3,2-b]pyridin-2-yl]methyl methanesulfonate

The product from Example 25B (732 mg) and methanesulfonic anhydride (547 mg) were combined and cooled to 0° C. The mixture was treated with dichloromethane (22 mL) and N,N-diisopropylethylamine (0.66 mL). After 30 minutes, the solution was used to in the next step.

EXAMPLE 25D 4-(4-{[6-(trifluoromethyl)thieno[3,2-b]pyridin-2-yl]methyl}-1-piperazinyl)phenol The solution from Example 25C (2 mL) was treated with 4-(1-piperazinyl)phenol (178 mg) in DMSO (1 mL). After 72 hours, the mixture was concentrated under a stream of nitrogen gas and the residue recrystallized from DMSO:methanol (1:1) to provide the title compound. $^1$H NMR (CDCl$_3$, 300 MHz) δ 2.81 (4H, t, J=4.8 Hz), 3.18 (4H, J=4.8 Hz), 3.95 (s, 2H), 6.78 (2H, d, J=9 Hz), 6.90 (2H, J=9 Hz), 7.48 (1H, s), 8.38 (1H, m), 8.80 (1H, m). MS (DCI/NH$_3$) m/z 394 (M+H)$^+$. Anal. Calcd for C$_{19}$H$_{18}$N$_3$F$_3$OS: C, 56.72;H, 4.76; N, 10.44. Found: C, 56.43;H, 4.50; N, 10.35.

EXAMPLE 26

2-{[4-(2-methoxyphenyl)-1-piperazinyl]methyl}-6-(trifluoromethyl)thieno[3,2-b]pyridine The solution from Example 25C (2 mL) and 1-(2-methoxyphenyl)piperazine (192 mg) were processed as described in Example 25D to provide the title compound. $^1$H NMR (CDCl$_3$, 300 MHz) δ 3.11 (4H, t, J=4.8 Hz), 3.45 (4H, J=4.8 Hz), 4.19 (s, 3H), 4.30 (s, 2H), 6.90 (4H, m), 7.80 (1H, s), 8.63 (1H, m), 9.20 (1H, m). MS (DCI/NH$_3$) m/z 408.2 (M+H)$^+$. Anal. Calcd for C$_{20}$H$_{20}$N$_3$F$_3$OS: C, 58.96;H, 4.95; N, 10.31. Found: C, 58.98;H, 4.95; N, 10.53.

EXAMPLE 27

2-(4-[[6-(trifluoromethyl)thieno[3,2-b]pyridin-2-yl]methyl]-1-piperazinyl)benzonitrile The solution from Example 25C (2 mL) and 2-(1-piperazinyl)benzonitrile (187 mg) were processed as described in Example 25D to provide the title compound. $^1$H NMR (CDCl$_3$, 300 MHz) δ 2.81 (4H, t, J=4.8 Hz), 3.29 (4H, J=4.8 Hz), 4.00 (s, 2H), 7.03 (2H, m), 7.50 (2H, m), 7.59 (dd, 1H, J=7.5, 1.5 Hz), 8.39 (1H, m), 8.86 (1H, m). MS (DCI/NH$_3$) m-z 403.1 (M+H)$^+$. Anal. Calcd for C$_{20}$H$_{17}$N$_4$F$_3$S: C, 59.69; H, 4.26; N, 13.92. Found: C, 59.53;H, 4.12; N, 14.22.

EXAMPLE 28

4-[4-(furo[3,2-b]pyridin-2-ylmethyl)-1-piperazinyl]phenol

The product from Example 35B, 4-(1-piperazinyl)phenol, and sodium triacetoxyborohydride were processed as described in Example 35C to provide the title compound. $^1$H NMR (CDCl$_3$, 300 MHz) δ 2.83 (br, 4H), 3.16 (br, 4H), 3.88 (s, 2H), 6.77 (m, J=2.03, 8.81 Hz, 2H), 6.89 (m, 3H), 7.25 (dd, J=4.75, 8.48 Hz, 1H), 7.80 (d, J=8.48 Hz, 1H), 8.48 (m, J=1.02, 8.48 Hz, 1H); MS (DCI/NH$_3$) m/z 310.1 (M+H)$^+$.

EXAMPLE 29

2-[(4-phenyl-1-piperazinyl)methyl]furo[3,2-b]pyridine

The product from Example 35B, 1-phenylpiperazine, and sodium triacetoxyborohydride were processed as described in Example 35C to provide the title compound. $^1$H NMR (CDCl$_3$, 300 MHz) δ 2.78 (br, 4H), 3.28 (br, 4H), 3.85 (s, 2H), 6.89 (m, 4H), 7.20 (dd, J=4.75, 8.14 Hz, 1H), 7.26 (m, 2H), 7.73 (d, J=8.14 Hz, 1H), 8.54 (br, 1H); MS (DCI/NH$_3$) m/z 294.2 (M+H)$^+$; Anal Calcd for C$_{18}$H$_{19}$N$_3$O: C, 73.69;H, 6.53; N, 14.32. Found: C, 72.19;H, 6.43; N, 14.09.

EXAMPLE 30

2-{[4-(2-methoxyphenyl)-1-piperazinyl]methyl}furo[3,2-b]pyridine

The product from Example 35B, 1-(2-methoxyphenyl)piperazine, and sodium triacetoxyborohydride were processed as described in Example 35C to provide the title compound. $^1$H NMR (CDCl$_3$, 300 MHz) δ 2.85 (br, 4H), 3.19 (br, 4H), 3.85 (s, 3H), 3.88 (s, 2H), 6.93 (m, 5H), 7.20 (dd, 4.75, 8.14 Hz, 1H), 7.74 (m, J=1.02, 7.12 Hz, 1H), 8.54 (br, 1H); MS (DCI/NH$_3$) m/z 324.2 (M+H)$^+$; Anal Calcd for C$_{19}$H$_{21}$N$_3$O$_2$: C, 70.57;H, 6.55; N, 12.99. Found: C, 69.72;H, 6.45; N, 12.81.

EXAMPLE 31

2-[4-(furo[32-b]pyridin-2-ylmethyl)-1-piperazinyl]benzonitrile

The product from Example 35B, 2-(1-piperazinyl)benzonitrile, and sodium triacetoxyborohydride were processed as described in Example 35C to provide the title compound.

¹H NMR (CDCl₃, 400 MHz) δ 2.87 (m, 4H), 3.32 (m, 4H), 3.89 (s, 2H), 6.92 (s, 1H), 7.02 (m, 2H), 7.20 (dd, J=4.60, 8.29 Hz, 1H), 7.48 (m, J=1.84, 7.24, 8.65 Hz, 1H), 7.56 (dd, J=1.84, 7.98 Hz, 1H), 7.75 (m, J=1.23, 8.29 Hz, 1H), 8.53 (dd, J=1.23, 4.91 Hz, 1H); MS (DCI/NH₃) m/z 319.2 (M+H)⁺; Anal Calcd for C₁₉H₁₈N₄O: C, 71.68;H, 5.70; N, 17.60. Found: C, 70.87;H, 5.90; N, 17.01.

EXAMPLE 32

2-{[4-(3-methyl-2-pyridinyl)-1-piperazinyl]methyl}furo[3,2-b]pyridine

The product from Example 35B, 1-(3-methyl-2-pyridinyl)piperazine, and sodium triacetoxyborohydride were processed as described in Example 35C to provide the title compound. ¹H NMR (CDCl₃, 300 MHz) δ 2.68 (m, 4H), 3.29 (s, 3H), 3.58 (m, 4H), 3.79 (s, 2H), 6.41 (d, J=8.48 Hz, 1H), 6.49 (d, J=7.12 Hz, 1H), 6.85 (s, 1H), 7.18 (dd, J=4.75, 8.14 Hz, 1H), 7.36 (dd, J=7.12, 8.14 Hz, 1H), 7.73 (dd, J=1.02, 8.14 Hz, 1H), 8.51 (dd, J=1.36, 4.75 Hz, 1H); MS (DCI/NH₃) m/z 309.2 (M+H)⁺.

EXAMPLE 33

2-[4-(furo[3,2-b]pyridin-2-ylmethyl)-1-piperazinyl]nicotinonitrile

The product from Example 35B, 2-(1-piperazinyl)nicotinonitrile, and sodium triacetoxyborohydride were processed as described in Example 35C to provide the title compound. ¹H NMR (CDCl₃, 300 MHz) δ 2.78 (br, 4H), 3.82 (br, 6H), 6.75 (dd, J=4.75, 7.80 Hz, 1H), 6.90 (s, 1H), 7.21 (dd, J=4.75, 8.14 Hz, 1H), 7.75 (m, J=1.02, 8.14 Hz, 1H), 7.77 (dd, 2.03, 7.46 Hz, 1H), 8.33 (dd, J=2.03, 4.75 Hz, 1H), 8.54 (d, J=4.41 Hz, 1H); MS (DCI/NH₃) m/z 320.2 (M+H)⁺.

EXAMPLE 34

2-{[4-(2-pyridinyl)-1-piperazinyl]methyl}furo[3,2-b]pyridine

The product from Example 35B, 1-(2-pyridinyl)piperazine, and sodium triacetoxyborohydride were processed as described in Example 35C to provide the title compound. ¹H NMR (CDCl₃, 300 MHz) δ 2.71 (br, 4H), 3.63 (br, 4H), 3.81 (s, 2H), 6.63 (m, 1H), 6.65 (d, J=8.48 Hz), 6.87 (s, 1H), 7.19 (dd, J=4.75, 8.14 Hz, 1H), 7.47 (m, J=2.03, 7.12, 8.48 Hz, 1H), 7.72 (d, J=8.48 Hz, 1H), 8.18 (m, J=2.03, 5.09 Hz, 1H), 8.52 (d, J=4.07 Hz, 1H); MS (DCI/NH₃) m/z 295.2 (M+H)⁺; Anal Calcd for C₁₇H₁₈N₄O: C, 69.37;H, 6.16; N, 19.03. Found: C, 69.38;H, 5.96; N, 18.89.

EXAMPLE 35

2-{[4-(2-fluorophenyl)-1-piperazinyl]methyl}furo[3,2-b]pyridine

EXAMPLE 35a 2-(diethoxymethyl)furo[3,2-b]pyridine

2-Iodo-3-pyridinol (24 mmol), triethylamine (1.0 eq), 3,3-diethoxy-1-propyne (1.0 eq), bis(triphenylphosphine)palladium (II) chloride (0.02 eq), and copper(I) iodide (0.04 eq) were combined in DMF (14 mL) and allowed to stir for 17 hours. The mixture was diluted with ethyl acetate (100 mL) and filtered through a Celite pad. The filtrate was washed with saturated sodium bicarbonate (2×50 mls), dried over anhydrous magnesium sulfate, filtered, and the filtrate concentrated under reduced pressure to provide the title compound which was used in the next step without further purification. ¹H NMR (CDCl₃, 400 MHz) δ 1.28 (t, J=7.1 Hz, 6H), 3.70 (q, J=7.1 Hz, 4H), 5.68 (s, 1H), 7.05 (s, 1H), 7.23 (dd, J=8.5, 4.8 Hz, 1H), 7.77 (d, J=8.5 Hz, 1H), 8.57 (br, 1H). MS (DCI/NH₃) m/z 222 (M+H)⁺.

EXAMPLE 35B furo[3,2-b]pyridine-2-carbaldehyde

The product from Example 35A (5.6 g, 25 mmol) in THF (50 mL) and water (10 mL) was treated with trifluoroacetic acid (10 mL) and heated at 60° C. for 17 hours. The mixture was allowed to cool to room temperature, treated with water (200 mL), treated with sodium bicarbonate slowly to bring the pH to 8.0, and extracted with dichloromethane (100 mL). The organic phase was dried over anhydrous magnesium sulfate, filtered, and the filtrate concentrated under reduced pressure. The residue was purified by flash chromatography on silica (5% methanol in dichloromethane) to provide the title compound. ¹H NMR (CDCl₃, 400 MHz) δ 7.45 (dd, J=4.75, 8.48 Hz, 1H), 7.77 (s, 1H), 7.93 (dd, J=1.02, 8.48 Hz, 1H), 8.73 (dd, J=1.02, 4.75 Hz, 1H), 9.98 (s, 1H); MS (DCI/NH₃) m/z 148.0 (M+H)⁺.

EXAMPLE 35C

2-{[4-(2-fluorophenyl)-1-piperazinyl]methyl}furo[3,2-b]pyridine 1-(2-Fluorophenyl)piperazine (0.18 g, 1.0 mmol) and sodium triacetoxyborohydride (0.32 g, 1.5 mmol) in dichloroethane (2 mL) were treated with the product from Example 35B (2 mL, 1.0 mmol) as a 0.5M solution in dichloroethane dropwise. The mixture was allowed to stir at room temperature for 17 hours. The mixture was diluted with dichloromethane (10 mL) and washed with 1N NaOH. The organic layer was dried over magnesium sulfate, filtered, and the filtrate concentrated under reduced pressure. The residue was purified by flash chromatography on silica (dichloromethane to 2% methanol in dichloromethane) to provide the title compound. ¹H NMR (CDCl₃, 400 MHz) δ 2.81 (br, 4H), 3.19 (br, 4H), 3.85 (s, 2H), 6.89 (s, 1H), 7.00 (m, 4H), 7.20 (dd, J=4.75, 8.14 Hz, 1H), 7.74 (d, J=8.48 Hz, 1H), 8.52 (d, J=4.75 Hz, 1H); MS (DCI/NH₃) m/z 312.2 (M+H)⁺; Anal. Calcd for C₁₈H₁₈FN₃O: C, 69.44;H, 5.83; N, 13.50. Found: C, 69.36;H, 5.59; N, 13.28.

EXAMPLE 36

2-{[4-(2-methoxyphenyl)-1-piperazinyl]methyl}[1,3]oxazolo[4,5-b]pyridine

EXAMPLE 36A 2-(chloromethyl) [131]oxazolo[4,5-b]pyridine

2-Amino-3-pyridinol (1.1 g, Chemical Abstracts #16867-03-1) and chloromethyltrimethylorthoformate (2.27 g) were combined in diglyme (in 21 mL) and heated at 80° C. for 6 hours. The mixture was treated with p-toluenesulfonic acid hydrate (4 mg) and heated at 80° C. for an additional 48 hours. The mixture was allowed to cool to room temperature and diluted with chloroform (40 mL) and ethanol (10 mL). The mixture was filtered and the filtrate concentrated under reduced pressure. The residue was dissolved in methanol and filtered again. The resulting filtrate was concentrated under reduced pressure to provide the title compound and then dissolved in acetonitrile (3 5 mL) and used as a solution in the next step. $^1$H NMR (CDCl$_3$, 300 MHz) δ 4.82 (2H, s), 7.38 (dd, 1H, J=8.7, 5.4 Hz), 7.89 (dd, 1H, J=8.7, 1.5 Hz), 8.62 (dd, 1H, J=5.4, 1.5 Hz). MS (DCI/NH$_3$) m/z 169 (M+H)$^+$.

EXAMPLE 36B

2-{[4-(2-methoxyphenyl)-1-piperazinyl]methyl}[1,3]oxazolo[4,5-b]pyridine

The solution from Example 36A (7 mL) was treated with 1-(2-methoxyphenyl)piperazine (160 mg) and stirred at 25° C. for 12 hours. The mixture was poured into aqueous sodium chloride solution and extracted with dichloromethane:n-butanol (5:1). The organic phase was concentrated under reduced pressure and the residue was purified by flash chromatography on silica gel (98:2:0.1 dichloromethane:methanol:NH$_4$OH) to provide the title compound. $^1$H NMR (CDCl$_3$, 300 MHz) δ 2.95 (4H, m), 3.21 (4H, m), 3.85 (3H, s), 4.2 (2H, m), 6.88-7.1 (4H, m), 7.40 (1H, m), 7.91 (1H, m), 8.55 (1H, m). MS (DCI/NH$_3$) m/z 325.2 (M+H)$^+$. Anal. Calcd for C$_{18}$H$_{20}$N$_4$O$_2$(0.3H$_2$O): C, 65.56;H, 6.30; N, 16.99. Found: C, 65.61;H, 6.09; N, 16.98.

EXAMPLE 37

2-[4-([1,3]oxazolo[4,5b]pyridin-2-ylmethyl)-1-piperazinyl]benzonitrile

The solution from Example 36A (7 mL) and 2-(1-piperazinyl)benzonitrile (260 mg) were processed as described in Example 36B. $^1$H NMR (CDCl$_3$, 300 MHz) δ 2.95 (4H, m), 3.32 (4H, m), 4.10 (2H, s), 7.08 (2H, m), 7.38 (dd, 1H, J=8.7, 5.4 Hz), 7.55 (2H, m), 7.91 (dd, 1H, J=8.7, 1.5 Hz), 8.55 (dd, 1H, J=5.4, 1.5 Hz); MS (DCI/NH$_3$) m/z 320.2 (M+H)$^+$.

EXAMPLE 38

2-{[4-(2-pyridinyl)-1-piperidinyl]methyl}[1,3]thiazolo[5,4-b]pyridine

EXAMPLE 38A 2-(chloromethyl)[1,3]thiazolo[5,4-b]pyridine

3-Amino-2-pyridinethiol (5.0 g, 39.6 mmol) and 2-chloro-1,1,1-triethoxyethane (8.57 g, 43.5 mmol) were combined in absolute ethanol (40 mL) and refluxed for 2 hours. The mixture was concentrated under reduced pressure and the residue purified by flash chromatography (ethyl acetate:hexanes, 1:4) to provide the title compound. $^1$H NMR (300 MHz, CDCl$_3$) δ 4.93 (s, 2H) 7.47 (dd, J=8.14, 4.75 Hz, 1H) 8.26 (dd, J=8.31, 1.53 Hz, 1H) 8.62 (dd, J=4.58, 1.53 Hz, 1H). (ESI) m/z 186 (M+H)$^+$.

EXAMPLE 38B

2-{[4-(2-pyridinyl)-1-piperidinyl]methyl}[1,3]thiazolo[5,4-b]pyridine

The product from Example 38A (50 mg, 0.11 mmol), 2-(4-piperidinyl)pyridine (25 mg, 0.13 mmol), and D$_1$ EA (340 μL, 2.1 mmol) were combined in acetonitrile (1 mL) and stirred at room temperature for 18 hours. The reaction mixture was concentrated under reduced pressure. The residue was treated with hot methanol. The methanol was filtered and the filter cake washed with cold methanol to provide the title compound. $^1$H NMR (300 MHz, DMSO-d$_6$) δ 2.13 (m, 4H), 3.13 (m, 4H), 3.61 (m, 3H), 7.38 (d, J=4.75 Hz, 1H), 7.76 (dd, J=8.3 Hz, 4.6 Hz, 1H), 7.91 (m, 1H), 8.31 (m, 1H), 8.54 (m, 2H), 8.72 (dd, J=4.6 hz, 1.53 Hz, 1H); (ESI) nil/z 311 (M+H)$^+$.

EXAMPLE 39

2-{[4-(1,3-thiazol-2-yl)-1-piperazinyl]methyl}[1,3]thiazolo[5,4-b]pyridine

The product from Example 38A (200 mg, 1.1 mmol), 1-(1,3-thiazol-2-yl)piperazine (219 mg, 1.3 mmol), and D$_1$ EA (340 μL, 2.1 mmol) were processed as described in Example 38B to provide the title compound. $^1$H NMR (300 MHz, DMSO-d$_6$) δ 2.71 (m, 4H) 3.46 (m, 4H) 4.06 (s, 2H) 6.86 (d, J=3.73 Hz, 1H) 7.17 (d, J=−3.73 Hz, 1H) 7.56 (dd, J=8.14, 4.75 Hz, 1H) 8.33 (dd, J=8.14, 1.70 Hz, 1H) 8.59 (dd, J=4.58, 1.53 Hz, 1H). (ESI) m/z 318 (M+H)$^+$.

EXAMPLE 40

4-{4-[(5-methoxy[1,3]thiazolo[5,4-b]pyridin-2-yl)methyl]-1-piperazinyl}phenol

EXAMPLE 40A 2-(chloromethyl)-5-methoxy[1,3]thiazolo[5,4-b]pyridine

3-Amino-6-methoxy-2-pyridinethiol (0.8 g, Maybridge Co.) and 2-chloro-1,1,1-triethoxyethane (1.26 g) were combined in ethanol (5 mL) and heated at 90° C. in a sealed tube for 2 hours. The mixture was allowed to cool to room temperature and filtered. The filtrate was concentrated under reduced pressure and the residue was purified by flash chromatography (2:1, dichloromethane:hexanes) to provide th-e title compound. $^1$H NMR (CDCl$_3$, 300 MHz) δ 4.00 (3H, s), 4.88 (2H, s), 6.88 (1H, d, J=8.7 Hz), 8.10 (1H, d, J=8.7 Hz); MS (DCI/NH$_3$) nil/z 215.0 (M+H)$^+$.

EXAMPLE 40B

4-{4-[(5-methoxy[1,3]thiazolo[5,4-b]pyridin-2-yl)methyl]-1-piperazinyl}phenol

The product from Example 40A (0.184 mmol) and 4-(1-piperazinyl)phenol (3 equivalents) were combined in acetonitrile (1 mL) and stirred at 25° C. for 24 hours. The mixture was evaporated to dryness and the residue was recrystallized from dimethylsulfoxide/methanol to provide the title compound. $^1$H NMR (CD$_3$OD/CDCl$_3$, 300 MHz) δ 2.80 (4H, t, J=5.7 Hz), 3.12 (4H, t, J=5.7 Hz), 3.98 (2H, s), 4.02 (3H, s), 6.78 (2H, d, J=8.7 Hz), 6.81 (1H, d, J=8.7 Hz), 6.85 (2H, d, J=8.7 Hz), 8.04 (1H, d, J=8.7 Hz); MS (DCI/NH$_3$) m/z 357 (M+H)$^+$.

EXAMPLE 41

2-{[4-(2-fluorophenyl)-1-piperazinyl]methyl}-5-methoxy[1,3]thiazolo[5,4-b]pyridine The product from Example 40A (0.184 mmol) and 1-(2-fluorophenyl)piperazine (3 equivalents) were processed as described in Example 40B to provide the title compound. $^1$H NMR (CD$_3$OD/CDCl$_3$, 300 MHz) δ 2.83 (4H, m), 3.08 (4H, m), 3.98 (2H, s), 4.01 (3H, s), 6.85 (1H, d, J=8.7 Hz), 6.95-7.09 (5H, m), 8.08 (1H, d, J=8.7 Hz). MS (DCI/NH$_3$) m/z 359 (M+H)$^+$.

EXAMPLE 42

5-methoxy-2-({4-[2-(methylthio)phenyl]-1-piperazinyl}methyl)[1,3]triazolo[5,4-b]pyridine The product from Example 40A (0.184 mmol) and 1-[2-(methylthio)phenyl]piperazine (3 equivalents) were processed as described in Example 40B to provide the title compound. $^1$H NMR (CD$_3$OD/CDCl$_3$, 300 MHz) δ 2.41 (s, 3H), 2.85 (4H, m), 3.10 (4H, m), 4.00 (2H, s), 4.05 (3H, s), 6.85 (1H, d, J=8.7 Hz), 7.15 (4H, m), 8.10 (1H, d, J=8.7 Hz); MS (DCI/NH$_3$) m/z 387 (M+H)$^+$.

EXAMPLE 43

5-methoxy-2-{[4-(6-methyl-2-pyridinyl)-1-piperazinyl]methyl}[1,3]thiazolo[5,4-b]pyridine The product from Example 40A (0.184 mmol) and 1-(6-methyl-2-pyridinyl)piperazine (3 equivalents) were processed as described in Example 40B to provide the title compound. $^1$H NMR (CD$_3$OD/CDCl$_3$, 300 MHz) δ 2.55 (3H, s), 2.78 (4H, m), 3.60 (4H, m), 3.98 (2H, s), 4.05 (3H, s), 6.48 (1H, d, J=8.7 Hz), 6.55 (1H, d, J=8.7 Hz), 6.82 (1H, d, J=8.7 Hz), 7.40 (1H, m), 8.08 (1H, d, J=8.7 Hz); MS (DCI/NH$_3$) m/z 356 (M+H)$^+$.

EXAMPLE 44

5-methoxy-2-{[4-(2-pyridinyl)-1-piperazinyl]methyl}[1,3]thiazolo[5,4-b]pyridine

The product from Example 40A (0.184 mmol) and 1-(2-pyridinyl)piperazine (3 equivalents) were processed as described in Example 40B to provide the title compound. $^1$H NMR (CD$_3$OD/CDCl$_3$, 300 MHz) δ 2.77 (4H, t, J=5.7 Hz), 3.60 (4H, t, J=5.7 Hz), 3.96 (2H, s), 4.01 (3H, s), 6.65 (2H, m), 6.82 (1H, d, J=8.7 Hz), 7.50 (1H, m), 8.04 (1H, d, J=8.7 Hz), 8.18 (1H, m); MS (DCI/NH$_3$) m/z 342 (M+H)$^+$.

EXAMPLE 45

5-methoxy-2-{[4-(2-pyrimidinyl)-1-piperazinyl]methyl}[1,3]thiazolo[5,4-b]pyridine The product from Example 40A (0.184 mmol) and 2-(1-piperazinyl)pyrimidine (3 equivalents) were processed as described in Example 40B to provide the title compound. $^1$H NMR (CD$_3$OD/CDCl$_3$, 300 MHz) δ 2.72 (4H, t, J=5.7 Hz), 3.85 (4H, t, J=5.7 Hz), 3.94 (2H, s), 4.01 (3H, s), 6.50 (1H, t, J=5.4 Hz), 6.84 (1H, d, J=8.7 Hz), 8.04 (1H, d, J=8.7 Hz), 8.30 (2H, d); MS (DCI/NH$_3$) m/z 343 (M+H)$^+$.

EXAMPLE 46

5-methoxy-2-{[4-(2-methoxyphenyl)-1-piperazinyl]methyl}[1,3]thiazolo[5,4-b]pyridine The product from Example 40A (0.184 mmol) and 1-(2-methoxyphenyl)piperazine (3 equivalents) were processed as described in Example 40B to provide the title compound. $^1$H NMR (CD$_3$OD/CDCl$_3$, 300 MHz) δ 2.84 (4H, m), 3.14 (4H, m), 3.88 (3H, s), 3.98 (2H, s), 4.00 (3H, s), 6.84 (1H, d, J=8.7 Hz), 6.90-7.1 (4H, m), 8.06 (1H, d, J=8.7 Hz); MS (DCI/NH$_3$) m/z 371 (M+H)$^+$.

EXAMPLE 47

2-{[4-(2-chlorophenyl)-1-piperazinyl]methyl}-5-methoxy[1,3]thiazolo[5,4-b]pyridine The product from Example 40A (0.184 mmol) and 1-(2-chlorophenyl)piperazine (3 equivalents) were processed as described in Example 40B to provide the title compound. $^1$H NMR (CD$_3$OD/CDCl$_3$, 300 MHz) δ 2.83 (4H, m), 3.18 (4H, m), 3.99 (2H, s), 4.01 (3H, s), 6.83 (1H, d, J=8.7 Hz), 6.99 (1H, m), 7.08 (1H, dd, J=7.5, 1.5 Hz), 7.22 (1H, m), 7.36 (1H, d, J=7.5, 1.5 Hz), 8.03 (1H, d, J=8.7 Hz); MS (DCI/NH$_3$) m/z 375 (M+H)$^+$.

EXAMPLE 48

2-{4-[(5-methoxy[1,3]thiazolo[5,4-b]pyridin-2-yl)methyl]-1-piperazinyl}benzonitrile The product from Example 40A (0.184 mmol) and 2-(1-piperazinyl)benzonitrile (3 equivalents) were processed as described in Example 40B to provide the title compound. $^1$H NMR (CD$_3$OD/CDCl$_3$, 300 MHz) δ 2.90 (4H, m), 3.30 (4H, m), 4.01 (5H, s), 6.85 (1H, d, J=8.7 Hz), 7.04 (2H, m), 7.50 (1H, m), 7.68 (1H, m), 8.08 (1H, d, J=8.7 Hz); MS (DCI/NH$_3$) m/z 366 (M+H)$^+$.

EXAMPLE 49

5-methoxy-2-[(4-phenyl-1-piperazinyl)methyl][1,3]thiazolo[5,4-b]pyridine

The product from Example 40A (0.184 mmol) and 1-phenylpiperazine (3 equivalents) were processed as described in Example 40B to provide the title compound. $^1$H NMR (CD$_3$OD/CDCl$_3$, 300 MHz) δ 2.82 (4H, m), 3.25 (4H, m), 3.86 (2H, s), 4.02 (3H, s), 6.85 (1H, d, J=8.7 Hz), 6.95 (4H, m), 7.25 (1H, m), 8.03 (1H, d, J=8.7 Hz); MS (DCI/NH$_3$) m/z 341 (M+H)$^+$.

EXAMPLE 50

2-{[4-(2-chlorophenyl)-1-piperazinyl]methyl}[1,3]thiazolo[5,4-b]pyridine

The product from Example 38A (60 mg, 0.3 mmol), 1-(2-chlorophenyl)piperazine (70 mg, 0.31 mmol), and D$_1$ EA (110 μL, 0.66 mmol) were processed as described in Example 38B to provide the title compound. $^1$H NMR (500 MHz, DMSO-d$_6$) δ 2.77 (m, 4H) 3.12 (m, 4H) 4.06 (s, 2H) 7.03 (m, 1H) 7.19 (m, 1H) 7.29 (m, 1H) 7.39 (dd, J=7.96, 1.40 Hz, 1H) 7.54 (dd, J=8.11, 4.68 Hz, 1H) 8.31 (dd, J=8.11, 1.56 Hz, 1H) 8.58 (dd, J=4.68, 1.56 Hz, 1H) (ESI) m/z 345 (M+H)$^+$.

EXAMPLE 51

2-{[4-(6-methyl-2-pyridinyl)-1-piperazinyl]methyl}[1,3]thiazolo[5,4-b]pyridine

The product from Example 38A (50 mg, 0.81 mmol), 1-(6-methyl-2-pyridinyl)piperazine (160 mg, 0.98 mmol), and D$_1$ EA (280 μL, 1.6 mmol) were processed as described in Example 38B to provide the title compound. $^1$H NMR $^1$H NMR (300 MHz, DMSO-d$_6$) δ 2.68 (m, 4H) 3.32 (s, 3H) 3.53 (m, 4H) 4.04 (s, 2H) 6.54 (m, 1H) 6.61 (d, J=8.48 Hz, 1H) 7.40 (m, 1H) 7.56 (dd, J=8.31, 4.58 Hz, 1H) 8.33 (dd, J=8.31, 1.53 Hz, 1H); (ESI) m/z 326 (M+H)$^+$.

EXAMPLE 52

2-{[4-(5-chloro-2-methoxyphenyl)-1-piperazinyl]methyl}[1,3]thiazolo[5,4-b]pyridine The product from Example 8A (150 mg, 0.81 mmol), 1-(5-chloro-2-methoxyphenyl)piperazine (160 mg, 0.98 mmol), and D$_1$ EA (280 µL, 1.6 mmol) were processed as described in Example 38B to provide the title compound. $^1$H NMR (300 MHz, DMSO-d$_6$) δ 2.74 (m, 4H) 3.05 (m, 4H) 3.77 (s, 3H) 4.05 (s, 2H) 6.93 (m, 2H) 7.56 (dd, J=8.31, 4.58 Hz, 2H) 8.33 (dd, J=8.14, 1.70 Hz, 1H) 8.59 (dd, J=4.58, 1.53 Hz, 1H); (ESI) m/z 375 (M+H)$^+$.

EXAMPLE 53

4-[4-([1,3]thiazolo[5,4-b]pyridin-2-ylmethyl)-1-piperazinyl]phenol

The product from Example 38A (150 mg, 0.81 mmol), 4-(1-piperazinyl)phenol (160 mg, 0.98 mmol), and D$_1$ EA (280 µL, 1.6 mmol) were processed as described in Example 38B to provide the title compound. $^1$H NMR (300 MHz, DMSO-d$_6$) δ 2.73 (m, 4H) 3.02 (m, 4H) 4.03 (s, 2H) 6.72 (m, 4H) 7.56 (dd, J=8.14, 4.75 Hz, 1H) 8.33 (dd, J=8.14, 1.70 Hz, 1H) 8.59 (dd, J=4.58, 1.53 Hz, 1H): (ESI) m/z 327 (M+H)$^+$.

EXAMPLE 54

2-[4-([1,3]thiazolo[5,4-b]pyridin-2-ylmethyl)-1-piperazinyl]nicotinonitrile

The product from Example 38A (150 mg, 0.81 mmol), 2-(1-piperazinyl)nicotinonitrile (160 mg, 0.98 mmol), and D$_1$ EA (280 µL, 1.6 mmol) were processed as described in Example 38B to provide the title compound. $^1$H NMR (300 MHz, DMSO-d$_6$) δ 2.75 (m, 4H) 3.68 (m, 4H) 4.07 (s, 2H) 6.94 (m, 1H) 7.56 (m, 1H) 8.08 (dd, J=7.80, 2.03 Hz, 1H) 8.33 (dd, J=8.31, 1.53 Hz, 1H) 8.42 (dd, J=4.75, 1.70 Hz, 1H) 8.60 (dd, J=4.58, 1.53 Hz, 1H); (ESI) m/z 337 (M+H)$^+$.

EXAMPLE 55

2-({4-[2-(methylthio)phenyl]-1-piperazinyl}methyl)[1,3]thiazolo[5,4-b]pyridine

The product from Example 38A (150 mg, 0.81 mmol), 1-[2-(methylthio)phenyl]piperazine (160 mg, 0.98 mmol), and D$_1$ EA (280 µL, 1.6 mmol) were processed as described in Example 38B to provide the title compound. $^1$H NMR (300 MHz, DMSO-d$_6$) δ 2.37 (s, 3H) 2.75 (m, 4H) 2.97 (m, 4H) 4.06 (s, 2H) 7.13 (m, 3H) 7.56 (dd, J=8.31, 4.58 Hz, 2H) 8.33 (dd, J=8.14, 1.36 Hz, 1H) 8.59 (dd, J=4.58, 1.53 Hz, 1H); (ESI) m/z 357 (M+H)$^+$.

EXAMPLE 56

2-{[4-(2-pyrimidinyl)-1-piperazinyl]methyl}[1,3]thiazolo[5,4-b]pyridine

The product from Example 38A (150 mg, 0.81 mmol), 2-(1-piperazinyl)pyrimidine (160 mg, 0.98 mmol), and D$_1$ EA (280 µL, 1.6 mmol were processed as described in Example 38B to provide the title compound. $^1$H NMR (300 MHz, DMSO-d$_6$) δ 2.65 (m, 4H) 3.80 (m, 4H) 4.04 (s, 2H) 6.63 (t, J=4.92 Hz, 1H) 7.56 (dd, J=8.14, 4.75 Hz, 1H) 8.34 (m, 2H) 8.43 (d, J=4.75 Hz, 1H) 8.59 (dd, J=4.75, 1.70 Hz, 1H); (ESI) m/z 313 (M+H)$^+$.

EXAMPLE 57

2-{[4-(2-pyridinyl)-1-piperazinyl]methyl}[1,3]thiazolo[5,4-b]pyridine

The product from Example 38A (150 mg, 0.81 mmol), 1-(2-pyridinyl)piperazine (160 mg, 0.98 mmol), and D$_1$ EA (280 µL, 1.6 mmol) were processed as described in Example 38B to provide the title compound. $^1$H NMR (300 MHz, DMSO-d$_6$) δ 2.80 (m, 4H) 3.55 (m, 4H) 4.04 (s, 2H) 6.63 (m, 1H) 6.81 (m, 1H) 7.53 (m, 2H) 8.11 (m, 1H) 8.33 (dd, J=8.14, 1.70 Hz, 1H) 8.59 (dd, J=4.58, 1.53 Hz, 1H); (ESI) m/z 312 (M+H)$^+$.

EXAMPLE 58

2-{[4-(2-fluorophenyl)-1-piperazinyl]methyl}[1,3]thiazolo[5,4-b]pyridine

The product from Example 38A (200 mg, 1.1 mmol), 1-(2-fluorophenyl)piperazine (215 mg, 1.2 mmol), and D$_1$ EA (380 µL, 2.2 mmol) were processed as described in Example 38B to provide the title compound. $^1$H NMR (300 MHz, DMSO-d$_6$) δ 2.77 (m, 4H) 3.10 (m, 4H) 4.06 (s, 2H) 7.08 (m, 4H) 7.56 (dd, J=8.14, 4.75 Hz, 1H) 8.33 (dd, J=8.31, 1.53 Hz, 1H) 8.59 (dd, J=4.58, 1.53 Hz, 1H); (ESI) m/z 329 (M+H)$^+$.

EXAMPLE 59

2-[4-([1,3]thiazolo[5,4-b]pyridin-2-ylmethyl)-1-piperazinyl]benzonitrile

The product from Example 38A (680 mg, 3.7 mmol), 2-(1-piperazinyl)benzonitrile (823 mg, 4.4 mmol), and D$_1$ EA (1.3 mL, 7.4 mmol) were processed as described in Example 38B to provide the title compound. $^1$H NMR (300 MHz, DMSO-d$_6$) δ 2.80 (m, 4H) 3.23 (m, 4H) 4.09 (s, 2H) 7.13 (m, 1H) 7.21 (d, J=8.14 Hz, 1H) 7.59 (m, 2H) 7.71 (dd, J=7.80, 1.70 Hz, 1H) 8.34 (dd, J=8.14, 1.70 Hz, 1H) 8.59 (dd, J=4.75, 1.70 Hz, 1H); (ESI) m/z 336 (M+H)$^+$.

EXAMPLE 60

2-{[4-(2-methoxyphenyl)-1-piperazinyl]methyl}[1,3]thiazolo[5,4-b]pyridine

The product from Example 38A (200 mg, 1.1 mmol), 1-(2-methoxyphenyl)piperazine (229 mg, 1.2 mmol), and D$_1$ EA (380 µL, 2.2 mmol) were processed as described in Example 38B to provide the title compound. $^1$H NMR (300 MHz, DMSO-d$_6$) δ 2.74 (m, 4H) 3.02 (m, 4H) 3.78 (s, 3H) 4.04 (s, 2H) 6.91 (m, 3H) 7.56 (dd, J=8.31, 4.75 Hz, 2H) 8.33 (dd, J=8.14, 1.70 Hz, 1H) 8.59 (dd, J=4.75, 1.70 Hz, 1H); (ESI) m/z 341 (M+H)$^+$.

EXAMPLE 61

2-[(4-phenyl-1-piperazinyl)methyl][1,3]thiazolo[5,4-b]pyridine

The product from Example 38A (200 mg, 1.1 mmol), 1-phenylpiperazine (193 mg, 1.2 mmol), and D$_1$ EA (380 µL, 2.2 mmol) were processed as described in Example 38B to provide the title compound.

¹H NMR (300 MHz, DMSO-d₆) δ 2.74 (m, 4H) 3.19 (m, 4H) 4.05 (s, 2H) 6.78 (t, J=7.29 Hz, 1H) 6.95 (d, J=7.80 Hz, 2H) 7.22 (m, 2H) 7.56 (dd, J=8.15, 4.75 Hz, 1H) 8.33 (dd, J=8.15, 1.70 Hz, 1H) 8.59 (dd, J=4.75, 1.70 Hz, 1H); (ESI) m/z 311 (M+H)⁺.

EXAMPLE 62

2-{[4-(2-fluorophenyl)-1-piperazinyl]methyl}-1H-thieno[3,4-d]imidazole

EXAMPLE 62A 2-(chloromethyl)-1H-thieno[3,4-d]imidazole 3,4-Thiophenediamine (0.5 g, Toronto Research Chemicals, Chemical Abstracts # 90069-81-1) and 2-chloro-1,1,1-triethoxyethane (0.9 g) were combined in dimethoxyethane (7 mL) in a sealed tube and heated at 95° C. for one hour. After allowing to cool to room temperature and stirring for 24 hours, the mixture was treated with hexane (10 mL) and filtered. The filter cake was dried under reduced pressure to provide the title compound. MS (DCI/NH₃) m/z 173 (M+H)⁺.

EXAMPLE 62B

2-{[4-(2-fluorophenyl)-1-piperazinyl]methyl}-1H-thieno[3,4-d]imidazole

The product from Example 62A (0.23 mmole) and 1-(2-fluorophenyl)piperazine (1 mmole) were combined in dimethylsulfoxide (1 mL) and stirred at 25° C. for 24 hours. The mixture was partitioned between CH₂Cl₂ (4 mL), butanol (0.1 mL), and diluted aqueous ammonia (15 mL). The organic phase was separated and concentrated under reduced pressure. The residue was purified by flash chromatography on silica gel (19:1:0.1 CH₂Cl₂:methanol:ammonium hydroxide) to provide the title compound. ¹H NMR (CD₃OD, 300 MHz) δ 2.8 (4H, m), 3.18 (4H, m), 3.86 (2H, s), 6.9-7.1 (m, 6H); MS (DCI/NH₃) m/z 317 (M+H)⁺.

EXAMPLE 63

2-{[4-(2-methoxyphenyl)-1-piperazinyl]methyl}-1H-thieno[3,4-d]imidazole

The product from Example 62A (0.23 mmol) and 1-(2-methoxyphenyl)piperazine (1 mmole) were processed as described in Example 62B. ¹H NMR (CD₃OD, 300 MHz) δ 1.65 (m, 4H), 2.62 (2H, s), 2.90 (4H, m), 3.85 (3H, s), 6.9 (m, 5H), 7.05 (m, 1H); MS (DCI/NH₃) m/z 329 (M+H)⁺.

EXAMPLE 64

2-{[4-(2-pyrimidinyl)-1-piperazinyl]methyl}-1H-thieno[3,4-d]imidazole

The product from Example 62A (0.23 mmol) and 2-(1-piperazinyl)pyrimidine (1 mmol) were processed as described in Example 62B. ¹H NMR (CD₃OD, 300 MHz) δ 2.75 (4H, m), 3.80 (2H, s), 3.90 (4H, m), 6.52 (t, 1H, J=5.4 Hz), 6.80 (m, 2H), 8.31 (d, 2H, J=5.4 Hz). MS (DCI/NH₃) m/z 301 (M+H)⁺.

EXAMPLE 65

2-{[4-(2-pyridinyl)-1-piperazinyl]methyl}-1H-thieno[3,4-d]imidazole

The product from Example 62A (0.23 mmol) and 1-(2-pyridinyl)piperazine (1 mmol) were processed as described in Example 62B. ¹H NMR (CD₃OD, 300 MHz) δ 2.63 (4H, t, J=5.7 Hz), 3.58 (4H, t, J=5.7 Hz), 3.75 (2H, s), 6.65 (dd, 1H, J=7.5, 5.4 Hz), 6.82 (d, 1H, J=8.7 Hz), 6.85 (m, 2H), 7.57 (1H, m), 8.08 (m, 1H); MS (DCI/NH₃) m/z 300 (M+H)⁺.

EXAMPLE 66

2-[4-(1H-thieno[3,4-d]imidazol-2-ylmethyl)-1-piperazinyl]nicotinonitrile

The product from Example 62A (0.23 mmol) and 2-(1-piperazinyl)nicotinonitrile (1 mmol) were processed as described in Example 62B. ¹H NMR (CD₃OD, 300 MHz) δ 2.79 (4H, m), 3.82 (6H, m), 6.90 (m, 2H), 8.34 (dd, 1H, J=7.8, 4.8 Hz), 7.80 (dd, 1H, J=7.8, 1.5 Hz), 8.34 (dd, 1H, J=4.8, 1.5 Hz); MS (DCI/NH₃) m/z 325 (M+H)⁺.

EXAMPLE 67

4-[4-(1H-thieno[3,4-d]imidazol-2-ylmethyl)-1-piperazinyl]phenol

The product from Example 62A (0.23 mmol) and 4-(1-piperazinyl)phenol (1 mmol) were processed as described in Example 62B. ¹H NMR (CD₃OD, 300 MHz) δ 2.78 (4H, t, J=5.4 Hz), 3.11 (4H, t, J=5.4 Hz), 3.79 (2H, s), 6.76 (2H, J=8.7 Hz), 6.90 (m, 4H), 7.8 (s, 1H); MS (DCI/NH₃) m/z 315 (M+H)⁺.

EXAMPLE 68

2-({4-[2-(methylthio)phenyl]-1-piperazinyl}methyl)-1H-thieno[3,4-d]imidazole

The product from Example 62A (0.23 mmol) and 1-[2-(methylthio)phenyl]piperazine (1 mmol) were processed as described in Example 62B. ¹H NMR (CD₃OD, 300 MHz) δ 1.65 (m, 4H), 2.40 (3H, s), 3.0 (6H, m), 7.1 (6H, m); MS (DCI/NH₃) m/z 345 (M+H)⁺.

Synthesis of D4 agonists (from Mcowart 051903)

EXAMPLE 69-84

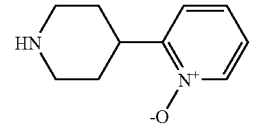

1', 2', 3', 4', 5', 6'-Hexahydro-[2, 4']bipyridinyl 1-oxide

The synthesis of the chemical intermediate 1',2',3',4',5',6'-hexahydro-[2,4']bipyridinyl 1-oxide has been described in Cui, Donghui; Davis, Margaret R.; Dunn, Michael; Evans, Ben E.; Kari, Hanumath P.; Lagu, Bharat; Nagarathnam, Dhanapalan; Vyas, Kamlesh P.; Zhang, Kanyin. Preparation of difluorophenyldihydro-pyrimidinecarboxamides as α1a receptor antagonists. U.S. (2001), 27 pp. U.S. Pat. No. 6,274,585 B1. It can also be prepared by the following route:

To a solution of diisopropylamine (13.4 mL. 96 mmol) in THF (350 mL) at −78° C. was added 1.6M nBuLi in hexane (60 mL, 96 mmol). The reaction mixture was stirred for 5 min at −78° C. A solution of t-butoxycarbonyl-4-piperidone (16 g, 80 mmol) in THF (100 mL) was added and the reaction mixture was stirred for 10 min. Then a solution of N-phenyl-trifluoromethanesulfonimide (31.4 g, 88 mmol) was added.

The reaction mixture was stirred at −78° C. for 30 min and the cooling bath was removed to warm it up to room temperature (~1.5 hr). The reaction was quenched by saturated NaHCO₃ followed by extraction with ethyl ether and 5% citric acid. The organic layer was then washed with 1NaOH (4×200 mL), and water (2×200 mL), and by saturated aqueous NaCl (1×200 mL), dried over MgSO₄, and evaporated on rotary evaporator to give yellowish oil. Purification by flash chromatography using Hexane: Ethyl acetate 8:2 as eluent gave 18g of 4-Trifluoromethanesulfonyloxy-3,6-dihydro-2H-pyridine-1-carboxylic acid tert-butyl ester as a pure colorless oil. ¹H NMR (300 MHz, DMSO-d₆) δ 1.41 (s, 9H), 2.41 (m, 2H), 3.54 (t, 2H), 3.98 (m, 2H), 6.02 (m, 1H).

Next, a pure solution of 4-trifluoromethanesulfonyloxy-3,6-dihydro-2H-pyridine-1-carboxylic acid tert-butyl ester (18g, 54 mmol) in THF (200 mL) was treated with 2-pyridylzinc bromide 0.5 molar solution in THF (from Aldrich, brown color) (124 mL, 62.5 mmol, 1.15 eq.) followed by Pd(PPh₃)₄ (from Strem Chemicals) (625 mg). The reaction mixture was heated at 60° C. for 90 minutes. The THF was removed by rotary evaporator. Ethyl acetate (300 mL) and 1 N NaOH (200 mL) were added to the residue, and the zinc salts were removed by filtration. The organic layer was separated and washed with brine (300 mL), dried (MgSO₄), and concentrated on the rotary evaporator to give brown oil. Purification by flash chromatography using Hexane: Ethyl acetate 6:4 as eluent gave 9.0 g (64% yield) of 3',6'-dihydro-2'H-[2,4']bipyridinyl-1'-carboxylic acid tert-butyl ester as colorless oil. ¹H NMR (300 MHz, DMSO-d₆) δ 1.43 (s, 9H), 2.56 (m, 2H), 3.54 (t, 2H), 4.04 (m, 2H), 6.08 (m, 1H), 7.25 (dd, 1H), 7.56 (d, J=9 Hz, 1H), 7.77 (m, 1H), 8.54 (m, 1H); MS (DCI—NH₃) m/z 259 (M+H)⁺, 277 (M+H+18)⁺

Next, 3',6'-Dihydro-2'H-[2,4']bipyridinyl-1'-carboxylic acid tert-butyl ester (9.0 g) was hydrogenated using 10% Pd/C dry (900 mg) at 60 psi at room temperature for 1.5 hr to give 8.9 g (99%) of 3',4',5',6'-tetrahydro-2'H-[2,4']bipyridinyl-1'-carboxylic acid tert-butyl ester as a colorless oil. ¹H NMR (300 MHz, DMSO-d₆) δ 1.41 (s, 9H), 1.58 (m, 2H), 1.81 (m, 2H), 2.85 (m, 3H), 4.06 (m, 2H), 7.20 (dd, 1H), 7.28 (d, J=9 Hz, 1H), 7.70 (m, 1H), 8.48 (m, 1H).

Next, 3',4',5',6'-tetrahydro-2'H-[2,4']bipyridinyl-1'-carboxylic acid tert-butyl ester (8.9 g, 33.9 mmol) in dichloromethane (30 mL) was cooled to 0° C. and treated with m-chloroperbenzoic acid 77% (10.5 g, 61.06 mmol, 1.8 eq.). The reaction mixture was stirred at 0° C. for 30 minutes then at room temperature for 2 hours, CH₂Cl₂ (50 mL) was added to the reaction mixture and washed with saturated NaHCO₃ then with brine, dried over MgSO₄, concentrated in vacuo. The residue was triturated with 5% CH₂Cl₂ in hexane to give 1-oxy-3',4',5',6'-tetrahydro-2'H-[2,4']bipyridinyl-1'-carboxylic acid tert-butyl ester as a white solid, ¹H NMR (300 MHz, DMSO-d₆) δ 1.41 (s, 9H), 1.42 (m, 2H), 1.90 (m, 2H), 2.83 (m, 2H), 3.45 (m, 1H), 4.09 (m, 2H), 7.30 (m, 2H), 7.40 (m, 1H), 8.26 (m, 1H).

Next, 3',4',5',6'-tetrahydro-2'H-[2,4']bipyridinyl-1'-carboxylic acid tert-butyl ester (6.57 g) was dissolved in ethyl acetate (150 mL) and cooled to −78° C. HCl gas was bubbled through the reaction mixture for 15 min. The reaction mixture was allowed to warn up to room temperature upon which a precipitate was formed. The precipitate was filtered and washed with ethyl acetate, dried under high vacuum to give the HCl salt of the desired product 1',2',3',4',5',6'-hexahydro-[2,4']bipyridinyl 1-oxide (5.04 g, 99% yield). ¹H NMR (300 MHz, DMSO-d₆) δ 1.82 (m, 2H), 2.10 (m, 2H), 3.06 (m, 2H), 3.36 (m, 2H), 3.58 (m, 1H), 7.45 (m, 3H), 8.39 (d, J=9 Hz, 1H), 9.04 (bs, 1H); MS (DCI—NH₃) m/z 179 (M+H)⁺, 163 (M+H-16)⁺.

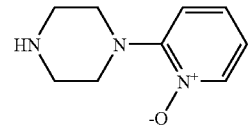

1-(-Oxy-pyridin-2-yl)-piperazine

The preparation of the chemical intermediate 1-(1-oxy-pyridin-2-yl)-piperazine has been described in Regnier, et al. Arzneim. Forsch. (1974) 24, p 1964-1970; and as it's hydrochloride salt in Taveras, Arthur G.; Aki, Cynthia J.; Bond, Richard W.; Chao, Jianping; Dwyer, Michael; Ferreira, Johan A.; Chao, Jianhua; Yu, Younong; Baldwin, John J.; Kaiser, Bernd; Li, Ge; Merritt, J. Robert; Nelson, Kingsley H.; Rokosz, Laura L. Preparation of 3,4-di-substituted cyclobutene-1,2-diones as cxc-chemokine receptor ligands. PCT Int. Appl. (2002), 394 pp. WO 0283624 A1.

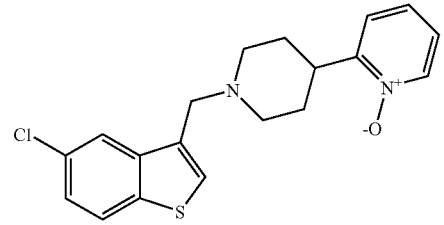

By the method used to prepare 1-[(5-chloro-1-benzothien-3-yl)methyl]-4-(6-methyl-2-pyridinyl)piperazine, 3-(Bromomethyl)-5-chloro-1-benzothiophene may be reacted with 1',2',3',4',5',6'-hexahydro-[2,4']bipyridinyl 1-oxide to prepare 1'-(5-Chloro-benzo[b]thiophen-3-ylmethyl)-1',2',3',4',5',6'-hexahydro-[2,4']bipyridinyl 1-oxide.

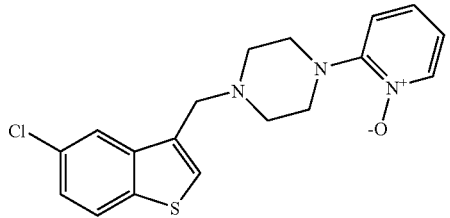

By the method used to prepare 1-[(5-chloro-1-benzothien-3-yl)methyl]-4-(6-methyl-2-pyridinyl)piperazine, 3-(Bromomethyl)-5-chloro-1-benzothiophene may be reacted with 1-(1-oxy-pyridin-2-yl)-piperazine to prepare 1-(5-Chloro-benzo[b]thiophen-3-ylmethyl)-4-(1-oxy-pyridin-2-yl)-piperazine.

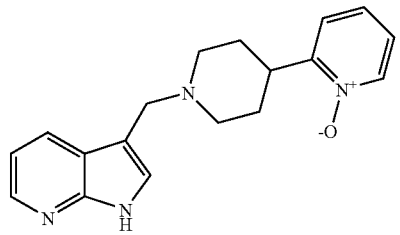

1'-(1-H-Pyrrolo[2, 3-b]pyridin-3-ylmethyl)-1', 2', 3', 4', 5', 6'-hexahydro-[2, 4']bipyridinyl 1-oxide By the method used to prepare 2-[4-(1H-pyrrolo[2,3-b]pyridin-2-ylmethyl)-1-piperazinyl]benzonitrile, 1H-pyrrolo

[2,3-b]pyridine may be reacted with formaldehyde and 1',2',3',4',5',6'-hexahydro-[2,4']bipyridinyl 1-oxide to prepare 1'-(1H-Pyrrolo[2,3-b]pyridin-3-ylmethyl)-1',2',3',4',5',6'-hexahydro-[2,4']bipyridinyl 1-oxide.

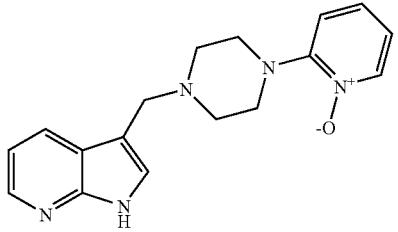

By the method used to prepare 2-[4-(1H-pyrrolo[2,3-b]pyridin-2-ylmethyl)-1-piperazinyl]benzonitrile, 1H-pyrrolo[2,3-b]pyridine may be reacted with formaldehyde and 1-(1-oxy-pyridin-2-yl)-piperazine to prepare 3-[4-(1-Oxy-pyridin-2-yl)-piperazin-1-ylmethyl]-1H-pyrrolo[2,3-b]pyridine.

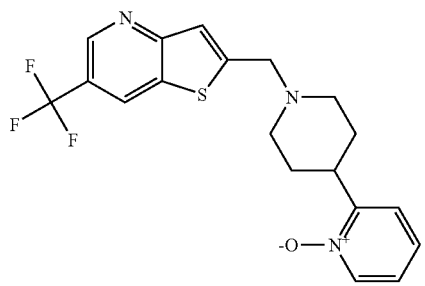

1'-(6-Trifluoromethyl-thieno[3,2-b]pyridin-2-ymethyl)-1',2',3',4',5',6'-hexahydro-[2,4']bipyridinyl 1-oxide By the method used to prepare 4-(4-{[6-(trifluoromethyl)thieno[3,2-b]pyridin-2-yl]methyl}-1-piperazinyl)phenol, [6-(trifluoromethyl)thieno[3,2-b]pyridin-2-yl]methyl methanesulfonate may be reacted with 1',2',3',4',5',6'-hexahydro-[2,4']bipyridinyl 1-oxide to prepare 1'-(6-Trifluoromethyl-thieno[3,2-b]pyridin-2-ylmethyl)-1',2',3',4',5',6'-hexahydro-[2,4']bipyridinyl 1-oxide.

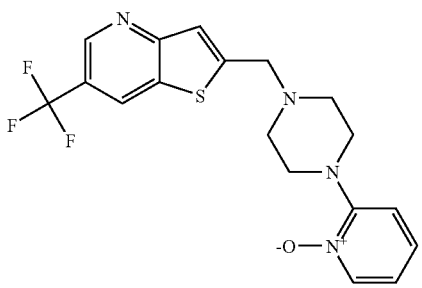

2-[4-(1-Oxy-pyridin-2-yl)-piperazin-1-ymethyl]-6-trifluoromethyl-thieno[3,2-b]pyridine By the method used to prepare 4-(4-{[6-(trifluoromethyl)thieno[3,2-b]pyridin-2-yl]methyl}-1-piperazinyl)phenol, [6-(trifluoromethyl)thieno[3,2-b]pyridin-2-yl]methyl methanesulfonate may be reacted with 2-[4-(1-Oxy-pyridin-2-yl)-piperazin-1-ylmethyl]-6-trifluoromethyl-thieno[3,2-b]pyridine.

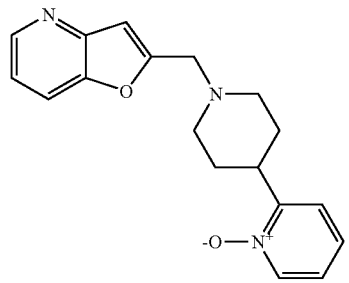

1'-Furo[3,2-b]pyridin-2-ymethyl-1',2',3',4',5',6'-hexahydro-[2,4']bipyridinyl 1-oxide By the method used to prepare 2-[(4-phenyl-1-piperazinyl)methyl]furo[3,2-b]pyridine, furo[3,2-b]pyridine-2-carbaldehyde may be reacted with 1',2',3',4',5',6'-hexahydro-[2,4']bipyridinyl 1-oxide to prepare 1'-Furo[3,2-b]pyridin-2-ylmethyl-1',2',3',4',5',6'-hexahydro-[2,4']bipyridinyl 1-oxide.

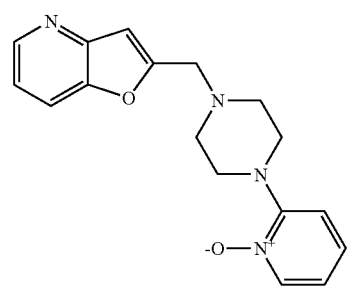

2-[4-(1-Oxy-pyridin-2yl)-piperazin-1-ymethyl]-furo[3,2-b]pyridine

By the method used to prepare 2-[(4-phenyl-1-piperazinyl)methyl]furo[3,2-b]pyridine, furo[3,2-b]pyridine-2-carbaldehyde may be reacted with 1-(1-oxy-pyridin-2-yl)-piperazine to prepare 2-[4-(1-Oxy-pyridin-2-yl)-piperazin-1-ylmethyl]-furo[3,2-b]pyridine.

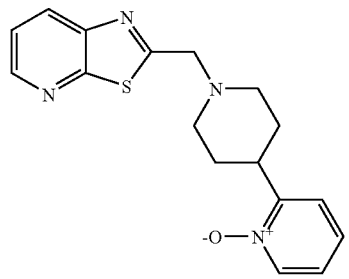

By the method used to prepare 2-{[4-(2-pyridinyl)-1-piperidinyl]methyl}[1,3]thiazolo[5,4-b]pyridine, 2-(chloromethyl)[1,3]thiazolo[5,4-b]pyridine may be reacted with 1',2',3',4',5',6'-hexahydro-[2,4']bipyridinyl 1-oxide to prepare 1'-Thiazolo[5,4-b]pyridin-2-ylmethyl-1',2',3',4',5',6'-hexahydro-[2,4']bipyridinyl 1-oxide.

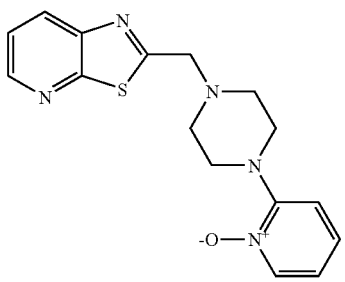

2-[4(1-Oxy-pyridin-2-yl-piperazin-1-ymethyl]-thiazolo[5,4-b]pyridine

By the method used to prepare 2-{[4-(2-pyridinyl)-1-piperidinyl]methyl}[1,3]thiazolo[5,4-b]$_p$yridine, 2-(chloromethyl)[1,3]thiazolo[5,4-b]pyridine may be reacted with 1-(1-oxy-pyridin-2-yl)-piperazine to prepare 2-[4-(1-Oxy-pyridin-2-yl)-piperazin-1-ylmethyl]-thiazolo[5,4-b]pyridine.

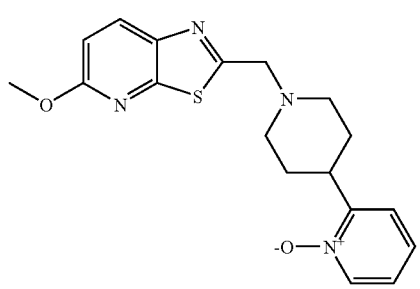

1'-(5-Methoxy-thiazolo[5,4-b]pyridin-2-ylmethyl)-1',2',3',4',5',6'-hexahydro-[2,4']bipyridinyl 1-oxide By the method used to prepare 4-{4-[(5-methoxy[1,3]thiazolo[5,4-b]pyridin-2-yl)methyl]-1-piperazinyl}phenol, 2-(chloromethyl)-5-methoxy[1,3]thiazolo[5,4-b]pyridine was reacted with 1',2',3',4',5',6'-hexahydro-[2,4']bipyridinyl 1-oxide to prepare 1'-(5-Methoxy-thiazolo[5,4-b]pyridin-2-ylmethyl)-1',2',3',4',5',6'-hexahydro-[2,4']bipyridinyl 1-oxide.

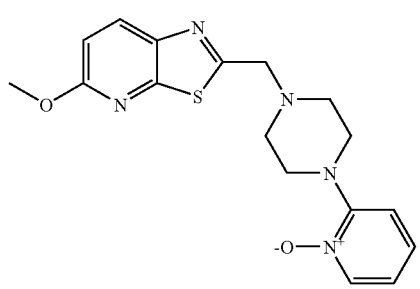

5-Methyl-2-[4-(1oxy-pyridin-2-yl)-piperazin-1-ylmethyl]-thiazolo[5,4-b]pyridine

By the method used to prepare 4-{4-[(5-methoxy[1,3]thiazolo[5,4-b]pyridin-2-yl)methyl]-1-piperazinyl}phenol, 2-(chloromethyl)-5-methoxy[1,3]thiazolo[5,4-b]pyridine was reacted with 1-(1-oxy-pyridin-2-yl)-piperazine to prepare 5-Methoxy-2-[4-(1-oxy-pyridin-2-yl)-piperazin-1-ylmethyl]-thiazolo[5,4-b]pyridine.

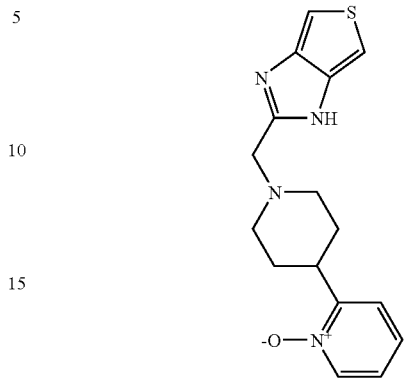

1'-(1H-Thieno[3,4-d]imidazol-2-ylmethyl)-1',2',3',4',5',6'-hexahydro-[2,4']bipyridinyl 1-oxide By the process used to prepare 2-{[4-(2-fluorophenyl)-1-piperazinyl]methyl}-1H-thieno[3,4-d]imidazole, 2-(chloromethyl)-1H-thieno[3,4-d]imidazole was reacted with 1',2',3',4',5',6'-hexahydro-[2,4']bipyridinyl 1-oxide to prepare 1'-(1H-Thieno[3,4-d]imidazol-2-ylmethyl)-1',2',3',4',5',6'-hexahydro-[2,4']bipyridinyl 1-oxide

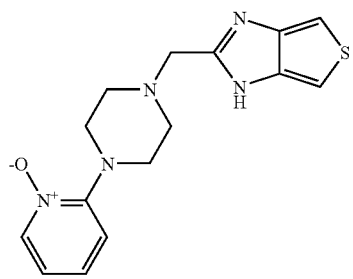

2-[4-(1-Oxy-pyridin-2yl)-piperazin-1-ylmethyl]-1H-thieno[3,4-d]imidazole

By the process used to prepare 2-{[4-(2-fluorophenyl)-1-piperazinyl]methyl}-1H-thieno[3,4-d]imidazole, 2-(chloromethyl)-1H-thieno[3,4-d]imidazole was reacted with 1-(1-oxy-pyridin-2-yl)-piperazine 2-[4-(1-Oxy-pyridin-2-yl)-piperazin-1-ylmethyl]-1H-thieno[3,4-d]imidazole.

In Vitro Data Functional Activity of $D_4$

Efficacies and potencies of compounds of the present invention at the human $D_4$ receptor were determined using a stable cell line containing the human $D_{4.4}$ receptor and a chimeric G protein in HEK-293 cells. This cell line allows a robust calcium signal detectable using a calcium fluorescent dye and a fluorescent imaging plate reader (FLIPR) (Coward et al., Anal. Biochem. 270: 242-248, 1999). Cells were plated (20000/well) into 96 well dishes and cultured for 48 hours. Media is removed, Fluo-4 dye added and cells incubated 1 hour at room temperature. Cells are washed with phosphate buffered saline to remove excess dye and compounds to be tested added to the wells and signal measured in FLIPR. Percent efficacy is the maximum response produced by the compound in relation to the maximum effect of 10 μM dopamine. The $EC_{50}$ is the effective concentration of the compound that causes 50% of the compound's maximum response.

Chimeric G-proteins allow a high-throughput signaling assay of Gi-coupled receptors, P. Coward, S. Chan, H. Wada, G. Humpries and B. Conklin, Analytical Biochemistry 270, 242-248 (1999).

Representative compounds of the present invention exhibited $EC_{50s}$, in the range of 7.5 nM to 3800 nM.

In Vivo Data Rat Penile Erection Model

Wistar rats were used as a primary animal model to study penile erection in vivo. All experiments were carried out between 9:00 AM and 3:00 PM in a diffusely illuminated testing room with a red light. Animals were weighed and allowed to adapt to the testing room for 60 minutes before the beginning of experiments. Rats were placed individually in a transparent cage (20×30×30 cm) after drug injection. The number of penile erections were recorded by direct observation for a period of 60 minutes after drug dosing, and the number of animals exhibiting 1 or more erections was expressed as incidence (%). (L)-Ascorbic acid in saline (1 mg/mL) was used as vehicle and apomorphine was used as a positive control at a dose of 0.1 μmol/kg.

Representative compounds of the present invention induced a minimum of 30% incidence of penile erections in rats after subcutaneous administration at doses of 0.01 μmol/kg to 1.0 μmol/kg.

The in vitro and in vivo data demonstrates that compounds of the present invention are dopamine $D_4$ receptor agonists that induce penile erections in rats.

As dopamine $D_4$ receptor agonists, compounds of the present invention can be used in combination with phosphodiesterase 5 inhibitors including, but not limited to, sildenafil or vardenafil as a method of treating sexual dysfunction in a mammal.

As dopamine $D_4$ receptor agonists, compounds of the present invention can be used in combination with an adrenergic receptor antagonist including, but not limited to, terazosin, prazosin or tamsulosin as method of treating sexual dysfunction in a mammal.

As dopamine $D_4$ receptor agonists, compounds of the present invention can be used in combination with a dopamine agonist including, but not limited to, apomorphine as a method of treating sexual dysfunction in a mammal.

Compounds of the present invention are dopamine $D_4$ receptor agonists and therefore are useful for the treatment of male sexual dysfunction, female sexual dysfunction, attention deficit hyperactivity disorder, Alzheimer's disease, drug abuse, Parkinson's disease, anxiety, schizophrenia, mood disorders and depression, as described in: The dopamine $D_4$ receptor: a controversial therapeutic target, N. J. Hrib, Drugs of the future 25:587-611 (2000); Dopamine and sexual behavior, M. Melis and A. Argiolas, Neuroscience and Biobehavioral Reviews 19:19-38 (1995); and Dopamine receptors: from structure to function, C. Missale, S. R. Nash, S. Robinson, M. Jabber and M. Caron, Physiological Reviews 78: 189-225 (1998).

Compounds of the present invention are dopamine $D_4$ receptor agonists and therefore are useful for the treatment of cardiovascular disorders. Dopamine and dopaminergic agents have been reported to exert pharmacologically significant cardiovascular effects on blood pressure and heart rate and are useful in the treatment of cardiovascular disorders, as described in: Chen F F, and Lin M T, Effects of dopamine, apomorphine gamma-hydroxybutyric acid, haloperidol, and pimozide on reflex bradycardia in rats, Journal of Pharmacology and Experimental Therapeutics (1980) 214: 427-432; and it has been reported that primate data support the potential clinical utility of dopamine receptor agonists in treating cardiovascular disease, as described in: Hahn, R A and MacDonald B R, Primate cardiovascular responses meditated by dopamine receptors: effects of N,N-dipropyldopamine and LY171555, Journal of Pharmacology and Experimental Therapeutics (1984) 229: 132-138.

Compounds of the present invention are dopamine $D_4$ receptor agonists and therefore are useful for the treatment of inflammation. Dopaminergic agents can exert anti-inflammatory effects and are useful for the treatment of diseases where inflammation plays a deleterious role, as described in: Bendele A M, Spaethe S M, Benslay D N, and Bryant H U, Anti-inflammatory activity of pergolide, a dopamine receptor agonist, in Journal of Pharmacology of Pharmacology and Experimental Therapeutics (1991) 259 169-175. Dopaminergic agents can also be of utility in the treatment of cancers, as described in: Lissoni P, Mandala M, Giani L, Malugani F, Secondino S, Zonato S, Rocco F, Gardani G, Efficacy of Bromocriptine in the Treatment of Metastatic Breast Cancer and Prostate Cancer-related Hyperprolactinemia, Neuroendocrinology Letters (2000) 21 405-408.

The term agonist, as used herein, means a compound of the present invention that exhibits 30% or greater efficacy in the in vitro assay described herein.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; such as cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The present invention provides pharmaceutical compositions which comprise compounds of the present invention formulated together with one or more non-toxic pharmaceutically acceptable carriers. The pharmaceutical compositions can be formulated for oral administration in solid or liquid form, for parenteral injection or for rectal administration.

Dosage forms for topical administration of a compound of the present invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated.

When used in the above or other treatments, a therapeutically effective amount of one of the compounds of the present invention can be employed in pure form or, where such forms exist, in pharmaceutically acceptable salt, ester, amide, or prodrug form. Alternatively, the compound can be administered as a pharmaceutical composition containing the compound of interest in combination with one or more pharmaceutically acceptable carriers. The phrase "therapeutically effective amount" of the compound of the present invention means a sufficient amount of the compound to treat disorders, at a reasonable benefit/risk ratio applicable to any medical treatment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of the present invention administered to a mammal, and particularly a human, may range from about 0.001 to about 30 mg/kg/day. For purposes of oral administration, more preferable doses can be in the range of from 0.01 to about 10 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which c an be prepared by mixing the compounds of the present invention with suitable non-irritating carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

The present invention contemplates pharmaceutically active compounds either chemically synthesized or formed by in vivo biotransformation to compounds of formula (I).

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The term "pharmaceutically acceptable salt, ester, amide, and prodrug" as used herein, refers to carboxylate salts, amino acid addition salts, zwitterions, esters, amides, and prodrugs of compounds of formula (I) which are within the scope of sound medical judgement, suitable for use in contact with the tissues of humans and lower animals without undue toxicity, irritation, allergic response, and the like, are commensurate with a reasonable benefit/risk ratio, and are effective for their intended use.

The compounds of the present invention can be used in the form of pharmaceutically acceptable salts derived from inorganic or organic acids. The term "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, sulfate, bis(tartrate), tartrate, (L) tartrate, bis((L) tartrate), (D) tartrate, bis((L) tartrate), (DL) tartrate, bis((DL) tartrate), meso-tartrate, bis(meso tartrate), thiocyanate, phosphate, glutamate, bicarbonate, p-toluenesulfonate and undecanoate. Examples of acids which can be employed to form pharmaceutically acceptable acid addition salts include such inorganic acids as hydrochloric acid, hydrobromic acid, sulphuric acid and phosphoric acid and such organic acids as maleic acid, fumaric acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Preferred salts of the compounds of the present invention include phosphate, tris and acetate.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the present invention may be rapidly transformed in vivo to compounds of formula (I), for example, by hydrolysis in blood.

The term "pharmaceutically acceptable ester" or "ester" as used herein, refers to esters of compounds of the present invention which hydrolyze in vivo and include those that break down readily in the human body to leave the parent compound or a salt thereof. Examples of pharmaceutically acceptable, non-toxic esters of the present invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods.

The term "pharmaceutically acceptable amide" or "amide" as used herein, refers to non-toxic amides of the present invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred.

Amides of the compounds of formula (I) may be prepared according to conventional methods.

What is claimed is:

1. A method of treating male erectile dysfunction in a mammal comprising administering to said mammal in need of such treatment a therapeutically effective amount of a compound selected from the group consisting of
   2-{[4-(3-methyl-2-pyridinyl)-1-piperazinyl]methyl}furo[3,2-b]pyridine;
   2-[4-(furo[3,2-b]pyridin-2-ylmethyl)-1-piperazinyl]nicotinonitrile; and
   2-{[4-(2-pyridinyl)-1-piperazinyl]methyl}furo[3,2-b]pyridine.

2. A method of treating male erectile dysfunction in a mammal comprising administering to said mammal in need of such treatment a therapeutically effective amount of a compound selected from the group consisting of
   5-methoxy-2-{[4-(6-methyl-2-pyridinyl)-1-piperazinyl]methyl}[1,3]thiazolo[5,4-b]pyridine;
   5-methoxy-2-{[4-(2-pyridinyl)-1-piperazinyl]methyl}[1,3]thiazolo[5,4-b]pyridine;
   2-{[4-(6-methyl-2-pyridinyl)-1-piperazinyl]methyl}[1,3]thiazolo[5,4-b]pyridine;
   2-[4-([1,3]thiazolo[5,4-b]pyridin-2-ylmethyl)-1-piperazinyl]nicotinonitrile; and
   2-{[4-(2-pyridinyl)-1-piperazinyl]methyl}[1,3]thiazolo[5,4-b]pyridine.

3. A method of treating male erectile dysfunction in a mammal comprising administering to said mammal in need of such treatment a therapeutically effective amount of a compound selected from the group consisting of
   4-(4-{[6-(trifluoromethyl)thieno[3,2-b]pyridin-2-yl]methyl}-1-piperazinyl)phenol;
   2-{[4-(2-methoxyphenyl)-1-piperazinyl]methyl}-6-(trifluoromethyl)thieno[3,2-b]pyridine;
   2-(4-{[6-(trifluoromethyl)thieno[3,2-b]pyridin-2-yl]methyl}-1-piperazinyl)benzonitrile;
   4-[4-(furo[3,2-b]pyridin-2-ylmethyl)-1-piperazinyl]phenol;
   2-[(4-phenyl-1-piperazinyl)methyl]furo[3,2-b]pyridine;
   2-{[4-(2-methoxyphenyl)-1-piperazinyl]methyl}furo[3,2-b]pyridine;
   2-[4-(furo[3,2-b]pyridin-2-ylmethyl)-1-piperazinyl]benzonitrile; and
   2-{[4-(2-fluorophenyl)-1-piperazinyl]methyl}furo[3,2-b]pyridine.

4. A method of treating male erectile dysfunction in a mammal comprising administering to said mammal in need of such treatment a therapeutically effective amount of a compound selected from the group consisting of
   2-{[4-(2-methoxyphenyl)-1-piperazinyl]methyl}[1,3]oxazolo[4,5-b]pyridine; and
   2-[4-([1,3]oxazolo[4,5-b]pyridin-2-ylmethyl)-1-piperazinyl]benzonitrile.

5. A method of treating male erectile dysfunction in a mammal comprising administering to said mammal in need of such treatment a therapeutically effective amount of a compound is selected from the group consisting of
   4-{4-[(5-methoxy[1,3]thiazolo[5,4-b]pyridin-2-yl)methyl]-1-piperazinyl}phenol;
   2-{[4-(2-fluorophenyl)-1-piperazinyl]methyl}-5-methoxy[1,3]thiazolo [5,4-b]pyridine;
   5-methoxy-2-({4-[2-(methylthio)phenyl]-1-piperazinyl}methyl)[1,3]thiazolo[5,4-b]pyridine;
   5-methoxy-2-{[4-(2-methoxyphenyl)-1-piperazinyl]methyl}[1,3]thiazolo[5,4-b]pyridine;
   2-{[4-(2-chlorophenyl)-1-piperazinyl]methyl}-5-methoxy[1,3]thiazolo[5,4-b]pyridine;
   2-{4-[(5-methoxy[1,3]thiazolo[5,4-b]pyridin-2-yl)methyl]-1-piperazinyl}benzonitrile;
   2-{[4-(2-chlorophenyl)-1-piperazinyl]methyl}[1,3]thiazolo[5,4-b]pyridine;
   2-{[4-(5-chloro-2-methoxyphenyl)-1-piperazinyl]methyl}[1,3]thiazolo[5,4-b]pyridine;
   4-[4-([1,3]thiazolo[5,4-b]pyridin-2-ylmethyl)-1-piperazinyl]phenol;
   2-({4-[2-(methylthio)phenyl]-1-piperazinyl}methyl)[1,3]thiazolo[5,4-b]pyridine;
   2-{[4-(2-fluorophenyl)-1-piperazinyl]methyl}[1,3]thiazolo[5,4-b]pyridine;
   2-[4-([1,3]thiazolo[5,4-b]pyridin-2-ylmethyl)-1-piperazinyl]benzonitrile;
   2-{[4-(2-methoxyphenyl)-1-piperazinyl]methyl}[1,3]thiazolo[5,4-b]pyridine; and
   2-[(4-phenyl-1-piperazinyl)methyl][1,3]thiazolo[5,4-b]pyridine.

6. A method of treating male erectile dysfunction in a mammal comprising administering to said mammal in need of such treatment a therapeutically effective amount of a compound selected from the group consisting of
   5-methoxy-2-{[4-(2-pyrimidinyl)-1-piperazinyl]methyl}[1,3]thiazolo[5,4-b]pyridine; and
   2-{[4-(2-pyrimidinyl)-1-piperazinyl]methyl}[1,3]thiazolo[5,4-b]pyridine.

7. A method of treating male erectile dysfunction in a mammal comprising administering to said mammal in need of such treatment a therapeutically effective amount of
   2-{[4-(1,3-thiazol-2-yl)-1-piperazinyl]methyl}[1,3]thiazolo[5,4-b]pyridine.

* * * * *